(12) United States Patent
Vidlund

(10) Patent No.: US 9,895,221 B2
(45) Date of Patent: Feb. 20, 2018

(54) MULTI-COMPONENT DESIGNS FOR HEART VALVE RETRIEVAL DEVICE, SEALING STRUCTURES AND STENT ASSEMBLY

(71) Applicant: Tendyne Holdings, Inc., Roseville, MN (US)

(72) Inventor: Robert Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 0 days.

(21) Appl. No.: 14/607,888

(22) Filed: Jan. 28, 2015

(65) Prior Publication Data

US 2015/0142103 A1     May 21, 2015

Related U.S. Application Data

(63) Continuation of application No. PCT/US2013/051308, filed on Jul. 19, 2013.
(Continued)

(51) Int. Cl.
*A61F 2/24* (2006.01)
*A61F 2/95* (2013.01)

(52) U.S. Cl.
CPC .......... *A61F 2/2418* (2013.01); *A61F 2/2439* (2013.01); *A61F 2/2457* (2013.01); *A61F 2002/9534* (2013.01); *A61F 2220/0008* (2013.01); *A61F 2250/0003* (2013.01); *A61F 2250/006* (2013.01); *A61F 2250/0069* (2013.01)

(58) Field of Classification Search
None
See application file for complete search history.

(56) References Cited

U.S. PATENT DOCUMENTS 2,697,008 A    12/1954  Rowley
3,409,013 A    11/1968  Berry
(Continued)

FOREIGN PATENT DOCUMENTS

CN    1486161        3/2004
CN    1961845 A      5/2007
(Continued)

OTHER PUBLICATIONS

US 9,155,620, 10/2015, Gross et al. (withdrawn)
(Continued)

*Primary Examiner* — Ann Schillinger
(74) *Attorney, Agent, or Firm* — Cooley LLP

(57) ABSTRACT

This invention relates to the design and function of a device which allows for retrieval of a previously implanted valve prosthesis from a beating heart without extracorporeal circulation using a transcatheter retrieval system, including a guide component to facilitate the compression of the valve and retraction into a retrieval catheter, as well as an improved prosthetic transcatheter heart valve having one or more of: a series of radially extending tines having a loop terminus to improve sealing a deployed prosthetic mitral valve against hemodynamic leaking, a pre-compressible stent-in-stent design, or an articulating cuff attached to a covered stent-valve and a commissural sealing skirt structure attached to the underside of the articulating cuff.

19 Claims, 42 Drawing Sheets

Related U.S. Application Data

(60) Provisional application No. 61/676,897, filed on Jul. 28, 2012, provisional application No. 61/676,899, filed on Jul. 28, 2012, provisional application No. 61/677,329, filed on Jul. 30, 2012.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |

(56) References Cited

U.S. PATENT DOCUMENTS

| | | |
|---|---|---|
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | Dell et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |

(56) References Cited

U.S. PATENT DOCUMENTS

| | | |
|---|---|---|
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,979,922 B2 | 3/2015 | Thambar et al. |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,526,611 B2 | 12/2016 | Tegels et al. |
| 9,597,181 B2 | 3/2017 | Christianson et al. |
| 2001/0018611 A1 | 8/2001 | Solem et al. |
| 2001/0021872 A1 | 9/2001 | Bailey et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |

(56) References Cited

U.S. PATENT DOCUMENTS

| | | |
|---|---|---|
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesscr et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264206 A1 | 10/2011 | Tabor |
| 2011/0288637 A1 | 11/2011 | De Marchena |
| 2011/0319988 A1* | 12/2011 | Schankereli .......... A61F 2/2418 623/2.11 |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford et al. |

(56) References Cited

U.S. PATENT DOCUMENTS

| | | |
|---|---|---|
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0283824 A1 | 11/2012 | Lutter et al. |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1* | 7/2013 | Vidlund ............ A61B 17/0401 623/1.12 |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1* | 11/2013 | McLean ............... A61F 2/2427 623/2.18 |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1* | 10/2014 | Tegels ................. A61F 2/2412 623/2.11 |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0358224 A1 | 12/2014 | Tegels et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011321 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127096 A1 | 5/2015 | Rowe et al. |
| 2015/0142100 A1 | 5/2015 | Morriss et al. |
| 2015/0142101 A1 | 5/2015 | Coleman et al. |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0262879 A1 | 9/2016 | Meiri et al. |
| 2016/0317290 A1 | 11/2016 | Chau et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |

FOREIGN PATENT DOCUMENTS

| | | |
|---|---|---|
| CN | 2902226 | 5/2007 |
| CN | 101146484 | 3/2008 |
| CN | 102869318 | 1/2013 |
| CN | 103220993 | 7/2013 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |

(56) References Cited

FOREIGN PATENT DOCUMENTS

| | | |
|---|---|---|
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/070372 | 7/2006 |
| WO | WO 2006/113906 | 10/2006 |
| WO | WO 2007/081412 | 7/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/159342 | 12/2011 |
| WO | WO 2011/163275 | 12/2011 |
| WO | WO 2012/036742 | 3/2012 |
| WO | WO 2012/177942 | 12/2012 |
| WO | WO 2013/045262 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2015/051430 | 4/2015 |
| WO | WO 2015/058039 | 4/2015 |
| WO | WO 2015/063580 | 5/2015 |
| WO | WO 2015/120122 | 8/2015 |
| WO | WO 2015/138306 | 9/2015 |
| WO | WO 2016/112085 | 7/2016 |
| WO | WO 2016/126942 | 8/2016 |
| WO | WO 2016/168609 | 10/2016 |
| WO | WO 2016/198933 | 12/2016 |

OTHER PUBLICATIONS

International Search Report and Written Opinion for International Application No. PCT/US2013/051308, dated Nov. 8, 2013, 13 pages.

Al Zaibag, M. et al., "Percutaneous Balloon Valvotomy in Tricuspid Stenosis," British Heart Journal, Jan. 1987, 57(1):51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R. et al., "Transluminal implantation of artificial heart valves. Description of a new expandable aortic valve and initial results with implantation by catheter technique in closed chest pigs," European Heart Journal, 1992, 13(5):704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Bernacca, G. M. et al., "Polyurethane heart valves: Fatigue failure, calcification, and polyurethane structure," Journal of Biomedical Materials Research, Mar. 5, 1997, 34(3):371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration In Dilated Hearts," Interactive CardioVascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142.html> , Dec. 10, 2012, 5 pages.

Gray, H., The Heart, Anatomy of the Human Body, 1918, Retrieved from the Internet <http://education.yahoo.com/referenee/gray/subjects/subject/138> , Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-arteries-gets-a-faili...,>, published Jan. 3, 1991, retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardio-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2):194-198.

Moazami, N. et al., "Transluminal aortic valve placement: A feasibility study with a newly designed collapsible aortic valve," ASAIO Journal, Sep./Oct. 1996, 42(5):M381-M385.

Orton, C., "Mitralscal: Hybrid Transcatheter Mitral Valve Replacement," Retrieved from the Internet: <http:/www.acvs.org/symposium/proceedings2011/data/papers/102.pdf>, pp. 311-312.

Pavcnik, D. et al. "Development and Initial Experimental Evaluation of a Prosthetic Aortic Valve for Transcatheter Placement," Radiology, 1992; 183:151-154.

(56) References Cited

OTHER PUBLICATIONS

Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal, Sep. 1989, 10(9):774-782.
"Shape Memory Alloys," Retrieved from the Internet: <http://webdocs.cs.ualberta.ca/~database/MEMS/sma.html>, Feb. 5, 2016, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150(5):1185-1187.
Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.
Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," In Polymetric Materials and Artificial Organs, American Chemical Society, 1984, pp. 111-150.

\* cited by examiner

MULTI-COMPONENT DESIGNS FOR HEART VALVE RETRIEVAL DEVICE, SEALING STRUCTURES AND STENT ASSEMBLY

CROSS-REFERENCE TO RELATED APPLICATIONS

This application is a continuation of International Application No. PCT/US2013/051308, filed Jul. 19, 2013, entitled "IMPROVED MULTI-COMPONENT DESIGNS FOR HEART VALVE RETRIEVAL DEVICE, SEALING STRUCTURES AND STENT ASSEMBLY," which claims priority to and the benefit of U.S. Provisional Application No. 61/676,897, filed Jul. 28, 2012; Provisional Application No. 61/676,899, filed Jul. 28, 2012 and Provisional Application No. 61/677,329, filed Jul. 30, 2012. The disclosure of each of the foregoing applications is incorporated herein by reference in its entirety.

BACKGROUND

Field of the Invention

This invention relates to novel devices and methods for (1) improved retrievability of a transcatheter heart valve replacement, and in particular a collapsable prosthetic heart valve for treating mitral regurgitation or other pathological vascular conditions, (2) a prosthetic transcatheter valve for treating mitral regurgitation or other pathological vascular condition, and in particular to new prosthetic transcatheter mitral valve components for sealing the area below the mitral annulus to further reduce or prevent leaking attendant to the implant of the prosthetic valve, (3) prosthetic transcatheter valve for treating mitral regurgitation or other pathological vascular condition, and in particular to a new prosthetic transcatheter mitral valve having a stent-in-a-stent design for improving sealing within the mitral annulus to further reduce or prevent leaking attendant to the implant of the prosthetic valve; and (4) prosthetic transcatheter valve for treating mitral regurgitation or other pathological vascular condition, and in particular to new prosthetic transcatheter mitral valve components for sealing the area below the mitral annulus to further reduce or prevent leaking attendant to the implant of the prosthetic valve.

Background of the Invention

Valvular heart disease and specifically aortic and mitral valve disease is a significant health issue in the US Annually approximately 90,000 valve replacements are conducted in the US. Traditional valve replacement surgery, the orthotopic replacement of a heart valve, is an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients.

Thus if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Several designs for catheter-deployed (transcatheter) aortic valve replacement are under various stages of development. The Edwards SAPIEN transcatheter heart valve is currently undergoing clinical trial in patients with calcific aortic valve disease who are considered high-risk for conventional open-heart valve surgery. This valve is deployable via a retrograde transarterial (transfemoral) approach or an antegrade transapical (transventricular) approach. A key aspect of the Edwards SAPIEN and other transcatheter aortic valve replacement designs is their dependence on lateral fixation (e.g. tines) that engages the valve tissues as the primary anchoring mechanism. Such a design basically relies on circumferential friction around the valve housing or stent to prevent dislodgement during the cardiac cycle. This anchoring mechanism is facilitated by, and may somewhat depend on, a calcified aortic valve annulus. This design also requires that the valve housing or stent have a certain degree of rigidity.

At least one transcatheter mitral valve design is currently in development. The Endo-valve uses a folding tripod-like design that delivers a tri-leaflet bioprosthetic valve. It is designed to be deployed from a minimally invasive transatrial approach, and could eventually be adapted to a transvenous atrial septotomy delivery. This design uses "proprietary gripping features" designed to engage the valve annulus and leaflets tissues. Thus the anchoring mechanism of this device is essentially equivalent to that used by transcatheter aortic valve replacement designs.

Various problems continue to exist in this field, including problems with how to retrieve a collapsable heart valve prosthetic from the native valve once the prosthetic has reached the end of its useful life. For example, a prosthetic heart valve may be delivered and secured percutaneously or intravenously using a catheter and endoscope or similar device, but the process of disengaging anchoring mechanisms and collapsing the prosthetic for retrieval is often more difficult to accomplish than is the delivery. Accordingly, there is a need for an improved device and method for retrieval when such valves need to be replaced.

Further problems include insufficient articulation and sealing of the valve within the native annulus, pulmonary edema due to poor atrial drainage, perivalvular leaking around the install prosthetic valve, lack of a good fit for the prosthetic valve within the native mitral annulus, atrial tissue erosion, excess wear on the nitinol structures, interference with the aorta at the posterior side of the mitral annulus, and lack of customization, to name a few. Accordingly, there is still a need for each of (i) an improved valve having a articulating collar support structures for a prosthetic mitral valve, (ii) an improved valve having little or no leakage, especially from the commissural areas, and (iii) an improved valve having a commissural sealing structure for a prosthetic mitral valve.

SUMMARY

The Bulletnose Retrieval Device

In one embodiment, prosthetic heart valve retrieval device comprising two or more valve tethers, a retrieval guide component, and a single retrieval tether.

In another preferred embodiment, the prosthetic heart valve retrieval device of the paragraph 15, further comprising wherein the proximal end of the valve tethers are attached at intervals around the nearer, proximal rim of the prosthetic valve, and the distal end of the valve tethers are attached to the proximal tip of the retrieval guide component.

In another preferred embodiment, the prosthetic heart valve retrieval device of the paragraph 15, further comprising wherein the distal tip of the retrieval guide component is attached to the proximal end of the single retrieval tether.

In another preferred embodiment, the prosthetic heart valve retrieval device of the paragraph 15, further comprising wherein all components are comprised of a single, integral piece of metal.

In another preferred embodiment, the prosthetic heart valve retrieval device of the paragraph 15, further comprising wherein the retrieval guide component is bullet-shaped, cone-shaped, hooded, or otherwise shaped to guide the valve tethers and prosthetic valve into a retrieval catheter.

In another preferred embodiment, the prosthetic heart valve retrieval device of the paragraph 15, further comprising wherein the retrieval guide component is comprised of a ring, with or without perforations, overlaying and integrated with or adhered to a bullet-shaped, cone-shaped or hooded component.

In another preferred embodiment, the prosthetic heart valve retrieval device of the paragraph 16, further comprising wherein the prosthetic heart valve to be retrieved is seated within a metal stent.

In another preferred embodiment, the prosthetic heart valve retrieval device of the paragraph 21, further comprising wherein the stent is laser cut.

In another preferred embodiment, the prosthetic heart valve retrieval device of the paragraph 21, further comprising wherein the stent is comprised of braided wire.

In another preferred embodiment, the prosthetic heart valve retrieval device of the paragraph 21, further comprising wherein the stent and the components of the retrieval device comprise a single, integral piece of material.

In another preferred embodiment, the prosthetic heart valve retrieval device of the paragraph 21, further comprising wherein the valve tethers are tied or otherwise adhered to the proximal rim of the stent.

In another preferred embodiment, the prosthetic heart valve retrieval device of the paragraph 21, further comprising wherein the stent is also integrated with or adhered to an anti-regurgitation cuff component comprising a circular or elliptical ring emanating from the side or upper, distal rim of the stent.

In another preferred embodiment, the prosthetic heart valve retrieval device of the paragraph 26, further comprising wherein the stent and/or cuff components are covered with biocompatible fabric or tissue.

In another preferred embodiment, the prosthetic heart valve retrieval device of the paragraph 15, comprised of a biocompatible metal, alloy, or polymer.

In another preferred embodiment, the prosthetic heart valve retrieval device of the paragraph 15, comprised of Nitinol or another shape-memory alloy or material.

In another preferred embodiment, the prosthetic heart valve retrieval device of the paragraph 15, further comprising wherein the tethers are comprised of a biocompatible thread, wire or similar material.

In another preferred embodiment, the prosthetic heart valve retrieval device of the paragraph 15, further comprising wherein the tethers are comprised of Dacron or a polymer with similar properties.

In another preferred embodiment, the prosthetic heart valve retrieval device of the paragraph 15, further comprising wherein the tethers are comprised of Nitinol or another shape-memory alloy or material.

In another preferred embodiment, the prosthetic heart valve retrieval device of the paragraph 15, further comprising wherein the single retrieval tether is of a larger gauge than the valve tethers.

A prosthetic heart valve extraction apparatus comprising a handle having an actuator and an actuator spring, a tensioning unit mounted for reciprocal motion responsive to the operation of the actuator, a traveller strap with a tooth and pawl mechanism, removably mounted within a strap mount of the tensioning unit, a catheter removably held by a catheter mount which is connected to a distal end of the traveller strap, and a pulling rod comprising a distal end partially disposed within said catheter and a proximal end that engages a puller mount on said handle.

In another preferred embodiment, the extraction apparatus of paragraph 34, further comprising a snare attachment at the distal end of the catheter.

A prosthetic heart valve retrieval apparatus comprising the retrieval guide of any of claims 15-33 and the extraction apparatus of paragraph 34.

A method of retrieving a tethered expandable prosthetic heart valve apparatus, using the retrieval apparatus of any of claims 1-33 and comprising the steps of (i) capturing the lower, distal end of the single retrieval tether to the catheter, (ii) retracting the single retrieval tether into the catheter, (iii) retracting the retrieval guide and then the plurality of tethers into the catheter, (iv) collapsing the expandable stent as the plurality of tethers are drawn together during such retraction and (v) retracting the entire expandable prosthetic heart valve apparatus into the catheter as it collapses.

In another preferred embodiment, the method of paragraph 37, further comprising use of the extraction apparatus of paragraph 34 to affect capturing the single retrieval tether and retracting the expandable prosthetic heart valve apparatus.

In another preferred embodiment, the method of paragraph 37, further comprising the step of extracting the valve by directly accessing the heart through the intercostal space, using an apical approach to enter the ventricle.

In another preferred embodiment, the method of paragraph 37, further comprising the step of extracting the valve by directly accessing the heart through a thoracotomy, sternotomy, or minimally-invasive thoracic, thorascopic, or trans-diaphragmatic approach to enter the left ventricle.

In another preferred embodiment, the method of paragraph 37, further comprising the step of extracting the valve by directly accessing the heart through the intercostal space, using an approach through the lateral ventricular wall to enter the left ventricle.

In another preferred embodiment, the method of paragraph 37, further comprising the step of extracting the valve by accessing the left atrium of the heart using a transvenous atrial septostomy approach.

In another preferred embodiment, the method of paragraph 37, further comprising the step of extracting the valve by accessing the left ventricle of the heart using a transvenous ventricular septostomy approach.

In another preferred embodiment, the method of paragraph 37, further comprising the step of extracting the valve by accessing the left ventricle of the heart using a transarterial retrograde aortic valve approach.

In another preferred embodiment, the method of paragraph 37, wherein the method is used to retrieve a prosthetic mitral valve.

In another preferred embodiment, the method of paragraph 37, wherein the method is used to retrieve a prosthetic aortic valve.

In another embodiment, method of retrieving a tethered expandable transcatheter prosthetic heart valve that is deployed within the heart, comprising the step of: retracting the tethered expandable transcatheter prosthetic heart valve into a retrieval catheter located within the heart, wherein the tethered expandable transcatheter prosthetic heart valve comprises a retrieval guide located between the expandable prosthetic heart valve and a tether structure, the expandable prosthetic heart valve comprising a stent structure with internal valve leaflets, the stent structure having an anti-regurgitation mechanism at its upper end, said anti-regurgitation mechanism selected from an upper cuff component or wherein the stent structure is wedge shaped, the distal cuff and wedge-shape providing anchoring tension within the deployment location, the stent structure having a tether-attachment structure at its lower end, said tether structure comprising one or more tethers attached to the tether-attachment structure, and wherein said retrieval guide is bullet-shaped, cone-shaped, hooded or otherwise shaped to guide or receive the lower end of the expandable transcatheter prosthetic heart valve and facilitate the compression of the expandable transcatheter prosthetic heart valve to approximately the same diameter as the retrieval catheter and facilitate the retraction of the compressed expandable transcatheter prosthetic heart valve into the retrieval catheter.

In another embodiment, method of quickly retrieving a prosthetic heart valve having one or more tethers from a patient comprising the steps of: capturing one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment or for replacement of a defective or improperly sized prosthesis.

Sealing Canopy

In a preferred embodiment, there is provided a pre-configured compressible transcatheter prosthetic cardiovascular valve having an improved peri-annular sealing component, which comprises an expandable leaflet assembly comprised of stabilized tissue or synthetic material, said leaflet assembly disposed within an expandable stent having a flared distal end comprised of a plurality of articulating collar support structures, said expandable stent having a proximal end comprised of an integral tether connection apparatus and a wire halo apparatus, said peri-annular sealing component comprising a passively oscillating dome-shaped sealing canopy comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a periannular seal by retrograde hemodynamic forces.

The design as provided focuses on the deployment of a device via a minimally invasive fashion and by way of example considers a minimally invasive surgical procedure utilizing the intercostal or subxyphoid space for valve introduction, but may also include standard retrograde, or antegrade transcatheter approaches. In order to accomplish this, the valve is formed in such a manner that it can be compressed to fit within a delivery system and secondarily ejected from the delivery system into the target location, for example the mitral or tricuspid valve annulus.

Passively Oscillating Dome-Shaped Periannular Sealing Canopy Structures with Stent Variations In a preferred embodiment, there is provided a prosthetic mitral valve containing an expandable leaflet assembly comprised of stabilized tissue or synthetic material disposed within a self-expanding stent having a flared collar at its distal end and a wire halo at its proximal with a passively oscillating dome-shaped periannular sealing canopy structure.

In another preferred embodiment, there is provided a prosthetic heart valve as described having a single tether connecting the proximal end of the stent to an epicardial securing device at or near the apex of the left ventricle. In another preferred embodiment, the prosthetic mitral valve does not use an anchoring or positioning tether at all, and instead is held in the mitral annulus by the wrapping forces of the native leaflets, and optionally one or more standard anchoring elements, including but not limited to barbs, pins, and/or hooks, or combinations thereof.

In another preferred embodiment, there is provided a prosthetic heart valve as described, wherein the peri-annular sealing component comprises an enlarged passively oscillating dome-shaped sealing canopy that has a sub-annular diameter about the same diameter as the atrial collar.

In another preferred embodiment, there is provided a prosthetic heart valve as described wherein the peri-annular sealing component comprises two or more passively oscillating dome-shaped sealing canopies, each comprised of a skirt of stabilized tissue or synthetic material attached on a distal edge of said material at or near the distal end of the stent and attached at a proximal edge to the wire halo apparatus, wherein during systole the leaflet assembly closes and each of the sealing canopies is filled to form multiple redundant periannular seal partitions by retrograde hemodynamic forces.

In another preferred embodiment, there is provided a prosthetic heart valve as described wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a supra-annular seal partition by retrograde hemodynamic forces.

In another preferred embodiment, there is provided a prosthetic heart valve as described wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a combined sub-annular and supra-annular seal partition by retrograde hemodynamic forces.

In another preferred embodiment, there is provided a prosthetic heart valve as described wherein the peri-annular sealing component comprises an enlarged gel-filled sealing chamber that has a sub-annular diameter about the same diameter as the atrial collar and which is attached to the wire halo on the ventricular side and to the stent body on the periannular side.

In another preferred embodiment, there is provided a prosthetic heart valve as described wherein the peri-annular sealing component comprises an enlarged gel-filled sealing chamber that has a sub-annular diameter about the same diameter as the atrial collar and which is attached to the proximal end of the stent body on the ventricular side and to a midline section of the stent body on the periannular side.

In another preferred embodiment, there is provided a prosthetic cardiovascular valve with a stent body that has a low height to width profile.

In a preferred embodiment, the prosthetic mitral valve contains an improved stent body that is a half-round D-shape in cross-section.

In a preferred embodiment, the prosthetic mitral valve contains an improved stent body that is a bent tubular stent structure wherein the bend is directed away from the anterior leaflet, away from interfering with coaptation of adjacent, e.g. aortic, valvular leaflets.

In a preferred embodiment, the prosthetic mitral valve contains an improved stent body that has a low height to width profile and the leaflet structure disposed within the stent is positioned at or near the atrial end of the stent body.

In another preferred embodiment, the a prosthetic mitral valve has a stent body made from both braided wire (atrial end) and laser-cut metal (annular or ventricular end), or vice versa.

Additional Features for Improved Stents

In a preferred embodiment, the prosthetic heart valve has a cuff that has articulating wire articulating radial tines or posts of wire of various lengths.

In another preferred embodiment, the prosthetic heart valve has at least one elastic tether to provide compliance during the physiologic movement or conformational changes associated with heart contraction.

In another preferred embodiment, the prosthetic heart valve has a stent body and cuff that are made from a superelastic metal.

In another preferred embodiment, the prosthetic heart valve has a tether which is used to position the valve cuff into the mitral annulus to prevent perivalvular leak.

In another preferred embodiment, the tethers are bioabsorbable and provide temporary anchoring until biological fixation of the prosthesis occurs. Biological fixation consisting of fibrous adhesions between the leaflet tissues and prosthesis or compression on the prosthesis by reversal of heart dilation, or both.

In another preferred embodiment, the prosthetic heart valve has a cuff for a prosthetic heart valve, said cuff being covered with tissue.

In another preferred embodiment, the cuff is covered with a synthetic polymer selected from expandable polytetrafluoroethylene (ePTFE) or polyester.

In another preferred embodiment, there is provided a prosthetic heart valve that has leaflet material constructed from a material selected from the group consisting of polyurethane, polytetrafluoroethylene, pericardium, and small intestine submucosa.

In another preferred embodiment, there is provided a prosthetic heart valve having surfaces that are treated with anticoagulant.

In another preferred embodiment, there is provided a prosthetic heart valve having a cuff and containing anchoring tethers which are attached to the cuff.

In another preferred embodiment, there is provided a prosthetic heart valve having a cuff and containing anchoring tethers which are attached to the cuff and at both commissural tips.

In another preferred embodiment, there is provided a prosthetic heart valve having a cuff where the cuff attachment relative to the body is within the angles of about 60 degrees to about 150 degrees.

In another preferred embodiment, there is provided a prosthetic heart valve containing a combination of tethers and barbs useful for anchoring the device into the mitral annulus.

In another embodiment, the wire of the cuff is formed as a series of radially extending articulating radial tines or posts of wire of equal or variable length.

In another embodiment, the cuff extends laterally beyond the expanded tubular stent according to a ratio of the relationship between the height of the expanded deployed stent (h) and the lateral distance that the cuff extends onto the tissue (1). Preferably, the h/1 ratio can range from 1:10 to 10:1, and more preferably includes without limitation 1:3, 1:2, 1:1, 2:1, and fractional ranges there between such as 1.25:2.0, 1.5:2.0, and so forth. It is contemplated in one non-limiting example that the cuff can extend laterally (1) between about 3 and about 30 millimeters.

In another embodiment, there is provided a feature wherein the tubular stent has a first end and a second end, wherein the cuff is formed from the stent itself, or in the alternative is formed separately and wherein the cuff is located at the first end of the stent, and the second end of the tubular stent has a plurality of tether attachment structures.

In another embodiment, there is provided a feature further comprising a plurality of tethers for anchoring the prosthetic heart valve to tissue and/or for positioning the prosthetic heart valve.

In another embodiment, there is provided a feature further comprising an epicardial tether securing device, wherein the tethers extend from about 2 cm to about 20 cm in length, and are fastened to an epicardial tether securing device. Some pathological conditions within a ventricle may require a atrial-apical tether from about 8 to about 15 cm, or more as described within the range above.

In another embodiment, there is provided a catheter delivery system for delivery of a prosthetic heart valve which comprises a delivery catheter having the prosthetic heart valve disposed therein, and an obturator for expelling the prosthetic heart valve.

In another embodiment, there is provided an assembly kit for preparing the catheter delivery system which comprises a compression funnel, an introducer, a wire snare, an obturator, a delivery catheter, and a prosthetic heart valve, wherein the compression funnel has an aperture for attaching to the introducer, wherein said introducer is comprised of a tube having a diameter that fits within the diameter of the delivery catheter, wherein said obturator is comprised of a tube fitted with a handle at one end and a cap at the other end, wherein said cap has an opening to allow the wire snare to travel therethrough, and said obturator has a diameter that fits within the diameter of the introducer, and wherein said prosthetic heart valve is compressible and fits within the delivery catheter.

In another embodiment, there is provided a method of treating mitral regurgitation and/or tricuspid regurgitation in a patient, which comprises the step of surgically deploying the prosthetic heart valve described herein into the annulus of the target valve structure, e.g. mitral valve annulus and tricuspid valve annulus of the patient.

In another embodiment, there is provided a feature wherein the prosthetic heart valve is deployed by directly accessing the heart through an intercostal space, using an apical approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through a thoracotomy, sternotomy, or minimally-invasive thoracic, thorascopic, or transdiaphragmatic approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through the intercostal space, using a lateral approach to enter the left or right ventricle, and deploying the prosthetic heart valve into the valvular annulus using the catheter delivery system.

In another embodiment, there is provided a feature wherein the prosthetic heart valve is deployed by accessing the left heart using either an antegrade-trans(atrial)septal (transvenous-trans(atrial)septal) approach or a retrograde (transarterial-transaortic) catheter approach to enter the left heart, and deploying the prosthetic heart valve into the mitral annulus using the catheter delivery system.

In another embodiment, there is provided a feature wherein the prosthetic heart valve is deployed into the mitral annulus from a retrograde approach by accessing the left ventricle through the apex of the ventricular septum (transvenous-trans(ventricular)septal approach).

In another embodiment, there is a feature wherein the prosthetic heart valve is deployed into the mitral position using a retrograde transventricular septal approach and the tethers are anchored into or on the right ventricular side of the ventricular septum.

In another embodiment, there is provided a feature further comprising tethering the prosthetic heart valve to tissue within the left ventricle.

In another embodiment, there is provided a feature wherein the prosthetic heart valve is tethered to the apex of the left ventricle using an epicardial tether securing device.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment.

Articulating Collar Support Structures with Collar Variations

In another preferred embodiment, there is provided a method of sealing a deployed prosthetic mitral valve against hemodynamic leaking, comprising fitting a prosthetic mitral valve with a flared end or cuff having articulating collar support structures prior to deployment wherein the flared end or cuff is constructed to contour to the commissures of a pathologically defective mitral valve and constructed to contour to the zone of coaptation of the pathologically defective mitral valve, wherein the flared end or cuff is formed from wire originating from one end of an expandable tubular braided wire stent and the flared end or cuff is covered with stabilized tissue or synthetic material, the commissural contour components of the flared end or cuff and the zone of coaptation contour components of the flared end or cuff forming a complete or partial saddle-shape wherein the commissural contour components are in direct communication with the mitral valve commissures, and the zone of coaptation contour components are in direct communication with the mitral valve zone of coaptation.

In a preferred embodiment, the flared end or cuff shape is agaricoid.

In another preferred embodiment, the flared end or cuff shape is onychoid.

In another preferred embodiment, the flared end or cuff shape is reniform.

In another preferred embodiment, the flared end or cuff shape is an oval.

In another preferred embodiment, the flared end or cuff shape is a truncated-oval having a squared end.

In another preferred embodiment, the flared end or cuff shape is propeller-shaped having two or three blades.

In another preferred embodiment, the flared end or cuff shape is cruciform.

In another preferred embodiment, the flared end or cuff shape is petal-shaped having flat radial covered articulating radial tines or posts of wire.

In another preferred embodiment, the flared end or cuff shape is irregular or amoeboid.

In another preferred embodiment, the flared end or cuff shape is cotyloid shaped.

In another preferred embodiment, the flared end or cuff shape is a partial half-round fan-shape.

In another preferred embodiment, the flared end or cuff shape is a rectangular U-shape.

In another preferred embodiment, the flared end or cuff is constructed from ductile metal.

In another preferred embodiment, the flared end or cuff shape is constructed with a cover of stabilized tissue that is derived from adult, or 90-day old, or 30 day old bovine, ovine, equine or porcine pericardium, or from animal small intestine submucosa.

In another preferred embodiment, the flared end or cuff shape is constructed with a cover of synthetic material is selected from the group consisting of polyester, polyurethane, and polytetrafluoroethylene.

In another preferred embodiment, the stabilized tissue or synthetic material is treated with anticoagulant.

In another preferred embodiment, the method further comprises the step of anchoring the prosthetic heart valve to tissue uses a plurality of tethers to the flared end or cuff.

In another preferred embodiment, the method further comprises the step of anchoring the prosthetic heart valve to tissue using a single tether attached to the stent or a tether-attachment structure attached to the stent.

In another preferred embodiment, at least one of the plurality of tethers is an elastic tether.

In another preferred embodiment, at least one of the plurality of tethers is a bioresorbable tether.

Stent-in-a-Stent

In a preferred embodiment, there is provided a pre-configured compressible transcatheter prosthetic cardiovascular valve having an improved stent-in-a-stent sealing design, which comprises an expandable leaflet assembly comprised of stabilized tissue or synthetic material, said leaflet assembly disposed within an expandable inner stent having an articulating collar structure at its distal end and a tether apparatus attached to its proximal end, said inner stent being partially or wholly disposed within an outer stent.

The design as provided focuses on the deployment of a device via a minimally invasive fashion and by way of example considers a minimally invasive surgical procedure utilizing the intercostal or subxyphoid space for valve introduction, but may also include standard retrograde, or antegrade transcatheter approaches. In order to accomplish this, the valve is formed in such a manner that it can be compressed to fit within a delivery system and secondarily ejected from the delivery system into the target location, for example the mitral or tricuspid valve annulus.

Stent-in-a-Stent Structures & Variations

In a preferred embodiment, there is provided a pre-configured compressible transcatheter prosthetic cardiovascular valve having an improved stent-in-a-stent sealing design, which comprises an expandable leaflet assembly comprised of stabilized tissue or synthetic material, said leaflet assembly disposed within an expandable inner stent having an articulating collar structure at its distal end and a tether apparatus attached to its proximal end, said inner stent being partially or wholly disposed within an outer stent.

In a preferred embodiment, the diameter of the inner stent is about 24 mm and the outer stent is oval having a short diameter of about 24 mm and a long diameter of about 32 mm. It is noted that valves according to the present invention may be sized appropriate to a specific patient or patient population and the above non-limiting example is shown as one possible preferred embodiment.

In another preferred embodiment, the collar has a circular diameter of about 32-37 mm, or has a elliptical diameter of about 24×32 mm, or has a D-shaped collar to avoid LVOT. In is contemplated as within the scope of the invention that that collar may be attached or operatively associated with both the inner stent and the outer stent, providing a somewhat toroidal cover having a valve thru-hole leading to the inside of the inner stent and the leaflet assembly.

In another preferred embodiment, there is provided a prosthetic heart valve as described having a single tether connecting the proximal end of the stent to an epicardial securing device at or near the apex of the left ventricle. In another preferred embodiment, the prosthetic mitral valve does not use an anchoring or positioning tether at all, and instead is held in the mitral annulus by the wrapping forces of the native leaflets, and optionally one or more standard anchoring elements, including but not limited to barbs, pins, and/or hooks, or combinations thereof.

In another preferred embodiment, there is provided a prosthetic heart valve as described wherein the outer stent comprises a nitinol stent body having a covering of stabilized tissue or synthetic material attached to the outer stent body, wherein during systole the leaflet assembly closes and the area between the covered inner stent and the covered outer stent is filled by retrograde hemodynamic forces to form sub-valvular sealing partitions.

In another preferred embodiment, there is provided a prosthetic cardiovascular valve with a stent body that has a low height to width profile.

In a preferred embodiment, the prosthetic mitral valve contains an improved stent body that is a half-round D-shape in cross-section.

In a preferred embodiment, the prosthetic mitral valve contains an improved stent body that is a bent tubular stent structure wherein the bend is directed away from the anterior leaflet, away from interfering with coaptation of adjacent, e.g. aortic, valvular leaflets.

In a preferred embodiment, the prosthetic mitral valve contains an improved stent body that has a low height to width profile and the leaflet structure disposed within the stent is positioned at or near the atrial end of the stent body.

In another preferred embodiment, the a prosthetic mitral valve has a stent body made from both braided wire (atrial end) and laser-cut metal (annular or ventricular end), or vice versa.

Additional Features for Improved Stents

In a preferred embodiment, the prosthetic heart valve has a cuff that has articulating wire articulating radial tines or posts of wire of various lengths.

In another preferred embodiment, the prosthetic heart valve has at least one elastic tether to provide compliance during the physiologic movement or conformational changes associated with heart contraction.

In another preferred embodiment, the prosthetic heart valve has a stent body and cuff that are made from a superelastic metal.

In another preferred embodiment, the prosthetic heart valve has a tether which is used to position the valve cuff into the mitral annulus to prevent perivalvular leak.

In another preferred embodiment, the tethers are bioabsorbable and provide temporary anchoring until biological fixation of the prosthesis occurs. Biological fixation consisting of fibrous adhesions between the leaflet tissues and prosthesis or compression on the prosthesis by reversal of heart dilation, or both.

In another preferred embodiment, the prosthetic heart valve has a cuff for a prosthetic heart valve, said cuff being covered with tissue.

In another preferred embodiment, the cuff is covered with a synthetic polymer selected from expandable polytetrafluoroethylene (ePTFE) or polyester.

In another preferred embodiment, there is provided a prosthetic heart valve that has leaflet material constructed from a material selected from the group consisting of polyurethane, polytetrafluoroethylene, pericardium, and small intestine submucosa.

In another preferred embodiment, there is provided a prosthetic heart valve having surfaces that are treated with anticoagulant.

In another preferred embodiment, there is provided a prosthetic heart valve having a cuff and containing anchoring tethers which are attached to the cuff.

In another preferred embodiment, there is provided a prosthetic heart valve having a cuff and containing anchoring tethers which are attached to the cuff and at both commissural tips.

In another preferred embodiment, there is provided a prosthetic heart valve having a cuff where the cuff attachment relative to the body is within the angles of about 60 degrees to about 150 degrees.

In another preferred embodiment, there is provided a prosthetic heart valve containing a combination of tethers and barbs useful for anchoring the device into the mitral annulus.

In another embodiment, the wire of the cuff is formed as a series of radially extending articulating radial tines or posts of wire of equal or variable length.

In another embodiment, the cuff extends laterally beyond the expanded tubular stent according to a ratio of the relationship between the height of the expanded deployed stent (h) and the lateral distance that the cuff extends onto the tissue (1). Preferably, the h/1 ratio can range from 1:10 to 10:1, and more preferably includes without limitation 1:3, 1:2, 1:1, 2:1, and fractional ranges there between such as 1.25:2.0, 1.5:2.0, and so forth. It is contemplated in one non-limiting example that the cuff can extend laterally (1) between about 3 and about 30 millimeters.

In another embodiment, there is provided a feature wherein the tubular stent has a first end and a second end, wherein the cuff is formed from the stent itself, or in the alternative is formed separately and wherein the cuff is located at the first end of the stent, and the second end of the tubular stent has a plurality of tether attachment structures.

In another embodiment, there is provided a feature further comprising a plurality of tethers for anchoring the prosthetic heart valve to tissue and/or for positioning the prosthetic heart valve.

In another embodiment, there is provided a feature further comprising an epicardial tether securing device, wherein the tethers extend from about 2 cm to about 20 cm in length, and are fastened to an epicardial tether securing device. Some pathological conditions within a ventricle may require a atrial-apical tether from about 8 to about 15 cm, or more as described within the range above.

In another embodiment, there is provided a catheter delivery system for delivery of a prosthetic heart valve which comprises a delivery catheter having the prosthetic heart valve disposed therein, and an obturator for expelling the prosthetic heart valve.

In another embodiment, there is provided an assembly kit for preparing the catheter delivery system which comprises a compression funnel, an introducer, a wire snare, an obturator, a delivery catheter, and a prosthetic heart valve, wherein the compression funnel has an aperture for attaching to the introducer, wherein said introducer is comprised of a tube having a diameter that fits within the diameter of the delivery catheter, wherein said obturator is comprised of a tube fitted with a handle at one end and a cap at the other end, wherein said cap has an opening to allow the wire snare to travel therethrough, and said obturator has a diameter that fits within the diameter of the introducer, and wherein said prosthetic heart valve is compressible and fits within the delivery catheter.

In another embodiment, there is provided a method of treating mitral regurgitation and/or tricuspid regurgitation in a patient, which comprises the step of surgically deploying the prosthetic heart valve described herein into the annulus of the target valve structure, e.g. mitral valve annulus and tricuspid valve annulus of the patient.

In another embodiment, there is provided a feature wherein the prosthetic heart valve is deployed by directly accessing the heart through an intercostal space, using an apical approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through a thoracotomy, sternotomy, or minimally-invasive thoracic, thoroscopic, or transdiaphragmatic approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through the intercostal space, using a lateral approach to enter the left or right ventricle, and deploying the prosthetic heart valve into the valvular annulus using the catheter delivery system.

In another embodiment, there is provided a feature wherein the prosthetic heart valve is deployed by accessing the left heart using either an antegrade-trans(atrial)septal (transvenous-trans(atrial)septal) approach or a retrograde (transarterial-transaortic) catheter approach to enter the left heart, and deploying the prosthetic heart valve into the mitral annulus using the catheter delivery system.

In another embodiment, there is provided a feature wherein the prosthetic heart valve is deployed into the mitral annulus from a retrograde approach by accessing the left ventricle through the apex of the ventricular septum (transvenous-trans(ventricular)septal approach).

In another embodiment, there is a feature wherein the prosthetic heart valve is deployed into the mitral position using a retrograde transventricular septal approach and the tethers are anchored into or on the right ventricular side of the ventricular septum.

In another embodiment, there is provided a feature further comprising tethering the prosthetic heart valve to tissue within the left ventricle.

In another embodiment, there is provided a feature wherein the prosthetic heart valve is tethered to the apex of the left ventricle using an epicardial tether securing device.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment.

Articulating Collar Support Structures with Collar Variations

In another preferred embodiment, there is provided a method of sealing a deployed prosthetic mitral valve against hemodynamic leaking, comprising fitting a prosthetic mitral valve with a flared end or cuff having articulating collar support structures prior to deployment wherein the flared end or cuff is constructed to contour to the commissures of a pathologically defective mitral valve and constructed to contour to the zone of coaptation of the pathologically defective mitral valve, wherein the flared end or cuff is formed from wire originating from one end of an expandable tubular braided wire stent and the flared end or cuff is covered with stabilized tissue or synthetic material, the commissural contour components of the flared end or cuff and the zone of coaptation contour components of the flared end or cuff forming a complete or partial saddle-shape wherein the commissural contour components are in direct communication with the mitral valve commissures, and the zone of coaptation contour components are in direct communication with the mitral valve zone of coaptation.

In a preferred embodiment, the flared end or cuff shape is agaricoid.

In another preferred embodiment, the flared end or cuff shape is onychoid.

In another preferred embodiment, the flared end or cuff shape is reniform.

In another preferred embodiment, the flared end or cuff shape is an oval.

In another preferred embodiment, the flared end or cuff shape is a truncated-oval having a squared end.

In another preferred embodiment, the flared end or cuff shape is propeller-shaped having two or three blades.

In another preferred embodiment, the flared end or cuff shape is cruciform.

In another preferred embodiment, the flared end or cuff shape is petal-shaped having flat radial covered articulating radial tines or posts of wire.

In another preferred embodiment, the flared end or cuff shape is irregular or amoeboid.

In another preferred embodiment, the flared end or cuff shape is cotyloid shaped.

In another preferred embodiment, the flared end or cuff shape is a partial half-round fan-shape.

In another preferred embodiment, the flared end or cuff shape is a rectangular U-shape.

In another preferred embodiment, the flared end or cuff is constructed from ductile metal.

In another preferred embodiment, the flared end or cuff shape is constructed with a cover of stabilized tissue that is derived from adult, or 90-day old, or 30 day old bovine, ovine, equine or porcine pericardium, or from animal small intestine submucosa.

In another preferred embodiment, the flared end or cuff shape is constructed with a cover of synthetic material is selected from the group consisting of polyester, polyurethane, and polytetrafluoroethylene.

In another preferred embodiment, the stabilized tissue or synthetic material is treated with anticoagulant.

In another preferred embodiment, the method further comprises the step of anchoring the prosthetic heart valve to tissue uses a plurality of tethers to the flared end or cuff.

In another preferred embodiment, the method further comprises the step of anchoring the prosthetic heart valve to tissue using a single tether attached to the stent or a tether-attachment structure attached to the stent.

In another preferred embodiment, at least one of the plurality of tethers is an elastic tether.

In another preferred embodiment, at least one of the plurality of tethers is a bioresorbable tether.

Trapdoor Sealing Device

In a preferred embodiment, there is provided a preconfigured compressible transcatheter prosthetic cardiovascular valve having an improved commissural sealing component, which comprises an expandable leaflet assembly comprised of stabilized tissue or synthetic material, said leaflet assembly disposed within an expandable stent having a flared distal end comprised of a plurality of articulating collar support structures having a tissue covering, said expandable stent having a proximal end comprised of an integral tether connection apparatus, said commissural sealing component comprising a wire-frame reinforced skirt of stabilized tissue or synthetic material, said wireframe attached to a proximal surface of the collar, wherein during systole the leaflet assembly closes and the wire-frame reinforced skirt forms a commissural sealing canopy that is filled to form a commissural subvalvular seal by retrograde hemodynamic forces.

The design as provided focuses on the deployment of a device via a minimally invasive fashion and by way of example considers a minimally invasive surgical procedure utilizing the intercostal or subxyphoid space for valve introduction, but may also include standard retrograde, or antegrade transcatheter approaches. In order to accomplish this, the valve is formed in such a manner that it can be compressed to fit within a delivery system and secondarily ejected from the delivery system into the target location, for example the mitral or tricuspid valve annulus.

Wire-Frame Commissural Sealing Structure with Stent Variations

In a preferred embodiment, there is provided a prosthetic mitral valve containing an expandable leaflet assembly comprised of stabilized tissue or synthetic material disposed within a self-expanding stent having a flared collar at its distal end and a wire-frame reinforced commissural sealing structure attached under the collar and forming a commissural sealing canopy.

In another preferred embodiment, there is provided a prosthetic heart valve as described having a single tether connecting the proximal end of the stent to an epicardial securing device at or near the apex of the left ventricle. In another preferred embodiment, the prosthetic mitral valve does not use an anchoring or positioning tether at all, and instead is held in the mitral annulus by the wrapping forces of the native leaflets, and optionally one or more standard anchoring elements, including but not limited to barbs, pins, and/or hooks, or combinations thereof.

In another preferred embodiment, there is provided a prosthetic heart valve as described, wherein the wire-frame commissural sealing component comprises a ring of tissue or synthetic material stretched between at least two wire-frame elements, said tissue/material and said wire-frame attached to and hanging below the collar, wherein the commissural sealing component has a sub-annular shape in an oval, with a short diameter from posterior-to-anterior about the same diameter as the stent body, about 24 mm, and a long diameter from commissure-to-commissure of about 32 mm. These dimensions will necessarily vary depending on patient needs, and are given only as non-limiting examples based upon anatomical averages.

In a preferred embodiment, the wire-frame structure is a shape memory device and is formed to fold flat during compression of the valve and to expand and create the commissural canopy upon opening and deployment.

In another preferred embodiment, there is provided a prosthetic cardiovascular valve with a stent body that has a low height to width profile.

In a preferred embodiment, the prosthetic mitral valve contains an improved stent body that is a half-round D-shape in cross-section.

In a preferred embodiment, the prosthetic mitral valve contains an improved stent body that is a bent tubular stent structure wherein the bend is directed away from the anterior leaflet, away from interfering with coaptation of adjacent, e.g. aortic, valvular leaflets.

In a preferred embodiment, the prosthetic mitral valve contains an improved stent body that has a low height to width profile and the leaflet structure disposed within the stent is positioned at or near the atrial end of the stent body.

In another preferred embodiment, the a prosthetic mitral valve has a stent body made from both braided wire (atrial end) and laser-cut metal (annular or ventricular end), or vice versa.

Additional Features for Improved Stents

In a preferred embodiment, the prosthetic heart valve has a cuff that has articulating wire articulating radial tines or posts of wire of various lengths.

In another preferred embodiment, the prosthetic heart valve has at least one elastic tether to provide compliance during the physiologic movement or conformational changes associated with heart contraction.

In another preferred embodiment, the prosthetic heart valve has a stent body and cuff that are made from a superelastic metal.

In another preferred embodiment, the prosthetic heart valve has a tether which is used to position the valve cuff into the mitral annulus to prevent perivalvular leak.

In another preferred embodiment, the tethers are bioabsorbable and provide temporary anchoring until biological fixation of the prosthesis occurs. Biological fixation consisting of fibrous adhesions between the leaflet tissues and prosthesis or compression on the prosthesis by reversal of heart dilation, or both.

In another preferred embodiment, the prosthetic heart valve has a cuff for a prosthetic heart valve, said cuff being covered with tissue.

In another preferred embodiment, the cuff is covered with a synthetic polymer selected from expandable polytetrafluoroethylene (ePTFE) or polyester.

In another preferred embodiment, there is provided a prosthetic heart valve that has leaflet material constructed from a material selected from the group consisting of polyurethane, polytetrafluoroethylene, pericardium, and small intestine submucosa.

In another preferred embodiment, there is provided a prosthetic heart valve having surfaces that are treated with anticoagulant.

In another preferred embodiment, there is provided a prosthetic heart valve having a cuff and containing anchoring tethers which are attached to the cuff.

In another preferred embodiment, there is provided a prosthetic heart valve having a cuff and containing anchoring tethers which are attached to the cuff and at both commissural tips.

In another preferred embodiment, there is provided a prosthetic heart valve having a cuff where the cuff attachment relative to the body is within the angles of about 60 degrees to about 150 degrees.

In another preferred embodiment, there is provided a prosthetic heart valve containing a combination of tethers and barbs useful for anchoring the device into the mitral annulus.

In another embodiment, the wire of the cuff is formed as a series of radially extending articulating radial tines or posts of wire of equal or variable length.

In another embodiment, the cuff extends laterally beyond the expanded tubular stent according to a ratio of the relationship between the height of the expanded deployed stent (h) and the lateral distance that the cuff extends onto the tissue (1). Preferably, the h/1 ratio can range from 1:10 to 10:1, and more preferably includes without limitation 1:3, 1:2, 1:1, 2:1, and fractional ranges there between such as 1.25:2.0, 1.5:2.0, and so forth. It is contemplated in one non-limiting example that the cuff can extend laterally (1) between about 3 and about 30 millimeters.

In another embodiment, there is provided a feature wherein the tubular stent has a first end and a second end, wherein the cuff is formed from the stent itself, or in the alternative is formed separately and wherein the cuff is located at the first end of the stent, and the second end of the tubular stent has a plurality of tether attachment structures.

In another embodiment, there is provided a feature further comprising a plurality of tethers for anchoring the prosthetic heart valve to tissue and/or for positioning the prosthetic heart valve.

In another embodiment, there is provided a feature further comprising an epicardial tether securing device, wherein the tethers extend from about 2 cm to about 20 cm in length, and are fastened to an epicardial tether securing device. Some pathological conditions within a ventricle may require a atrial-apical tether from about 8 to about 15 cm, or more as described within the range above.

In another embodiment, there is provided a catheter delivery system for delivery of a prosthetic heart valve which comprises a delivery catheter having the prosthetic heart valve disposed therein, and an obturator for expelling the prosthetic heart valve.

In another embodiment, there is provided an assembly kit for preparing the catheter delivery system which comprises a compression funnel, an introducer, a wire snare, an obturator, a delivery catheter, and a prosthetic heart valve, wherein the compression funnel has an aperture for attaching to the introducer, wherein said introducer is comprised of a tube having a diameter that fits within the diameter of the delivery catheter, wherein said obturator is comprised of a tube fitted with a handle at one end and a cap at the other end, wherein said cap has an opening to allow the wire snare to travel therethrough, and said obturator has a diameter that fits within the diameter of the introducer, and wherein said prosthetic heart valve is compressible and fits within the delivery catheter.

In another embodiment, there is provided a method of treating mitral regurgitation and/or tricuspid regurgitation in a patient, which comprises the step of surgically deploying the prosthetic heart valve described herein into the annulus of the target valve structure, e.g. mitral valve annulus and tricuspid valve annulus of the patient.

In another embodiment, there is provided a feature wherein the prosthetic heart valve is deployed by directly accessing the heart through an intercostal space, using an apical approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through a thoracotomy, sternotomy, or minimally-invasive thoracic, thoracoscopic, or transdiaphragmatic approach to enter the left (or right) ventricle, and deploying the prosthetic heart valve into the valvular annulus using the catheter delivery system.

In another embodiment, there is provided a feature wherein the prosthetic heart valve is deployed by directly accessing the heart through the intercostal space, using a lateral approach to enter the left or right ventricle, and deploying the prosthetic heart valve into the valvular annulus using the catheter delivery system.

In another embodiment, there is provided a feature wherein the prosthetic heart valve is deployed by accessing the left heart using either an antegrade-trans(atrial)septal (transvenous-trans(atrial)septal) approach or a retrograde (transarterial-transaortic) catheter approach to enter the left heart, and deploying the prosthetic heart valve into the mitral annulus using the catheter delivery system.

In another embodiment, there is provided a feature wherein the prosthetic heart valve is deployed into the mitral annulus from a retrograde approach by accessing the left ventricle through the apex of the ventricular septum (transvenous-trans(ventricular)septal approach).

In another embodiment, there is a feature wherein the prosthetic heart valve is deployed into the mitral position using a retrograde transventricular septal approach and the tethers are anchored into or on the right ventricular side of the ventricular septum.

In another embodiment, there is provided a feature further comprising tethering the prosthetic heart valve to tissue within the left ventricle.

In another embodiment, there is provided a feature wherein the prosthetic heart valve is tethered to the apex of the left ventricle using an epicardial tether securing device.

In another embodiment, there is provided a retrieval method for quickly removing a prosthetic heart valve having one or more tethers from a patient using minimally invasive cardiac catheter techniques, which comprises the steps of, capturing the one or more tethers with a catheter having a snare attachment, guiding the captured tethers into a collapsible funnel attachment connected to the removal catheter, pulling the tethers to conform the prosthetic heart valve into a collapsed, compressed conformation, and pulling the now compressed prosthetic heart valve into the removal catheter for subsequent extraction. The retrieval method is contemplated for use for capturing the prosthetic heart valve as described herein or any suitable tethered, collapsible medical device. In a preferred embodiment, the method is used to extract a prosthetic heart valve from either the left or right ventricle. The method may be particularly useful to extract the prosthetic appliance during an aborted surgical deployment.

Articulating Collar Support Structures with Collar Variations

In another preferred embodiment, there is provided a method of sealing a deployed prosthetic mitral valve against hemodynamic leaking, comprising fitting a prosthetic mitral valve with a flared end or cuff having articulating collar support structures prior to deployment wherein the flared end or cuff is constructed to contour to the commissures of a pathologically defective mitral valve and constructed to contour to the zone of coaptation of the pathologically defective mitral valve, wherein the flared end or cuff is formed from wire originating from one end of an expandable tubular braided wire stent and the flared end or cuff is covered with stabilized tissue or synthetic material, the commissural contour components of the flared end or cuff and the zone of coaptation contour components of the flared end or cuff forming a complete or partial saddle-shape wherein the commissural contour components are in direct communication with the mitral valve commissures, and the zone of coaptation contour components are in direct communication with the mitral valve zone of coaptation.

In a preferred embodiment, the flared end or cuff shape is agaricoid.

In another preferred embodiment, the flared end or cuff shape is onychoid.

In another preferred embodiment, the flared end or cuff shape is reniform.

In another preferred embodiment, the flared end or cuff shape is an oval.

In another preferred embodiment, the flared end or cuff shape is a truncated-oval having a squared end.

In another preferred embodiment, the flared end or cuff shape is propeller-shaped having two or three blades.

In another preferred embodiment, the flared end or cuff shape is cruciform.

In another preferred embodiment, the flared end or cuff shape is petal-shaped having flat radial covered articulating radial tines or posts of wire.

In another preferred embodiment, the flared end or cuff shape is irregular or amoeboid.

In another preferred embodiment, the flared end or cuff shape is cotyloid shaped.

In another preferred embodiment, the flared end or cuff shape is a partial half-round fan-shape.

In another preferred embodiment, the flared end or cuff shape is a rectangular U-shape.

In another preferred embodiment, the flared end or cuff is constructed from ductile metal.

In another preferred embodiment, the flared end or cuff shape is constructed with a cover of stabilized tissue that is derived from adult, or 90-day old, or 30 day old bovine, ovine, equine or porcine pericardium, or from animal small intestine submucosa.

In another preferred embodiment, the flared end or cuff shape is constructed with a cover of synthetic material is selected from the group consisting of polyester, polyurethane, and polytetrafluoroethylene.

In another preferred embodiment, the stabilized tissue or synthetic material is treated with anticoagulant.

In another preferred embodiment, the method further comprises the step of anchoring the prosthetic heart valve to tissue uses a plurality of tethers to the flared end or cuff.

In another preferred embodiment, the method further comprises the step of anchoring the prosthetic heart valve to tissue using a single tether attached to the stent or a tether-attachment structure attached to the stent.

In another preferred embodiment, at least one of the plurality of tethers is an elastic tether.

In another preferred embodiment, at least one of the plurality of tethers is a bioresorbable tether.

BRIEF DESCRIPTION OF THE DRAWINGS

The attached figures provide enabling and non-limiting example of certain features of the present invention. The figures are not intended to be limiting in any way to limit the description that is provided in the text.

Bulletnose Retrieval Device

Sealing Canopy

Figure 14:
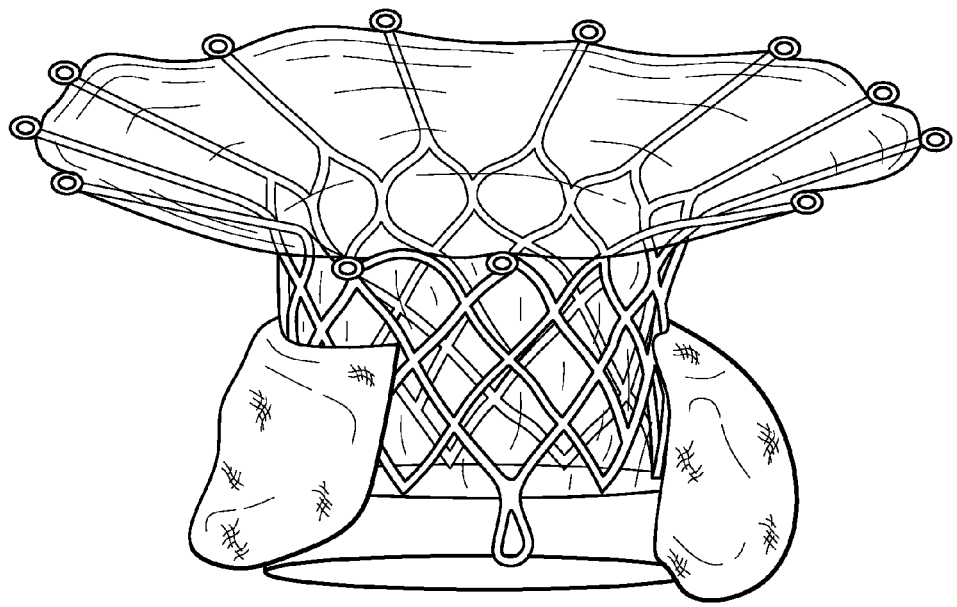

FIG. 14 is a perspective view of one laser cut stent embodiment showing the articulating collar support structures of the flared end of the tubular stent and passively oscillating dome-shaped sealing canopy attached to the wire halo and the stent body, in cut-away view, with arrows indicating hemodynamic flow into the space between the wire halo and the proximal end of the stent, thus filling the canopy. Note this figure does not illustrate the final valve product as it has neither the surface coatings, e.g. synthetic material and/or stabilized tissue, nor internal leaflet structures have been added.

Figure 15:
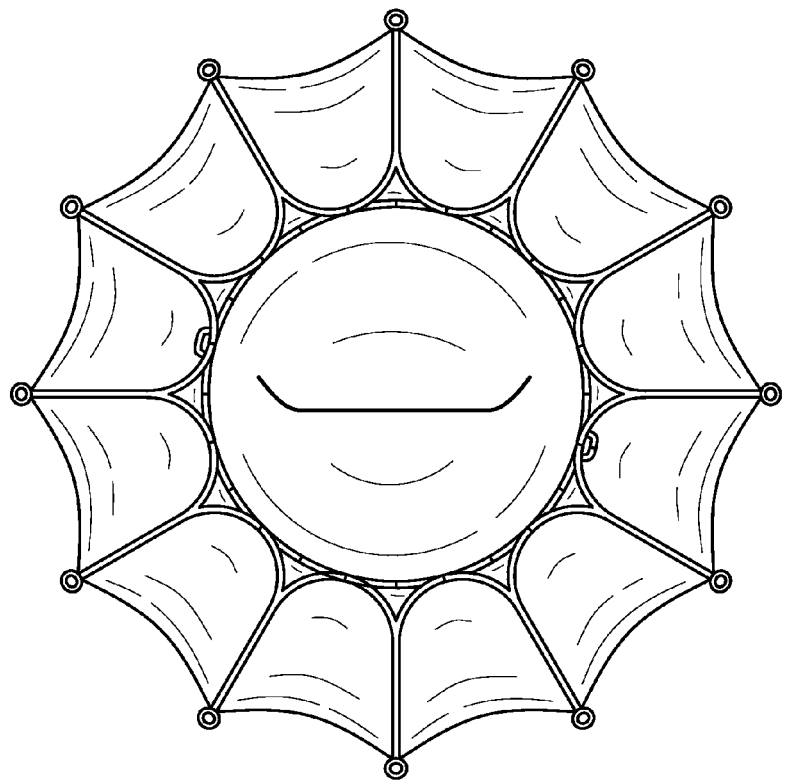

FIG. 15 is a top view of one embodiment showing the articulating collar support structures of the flared end of the tubular stent and valve leaflets disposed therein. Note this figure does not illustrate the final valve product as it has neither the surface coatings, e.g. synthetic material and/or stabilized tissue, etc. have been added.

Figure 16:
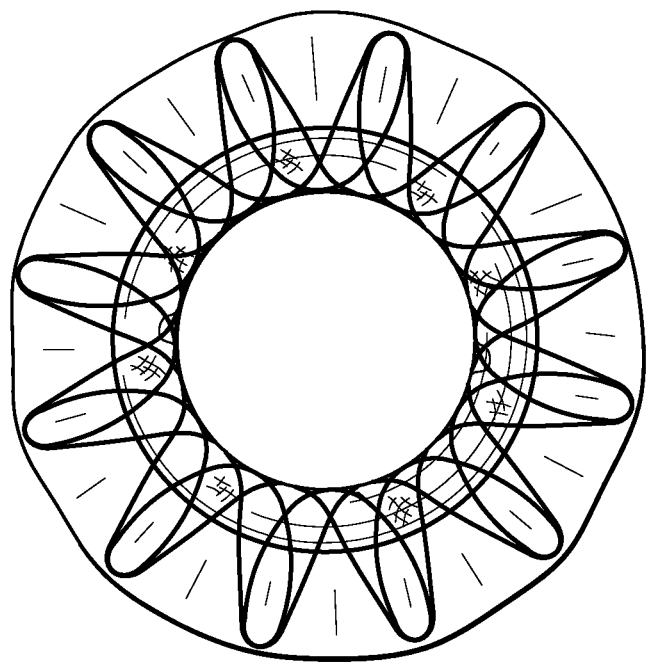

FIG. 16 is a top view of one embodiment showing the braided wire collar support structures of the flared end of the tubular stent and valve leaflets disposed therein. Note this figure does not illustrate the final valve product as it has neither the surface coatings, e.g. synthetic material and/or stabilized tissue, etc. have been added.

Figure 17:
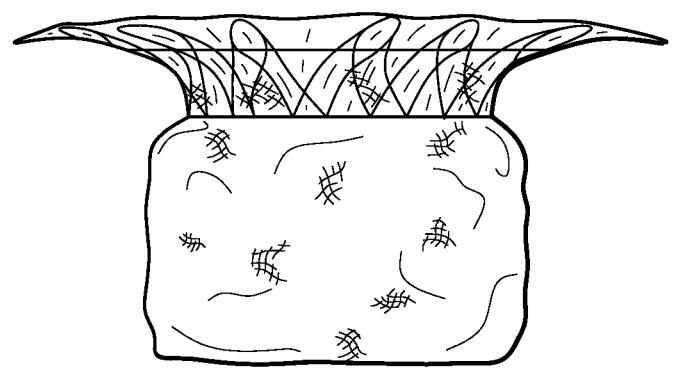

FIG. 17 is a side view of one braided embodiment showing the braided wire collar support structures of the flared end of the tubular stent and passively oscillating dome-shaped sealing canopy attached to the wire halo and the stent body, in cut-away view to show tether attachments. Note this figure does not illustrate the final valve product as it has neither the surface coatings, e.g. synthetic material and/or stabilized tissue, nor internal leaflet structures have been added.

Figure 18:
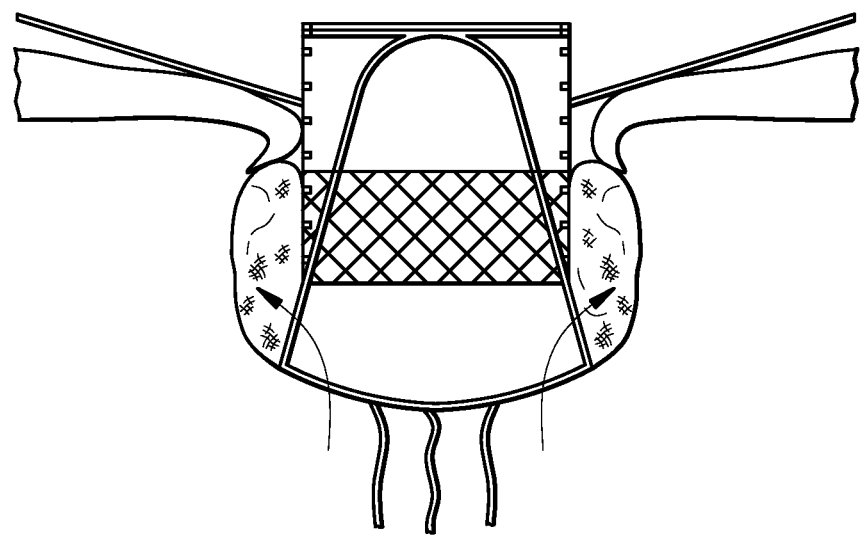

FIG. 18 is an illustration of a side view with false-transparent detail of the native mitral leaflet structure having the prosthetic valve of the present invention deployed therein (shown without apical tether attached). FIG. 18 shows how a prosthetic valve may inadvertently leave space for regurgitative leaking FIG. 18 also shows passively oscillating dome-shaped sealing canopy in a hemodynamically filled state, and consequently creating a periannular sealing structure outside of the stent body to stop regurgitative leaking FIG. 18 also shows arrows indicating hemodynamic flow into the space between the wire halo and the proximal end of the stent, thus filling the canopy.

Figure 19:
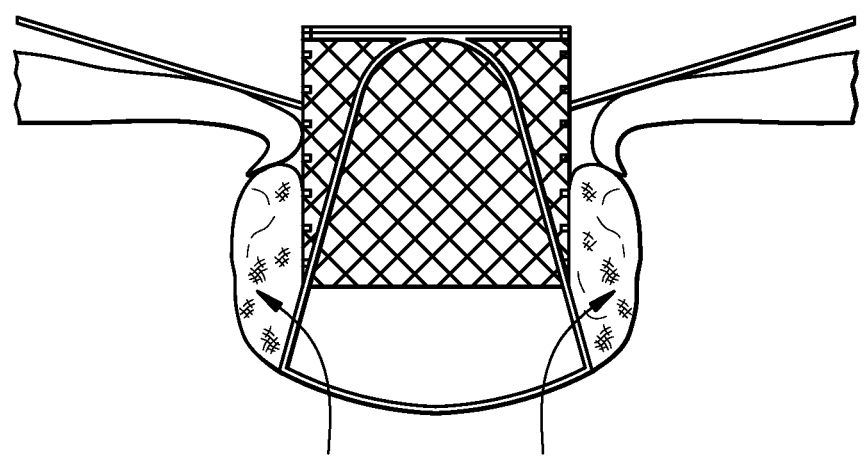

FIG. 19 is an illustration of a side view with false-transparent detail of the native left atrium, left ventricle, and mitral leaflet structure having the prosthetic valve of the present invention deployed therein (shown with apical tether attached). FIG. 19 shows how the passively oscillating dome-shaped sealing canopy of the present invention, in a hemodynamically filled state, creates a periannular sealing structure outside of the stent body to stop regurgitative leaking FIG. 19 also shows arrows indicating ventricular contraction, arrows indicating hemodynamic flow into the space between the wire halo and the proximal end of the stent, thus filling the canopy. FIG. 19 also shows arrows indicating that periannular leaking is stopped.

Figure 20:
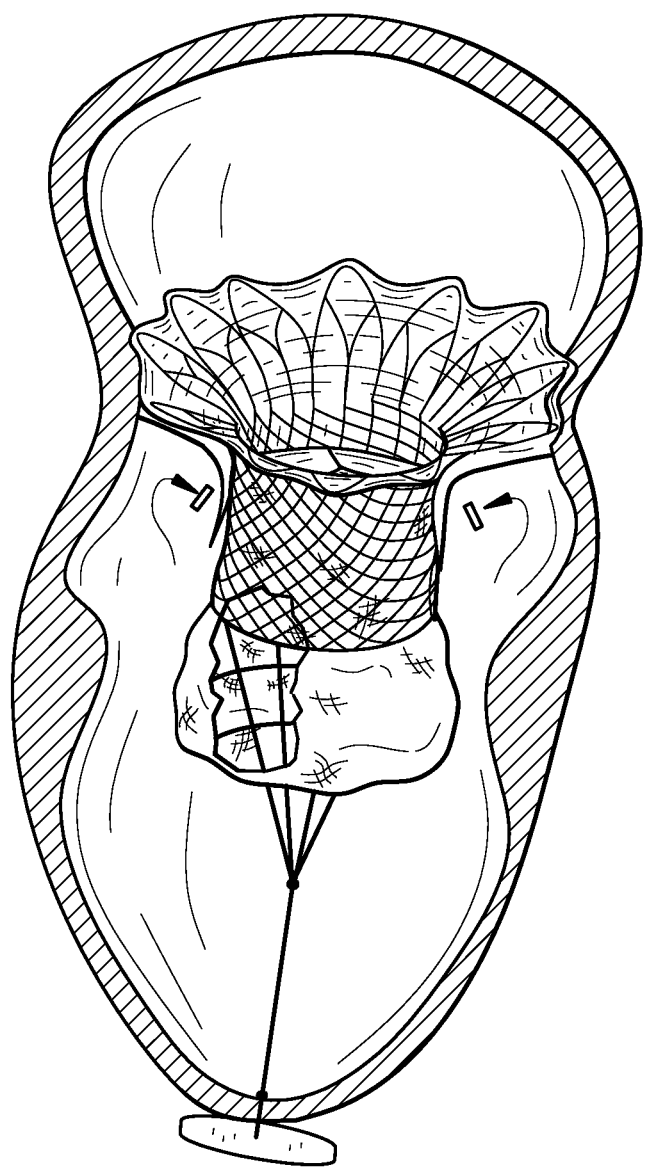

FIG. 20 is an illustration of a prosthetic heart valve of the present inventive subject matter, wherein the valve does not use an anchoring tether or a positioning tether at all, and instead is held in the mitral annulus by the wrapping forces of the native leaflets, and optionally one or more standard anchoring elements, including but not limited to barbs, pins, and/or hooks, or combinations thereof.

Figure 21:
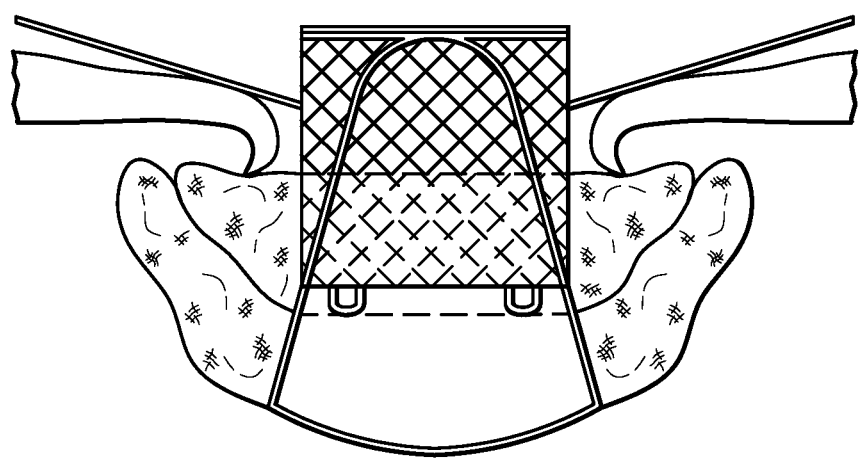

FIG. 21 is an illustration of a prosthetic heart valve of the present inventive subject matter wherein the peri-annular sealing component comprises two or more passively oscillating dome-shaped sealing canopies, each comprised of a skirt of stabilized tissue or synthetic material attached on a distal edge of said material at or near the distal end of the stent and attached at a proximal edge to the wire halo apparatus, wherein during systole the leaflet assembly closes and each of the sealing canopies is filled to form multiple redundant periannular seal partitions by retrograde hemodynamic forces.

Figure 22:
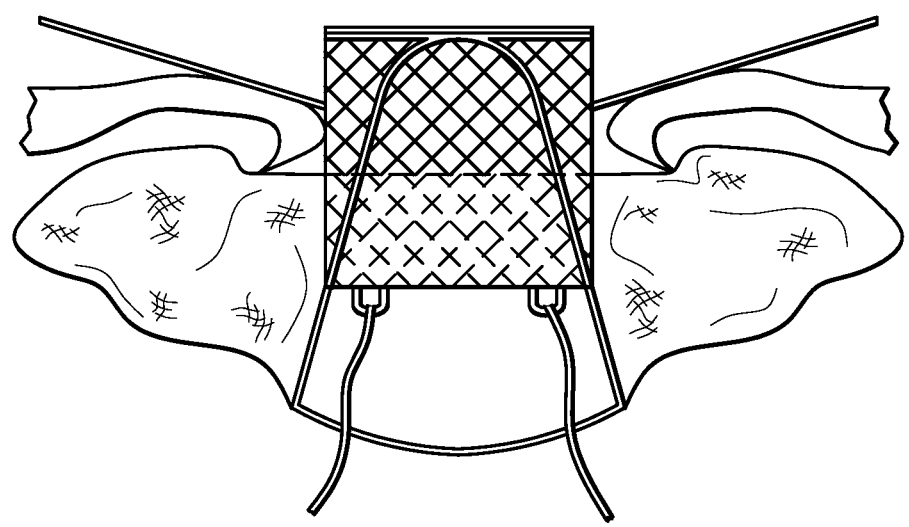

FIG. 22 is an illustration of a prosthetic heart valve of the present inventive subject matter wherein the peri-annular sealing component comprises an enlarged passively oscillating dome-shaped sealing canopy that has a sub-annular diameter about the same diameter as the atrial collar.

Figure 23:
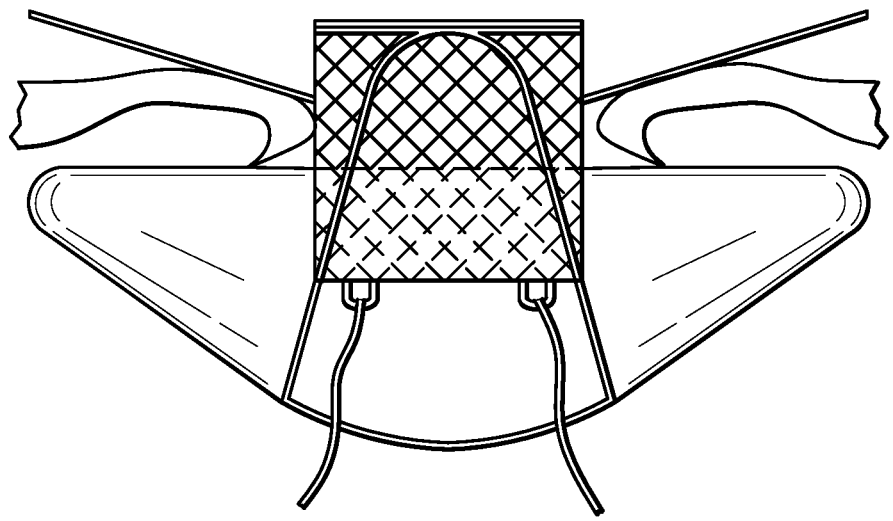

FIG. 23 is an illustration of a prosthetic heart valve of the present inventive subject matter wherein the peri-annular sealing component comprises an enlarged gel-filled sealing chamber that has a sub-annular diameter about the same diameter as the atrial collar and which is attached to the wire halo on the ventricular side and to the stent body on the periannular side.

Figure 24:
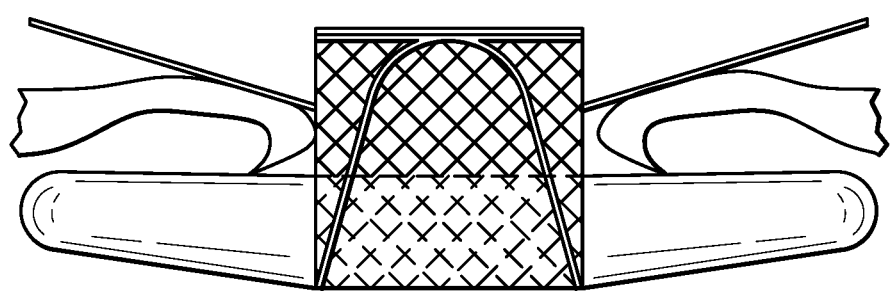

FIG. 24 is an illustration of a prosthetic heart valve of the present inventive subject matter wherein the peri-annular sealing component comprises an enlarged gel-filled sealing chamber that has a sub-annular diameter about the same diameter as the atrial collar and which is attached to the proximal end of the stent body on the ventricular side and to a mid-line section of the stent body on the periannular side.

Figure 25:
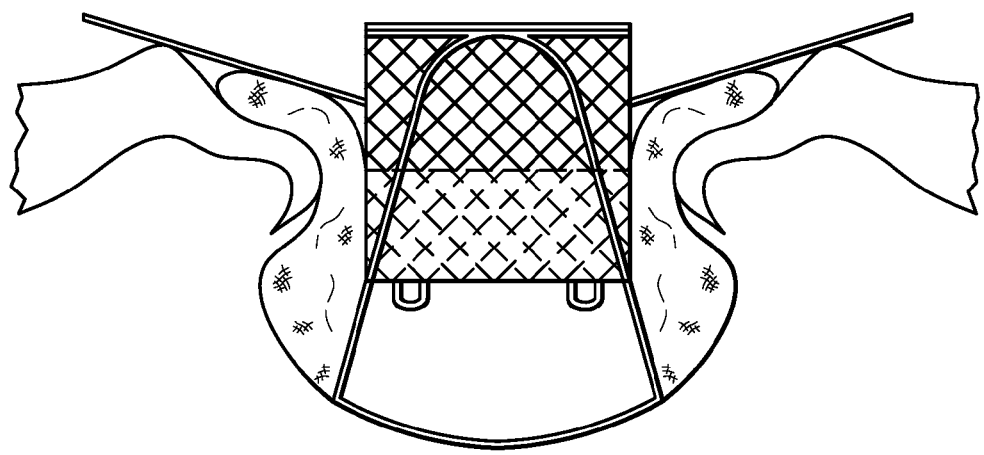

FIG. 25 is an illustration of a prosthetic heart valve of the present inventive subject matter wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a supra-annular seal partition by retrograde hemodynamic forces.

Figure 26:
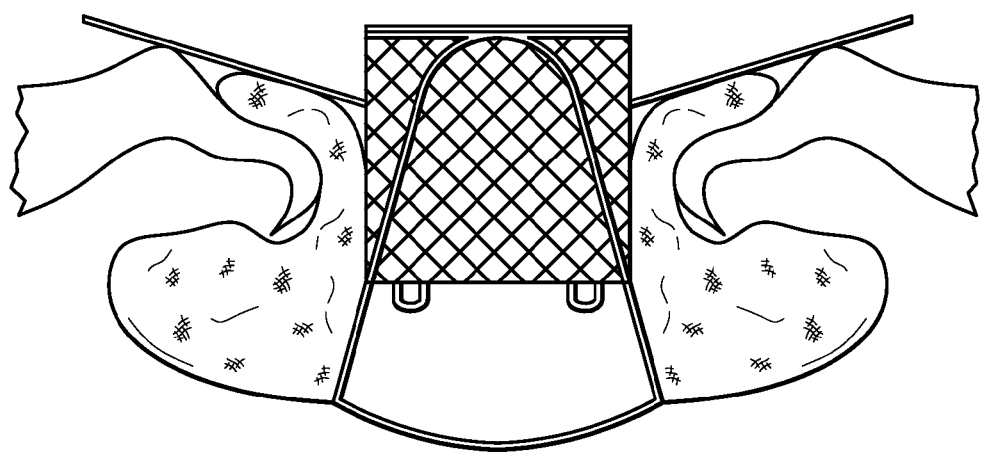

FIG. 26 is an illustration of a prosthetic heart valve of the present inventive subject matter wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a combined sub-annular and supra-annular seal partition by retrograde hemodynamic forces.

Stent-in-a-Stent

Figure 27:
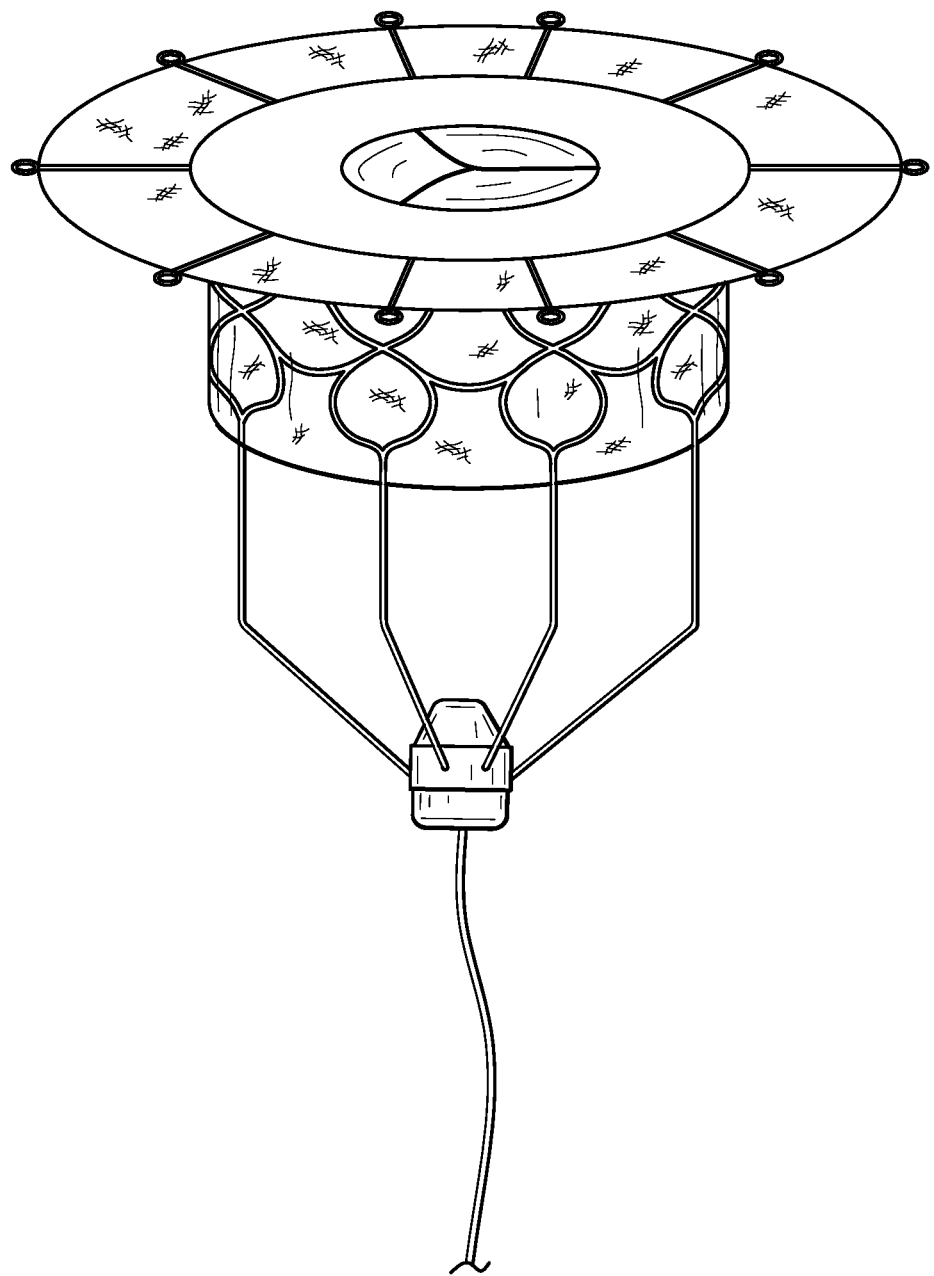

FIG. 27 is a perspective view of one laser cut stent embodiment showing the articulating collar having a valve leaflet thru-hole and attached to both the inner and outer stents creating a sub-valvular chamber. FIG. 27 also shows intermediate tethers attached to the base or proximal end of the outer stent and joining at a junction nut with a single anchoring (or positioning) tether extending away toward the epicardial anchor (not shown).

Figure 28:
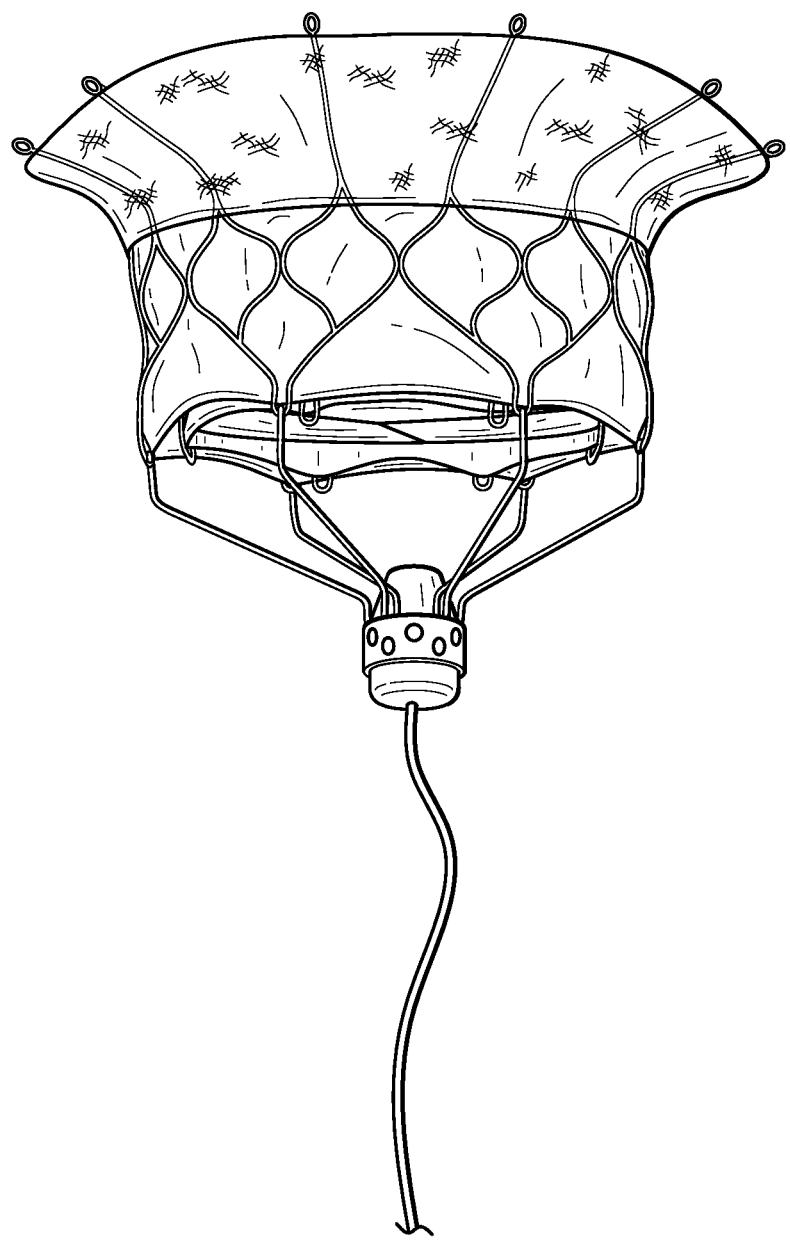

FIG. 28 is a lower perspective view of one embodiment showing the underside of the atrial sealing collar, the low height profile outer stent (and inner stent), the intermediate wire tethers attached at the junction and the single tether extending away. FIG. 21 also shows a leaflet assembly located in the lower section of the inner stent and the outer stent and its covering creating a chamber to assist sealing.

Figure 29:
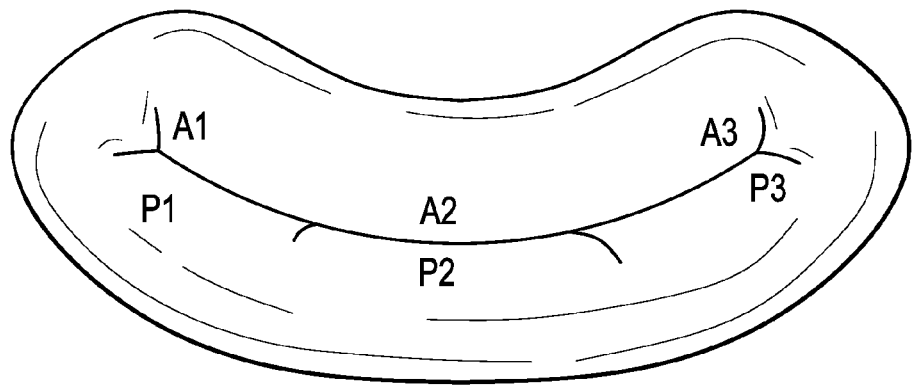

FIG. 29 is a top view of mitral valve anatomy showing anterior and posterior segments (scallops) of the mitral valve.

Figure 30:

FIG. 30 is a top view of mitral valve anatomy having a traditional prosthetic valve deployed therein and causing spreading of the A1-P1 and A3-P3 segments, which will result in hemodynamic leakage at the commissural edges of the mitral valve.

Figure 31:
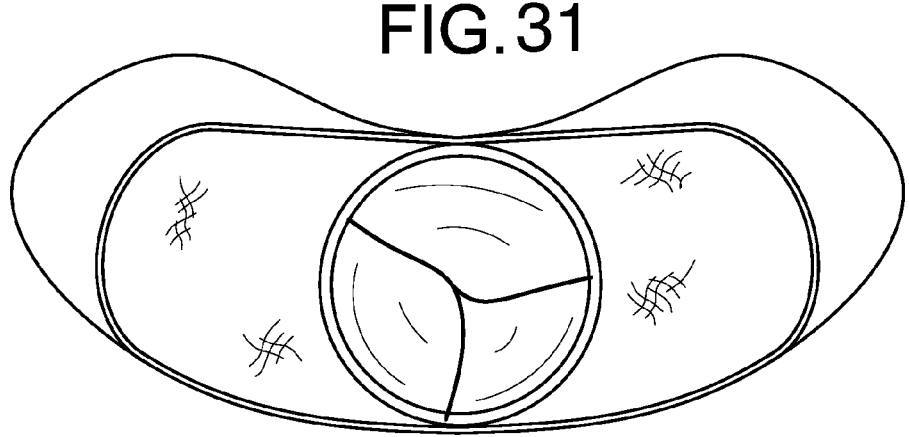

FIG. 31 is a top view of mitral valve anatomy having a stent-in-a-stent valve according to the present invention, and showing anterior and posterior segments of the mitral valve fully occupied and distended, addressing the commissural leaking issue.

Figure 32:
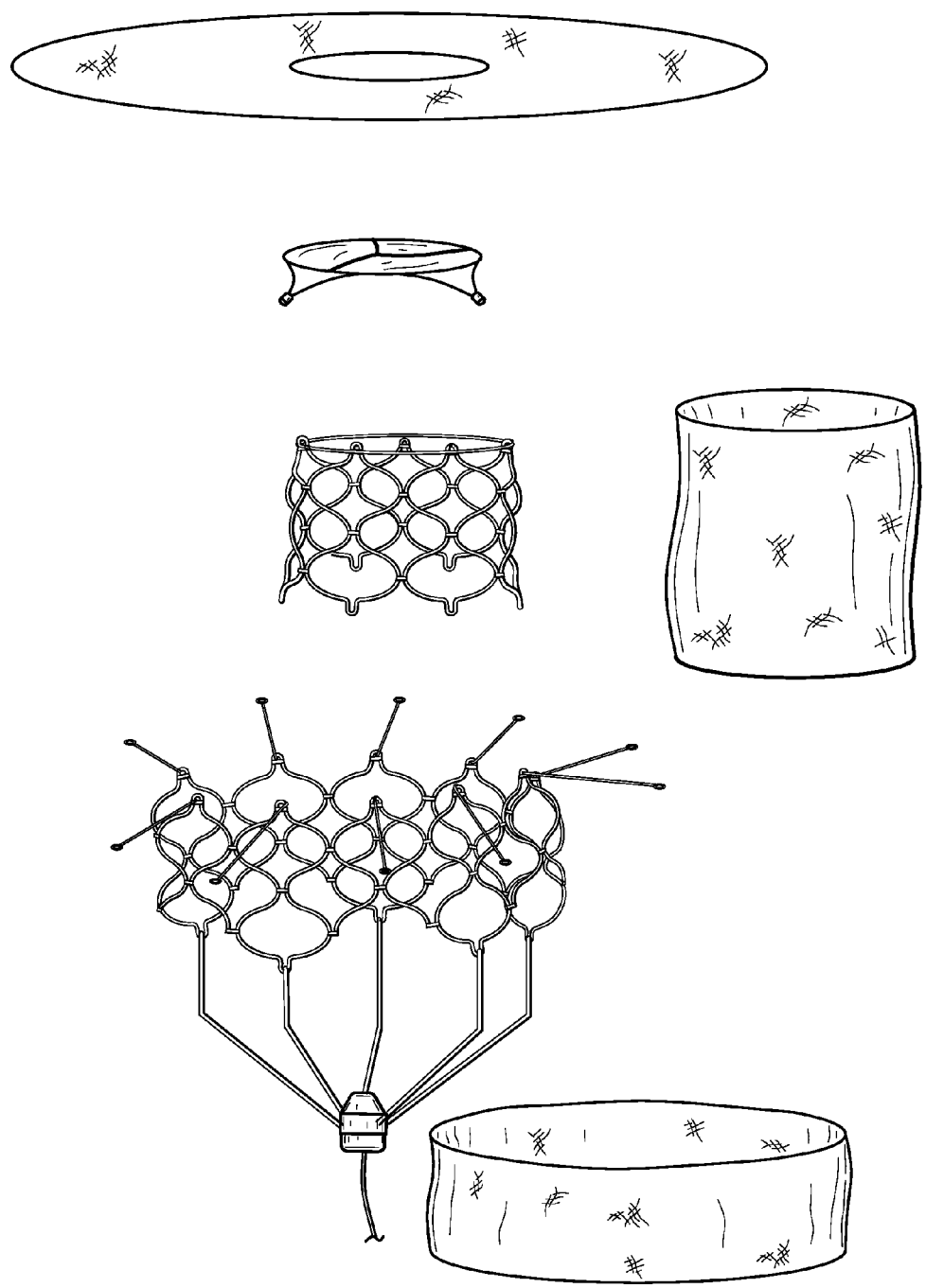

FIG. 32 is an exploded side view of one embodiment of the present invention, showing from top to bottom, the tissue collar for atrial sealing, the leaflet apparatus, the low-profile laser-cut nitinol inner stent, the inner stent tissue covering, the low-profile laser-cut nitinol outer stent with articulating arms to support the tissue collar, the intermediate wire tethers, the junction nut or collar, the outer stent tissue covering, and the single epicardial tether.

Figure 33:
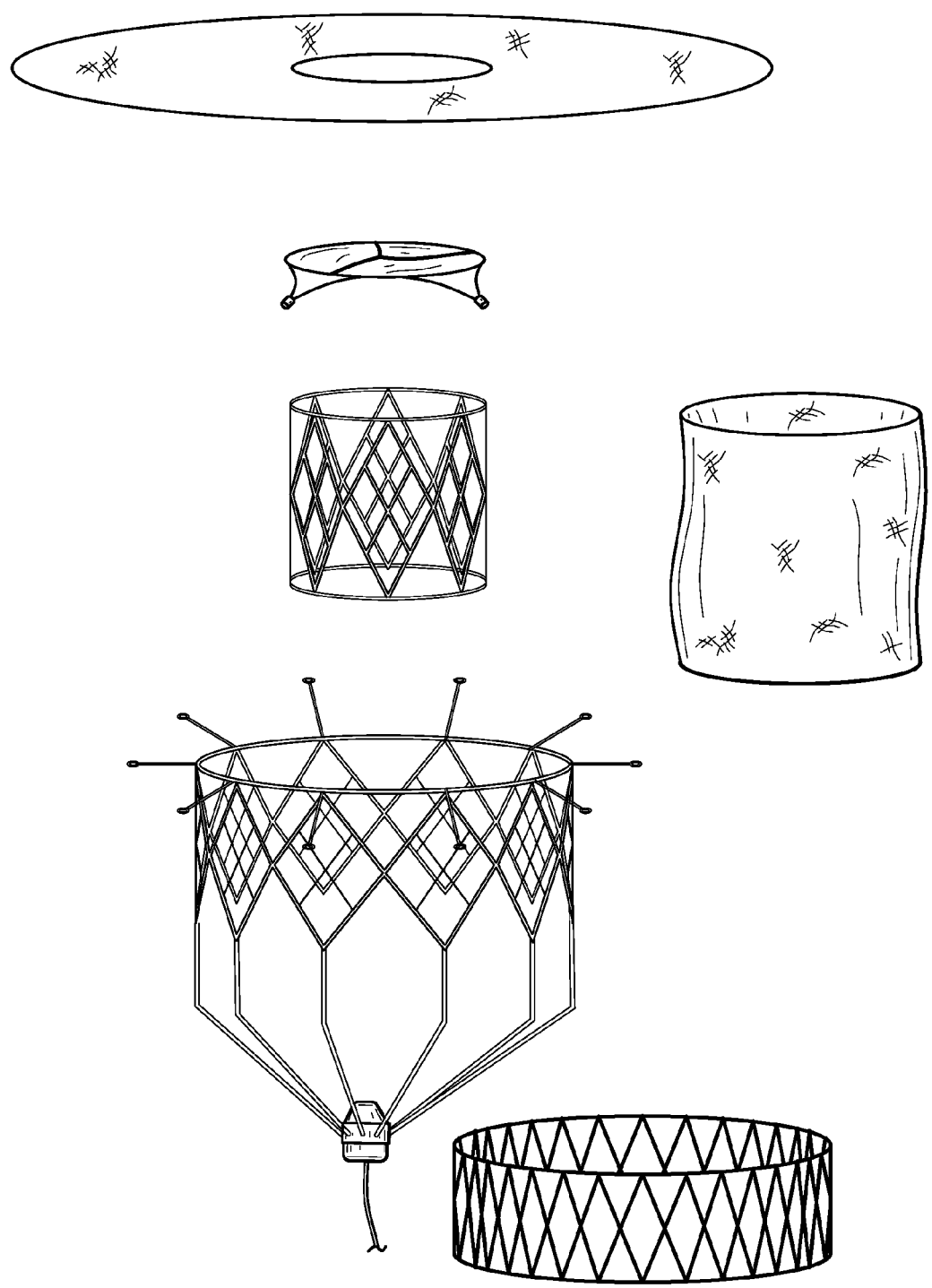

FIG. 33 is an exploded side view of one embodiment of the present invention, showing from top to bottom, the tissue collar for atrial sealing, the leaflet apparatus, the low-profile laser-cut diamond-fold design nitinol inner stent, the inner stent tissue covering, the low-profile laser-cut diamond-fold design nitinol outer stent with articulating arms to support the tissue collar, the intermediate wire tethers, the junction nut or collar, the outer stent tissue covering, and the single epicardial tether.

Figure 34:
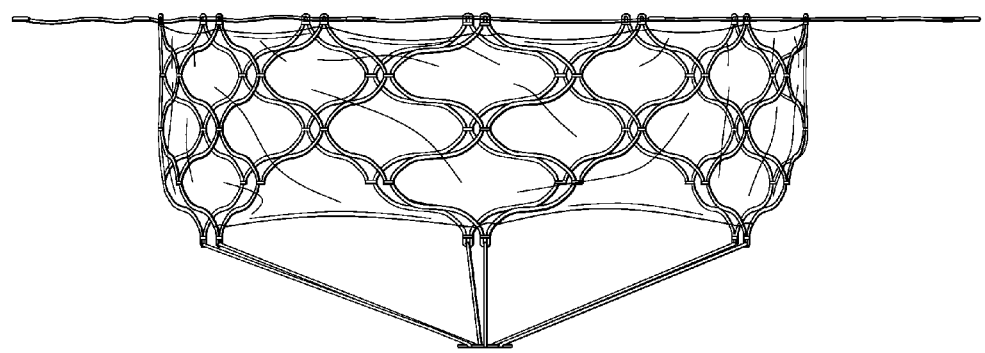

FIG. 34 is a side view of the outer stent wire form showing the attached atrial collar.

Figure 35:
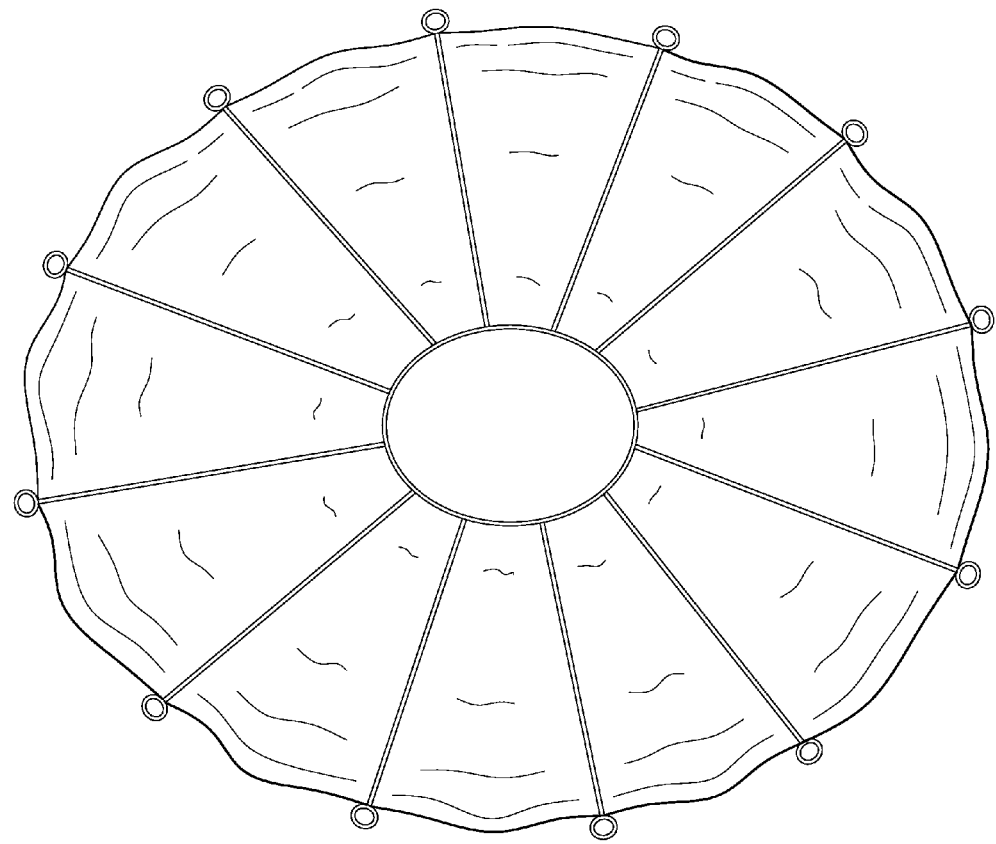

FIG. 35 is a top view of the atrial collar with thru-hole for the inner stent and leaflets (not shown).

Figure 36:
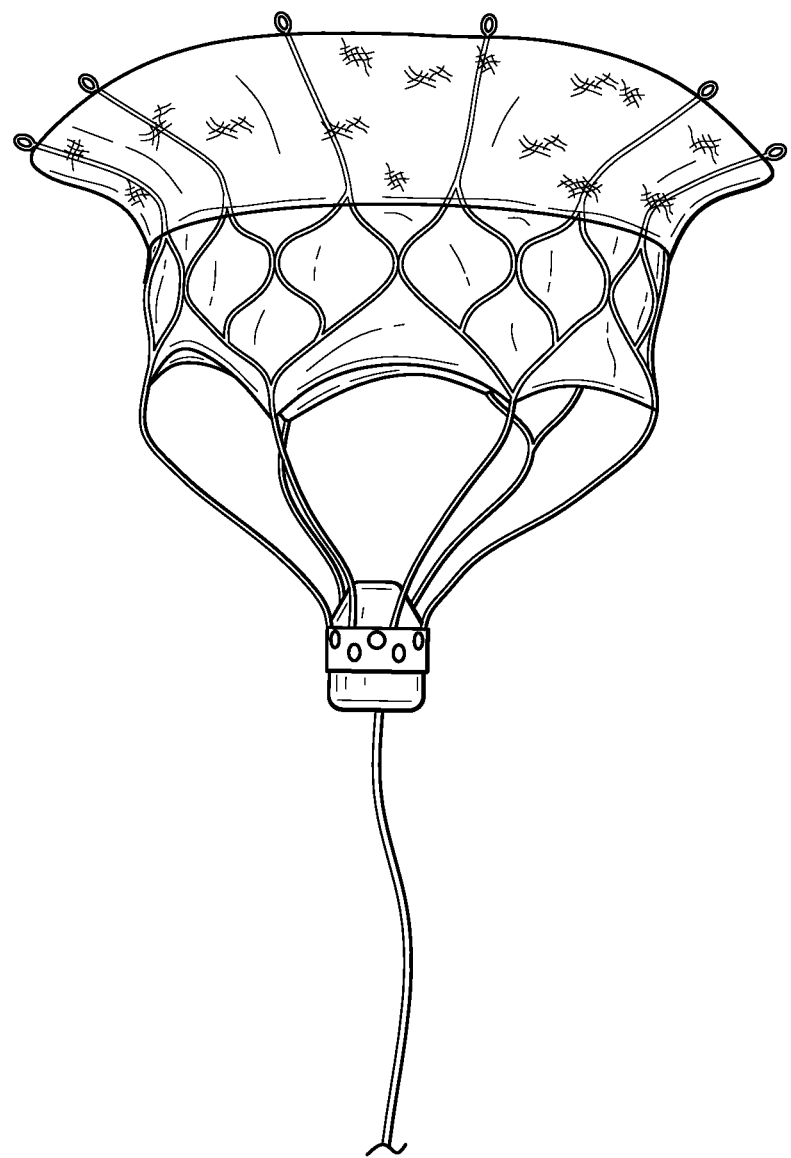

FIG. 36 is a lower side view of one embodiment showing the underside of the atrial sealing collar, the low height profile outer stent, the intermediate wire tethers attached at the junction and the single epicardial tether extending away.

Figure 37:
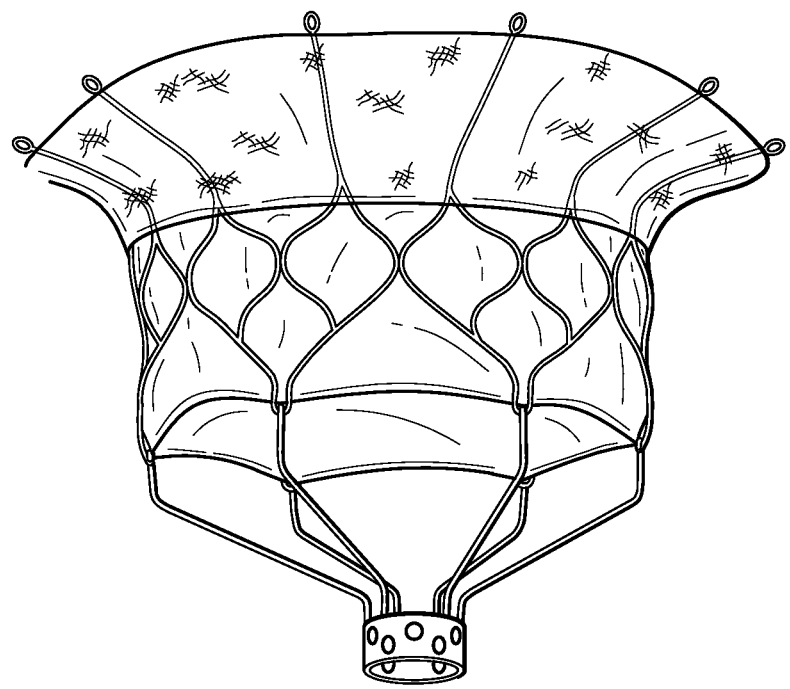

FIG. 37 is a lower side view of one embodiment showing the underside of the atrial sealing collar, the low height profile outer stent, the intermediate wire tethers attached at the junction.

Figure 38:
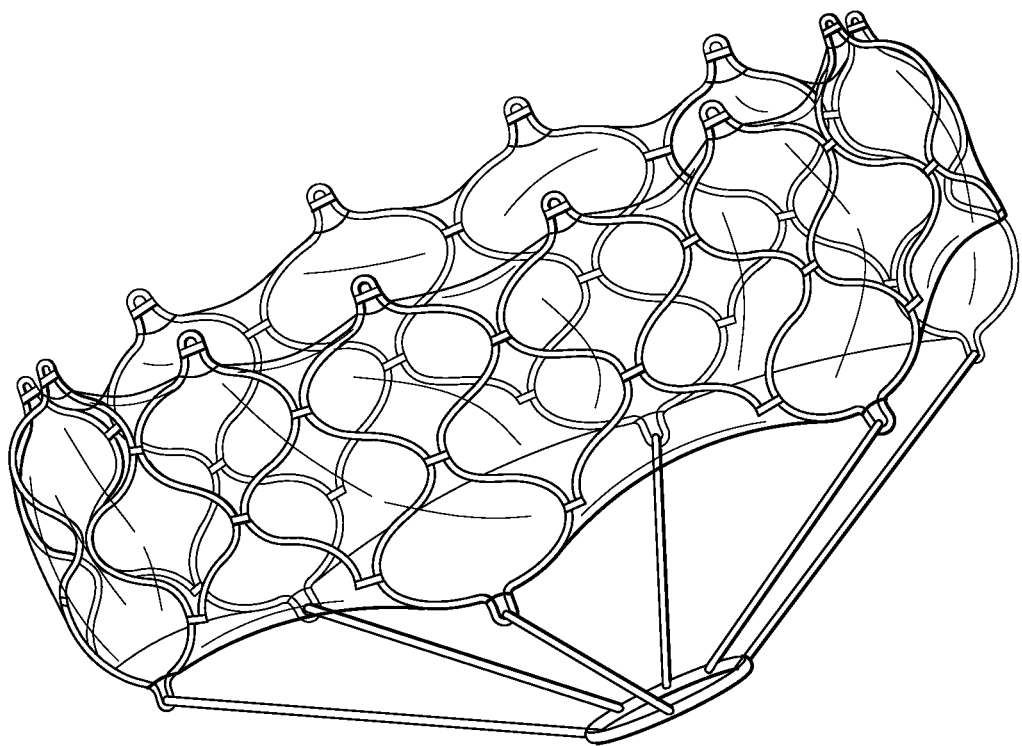

FIG. 38 is a side lower perspective view of one embodiment showing the wire-form skeleton of the low height profile outer stent.

Figure 39:
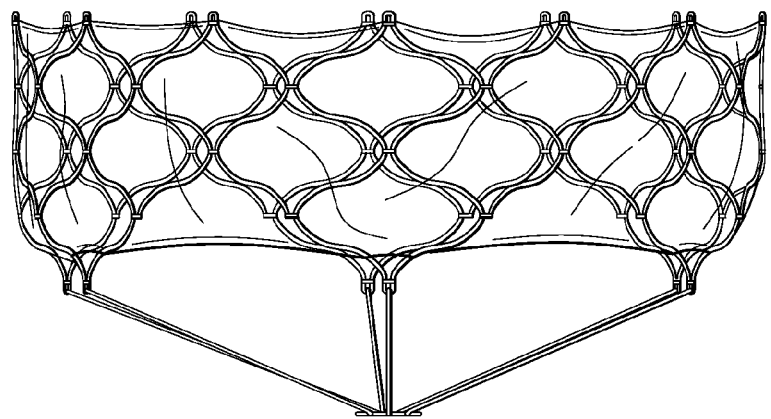

FIG. 39 is a side view of one embodiment showing the wire-form skeleton of the low height profile outer stent.

Figure 40:
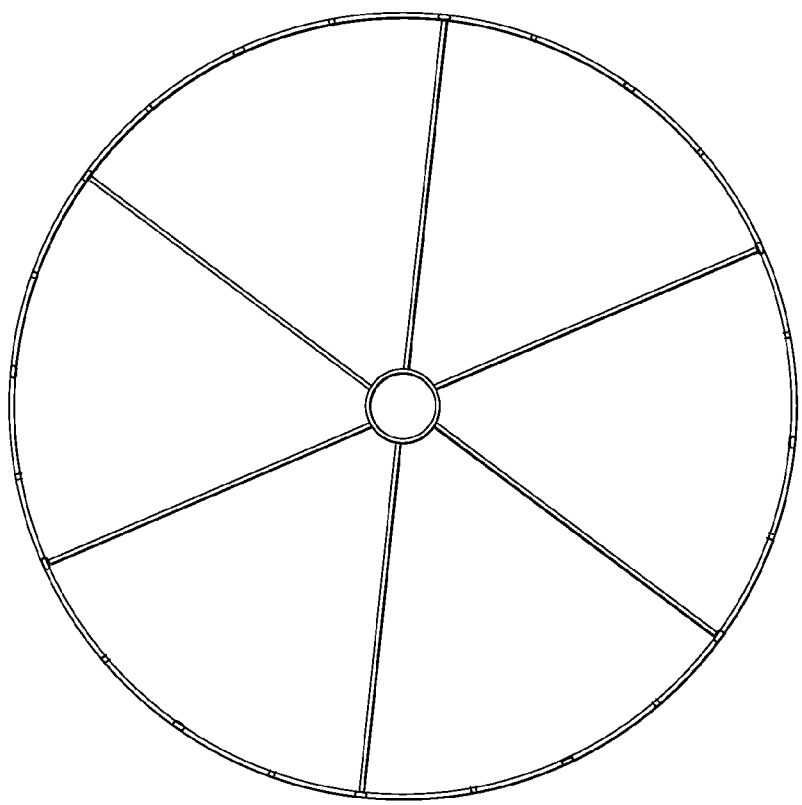

FIG. 40 is a top view of one embodiment showing the wire-form skeleton of the low height profile outer stent.

Trapdoor Sealing Device

Figure 41:
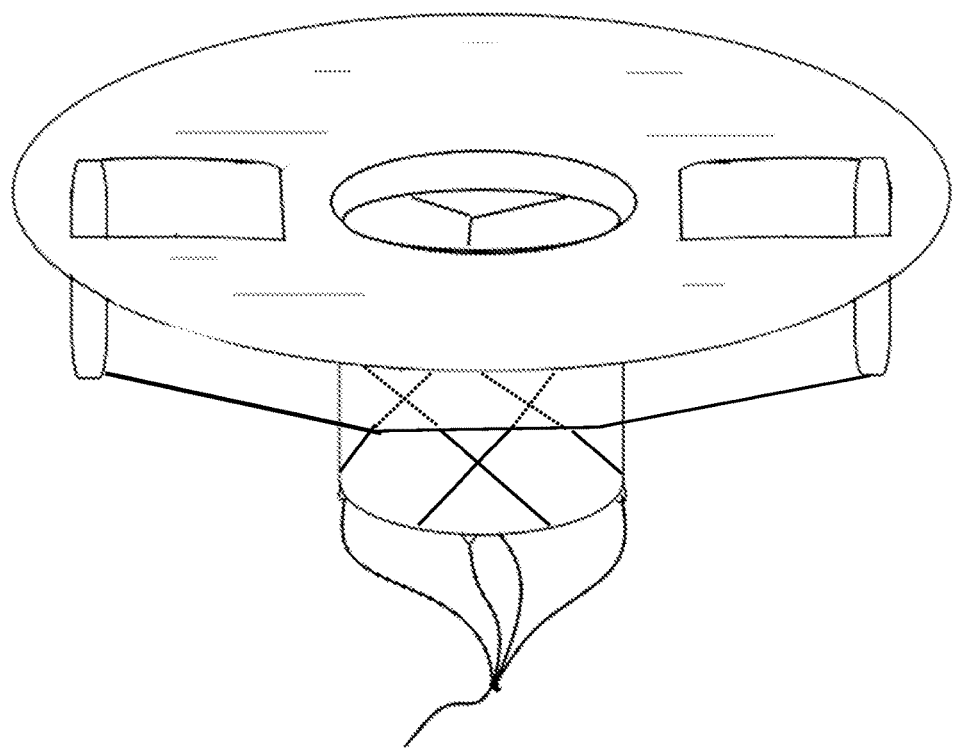

FIG. 41 is a perspective view of one laser cut stent embodiment showing the tissue-covered articulating collar structure attached to the expandable tubular nitinol stent with valve leaflets mounted therein, and the trap-door commissural wire-frame tab supports for the commissural sealing skirt.

Figure 42:
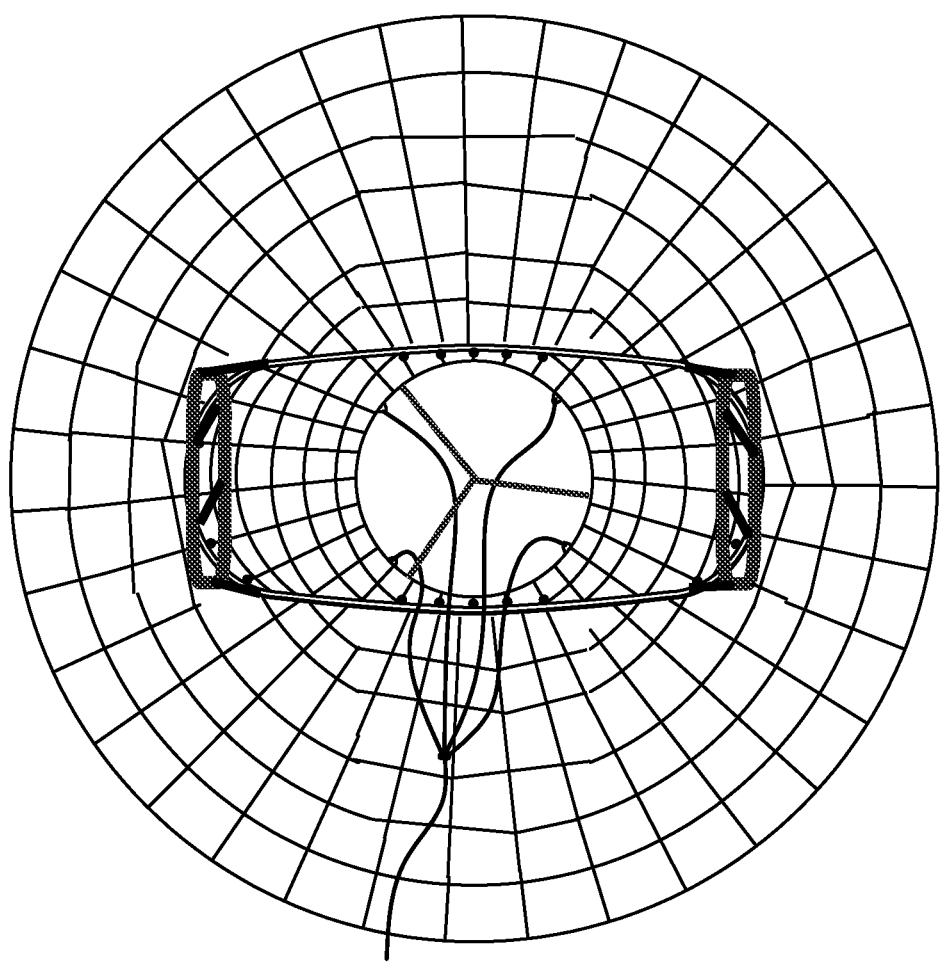

FIG. 42 is a bottom view of one embodiment showing the trap-door commissural wire-frame tab supports for the commissural sealing skirt. Note this figure may not illustrate the final valve product, as it may have surface coatings, e.g. synthetic material and/or stabilized tissue, etc., added.

Figure 43:
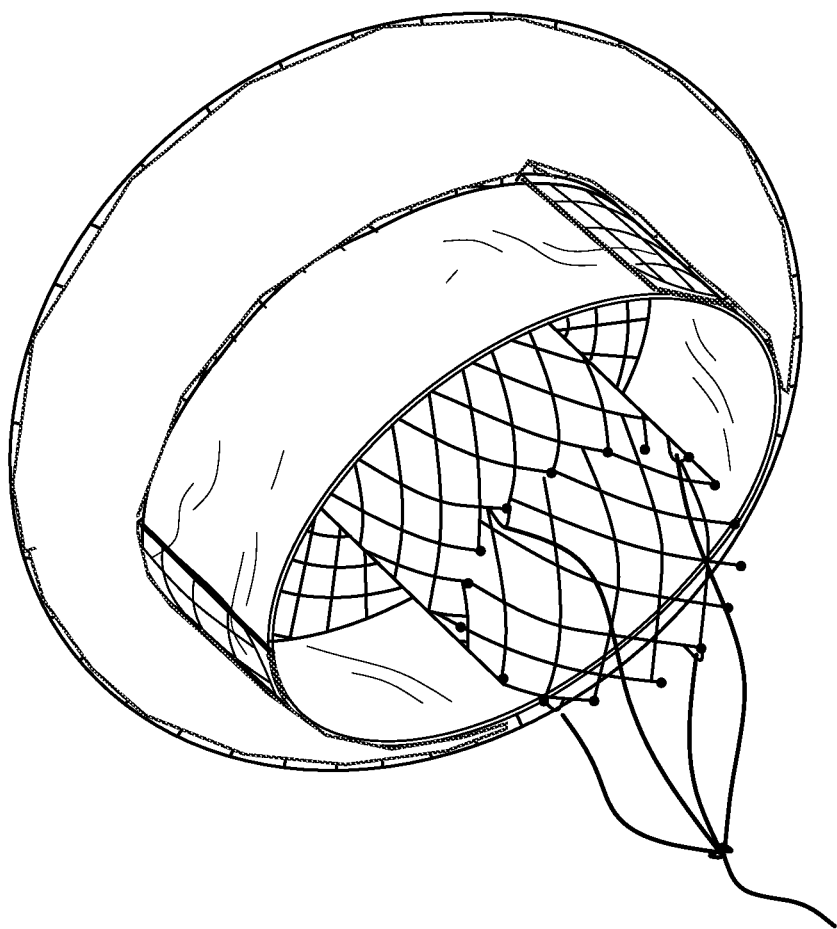

FIG. 43 is a perspective lower view of one embodiment showing laser cut stent embodiment showing the tissue-covered articulating collar structure attached to the expandable tubular nitinol stent with valve leaflets mounted therein, and the trap-door commissural wire-frame tab supports for the commissural sealing skirt.

Figure 44:
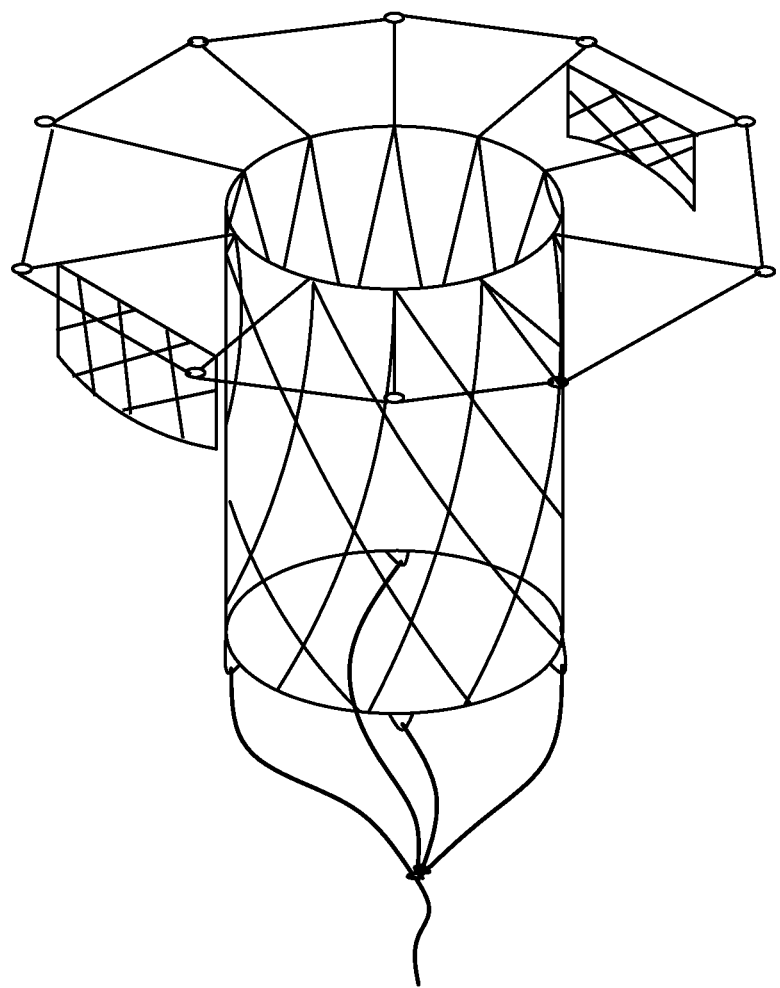

FIG. 44 is a perspective view of one laser-cut embodiment in a minimal wireframe view to highlight the trap-door commissural wire-frame tab supports for the commissural sealing skirt.

Figure 45:
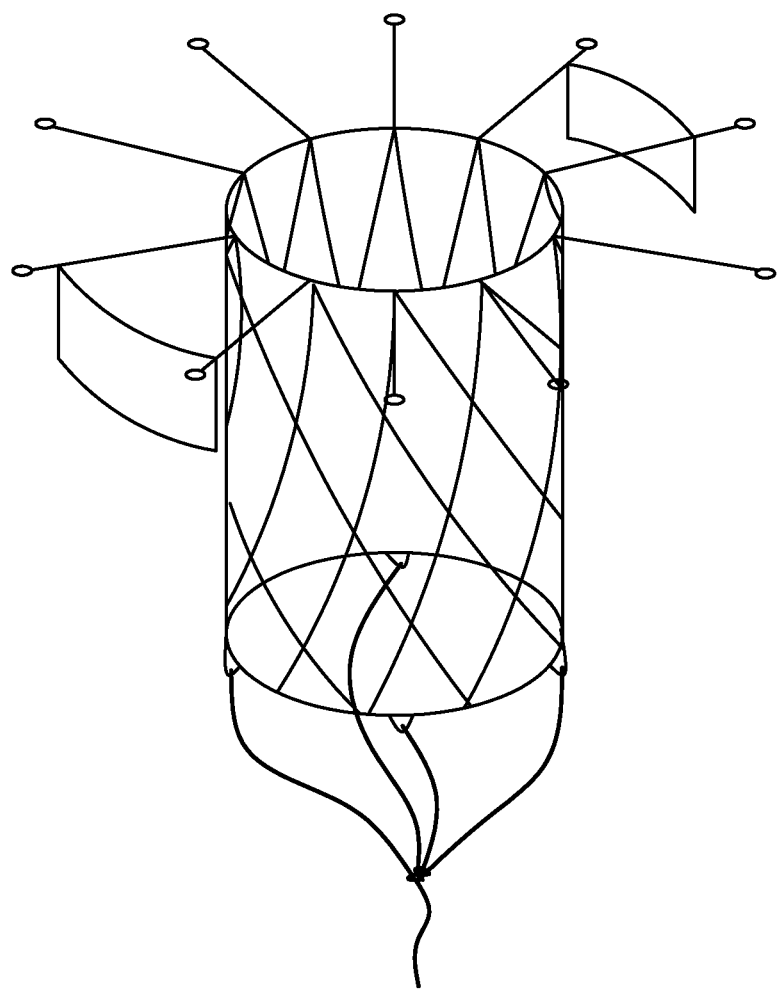

FIG. 45 is a perspective view of one laser-cut embodiment in a minimal wireframe view, without lines showing location of the collar, to highlight the trap-door commissural wire-frame tab supports for the commissural sealing skirt.

Figure 46:
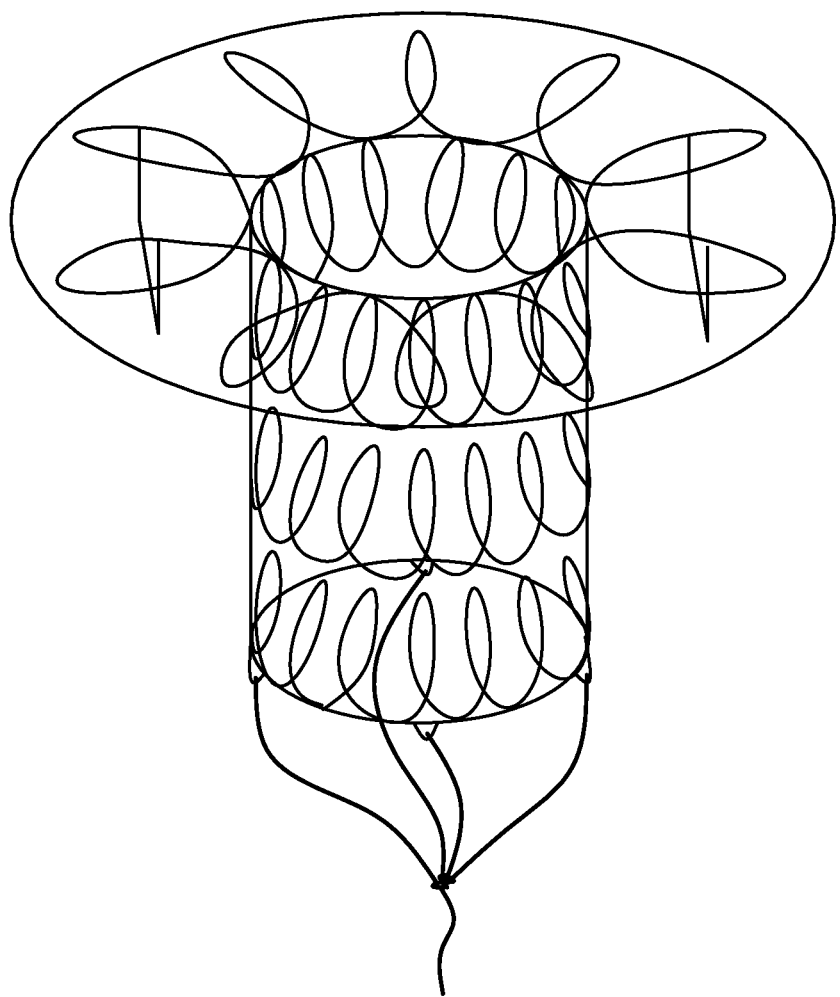

FIG. 46 is a perspective view of one braided stent embodiment in a minimal wire-frame view to highlight the addition of the trap-door commissural wire-frame tab supports for the commissural sealing skirt.

Figure 47:
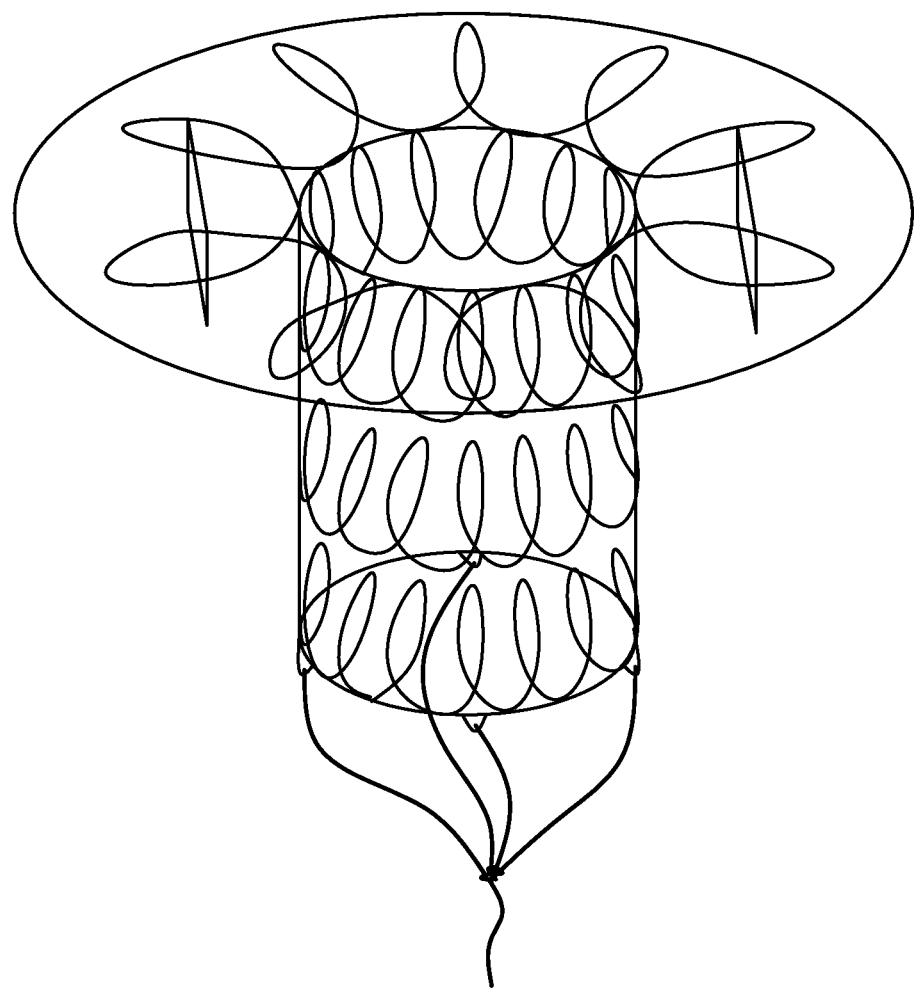

FIG. 47 is a perspective view of another braided stent embodiment in a minimal wire-frame view to highlight the addition of the trap-door commissural wire-frame tab supports for the commissural sealing skirt.

Figure 48:
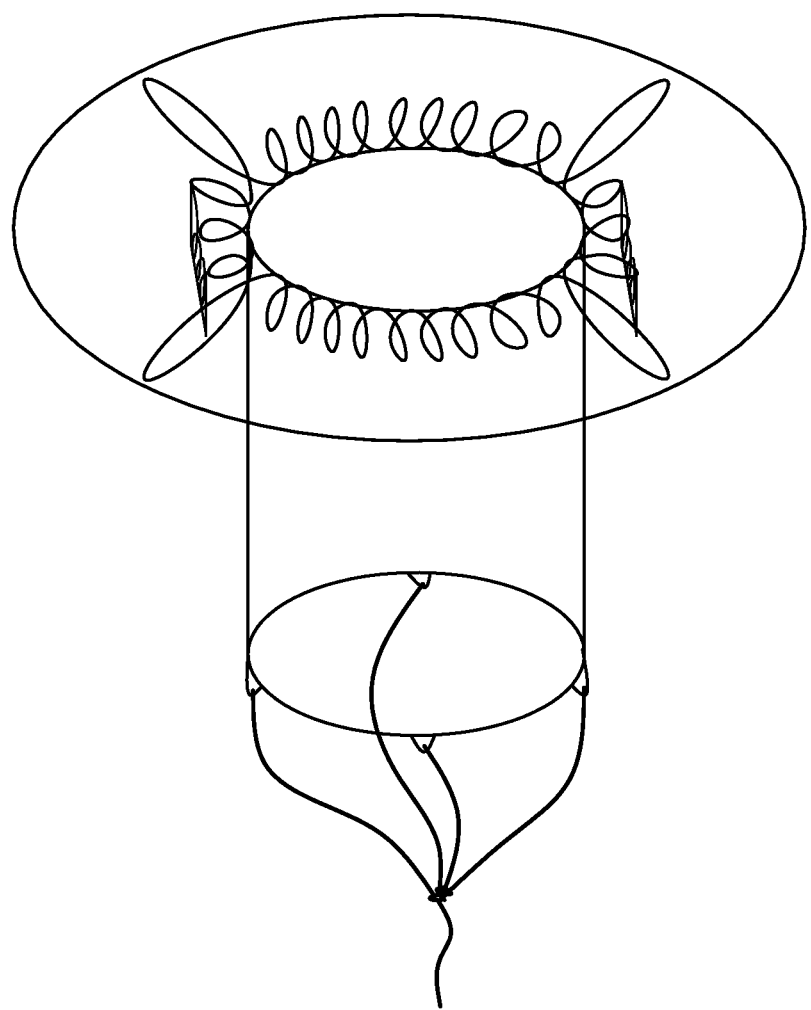

FIG. 48 is a perspective view of one braided stent embodiment in a minimal wire-frame view to highlight the outside-to-inward folding embodiment of the trap-door commissural wire-frame tab supports for the commissural sealing skirt.

Figure 49:
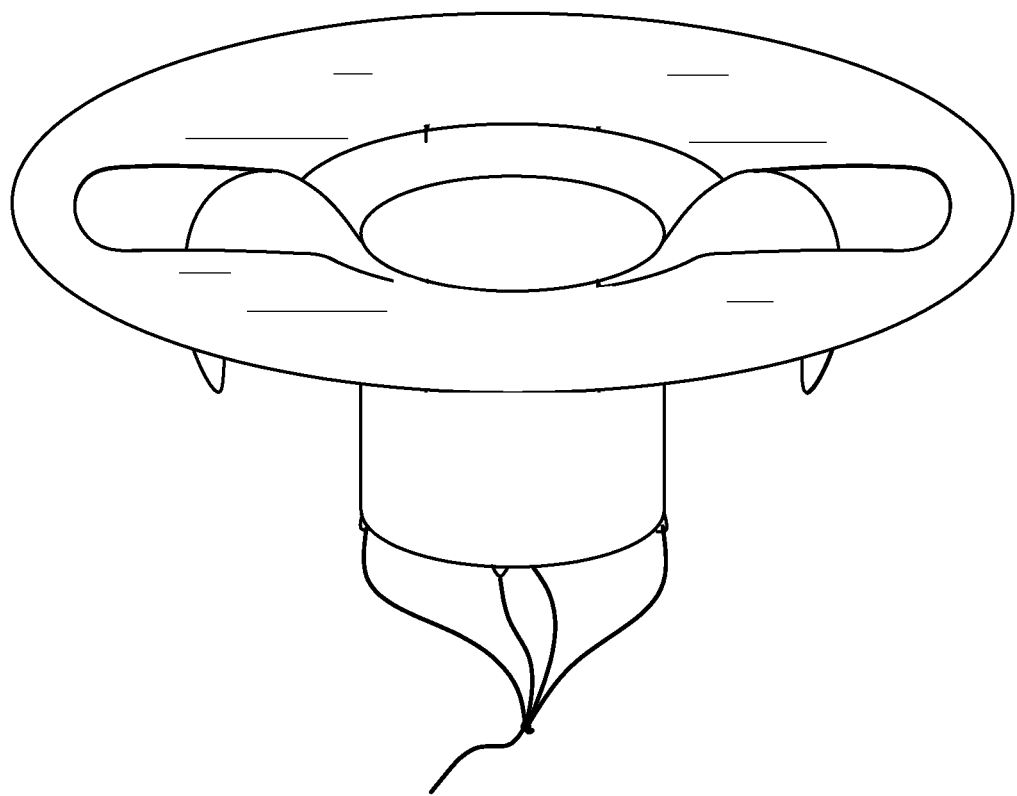

FIG. 49 is a perspective view of a laser-cut stent embodiment in a covered wireframe view to highlight the outside-to-inward folding embodiment of the trap-door commissural wire-frame tab supports for the commissural sealing skirt.

Figure 50:
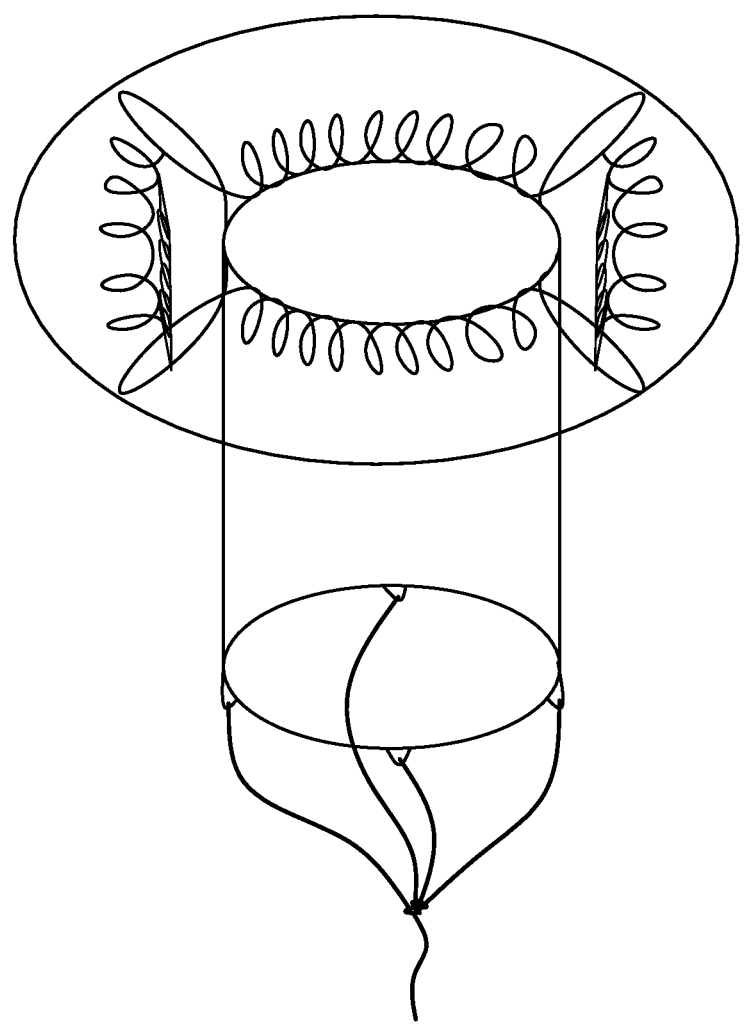

FIG. 50 is a perspective view of one braided stent embodiment in a minimal wire-frame view to highlight the inside-to-outward folding embodiment of the trap-door commissural wire-frame tab supports for the commissural sealing skirt.

Figure 51:
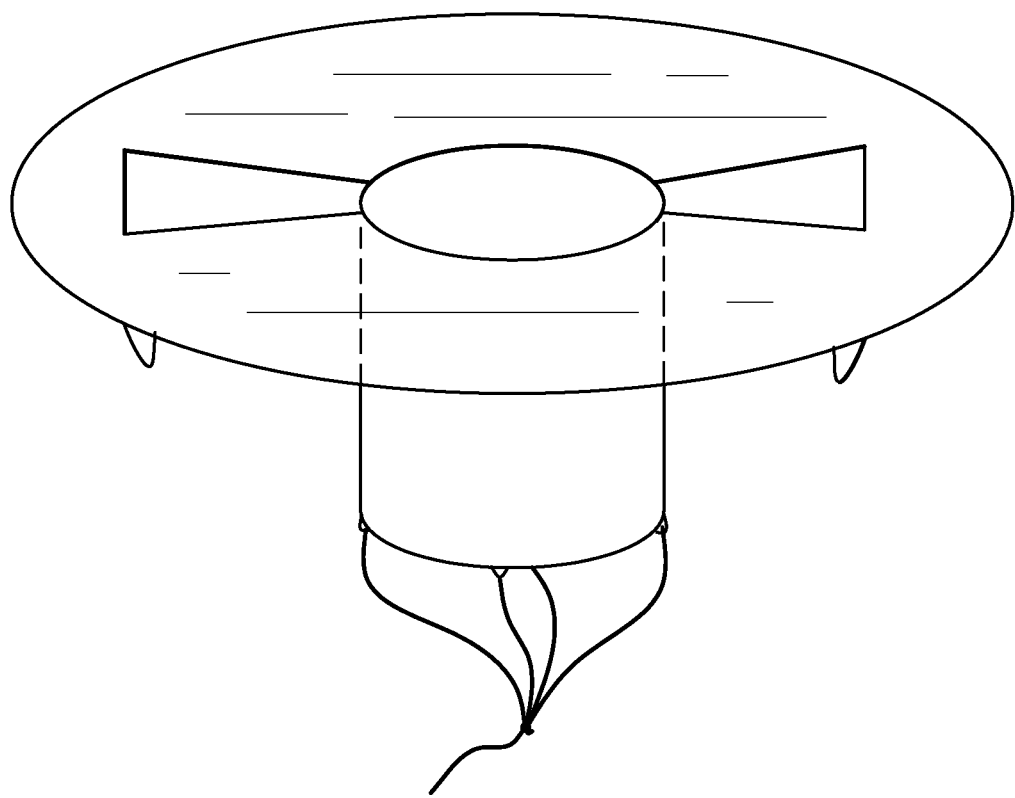

FIG. 51 is a perspective view of a laser-cut stent embodiment in a covered wireframe view to highlight the inside-to-outward folding embodiment of the trap-door commissural wire-frame tab supports for the commissural sealing skirt.

Figure 52:
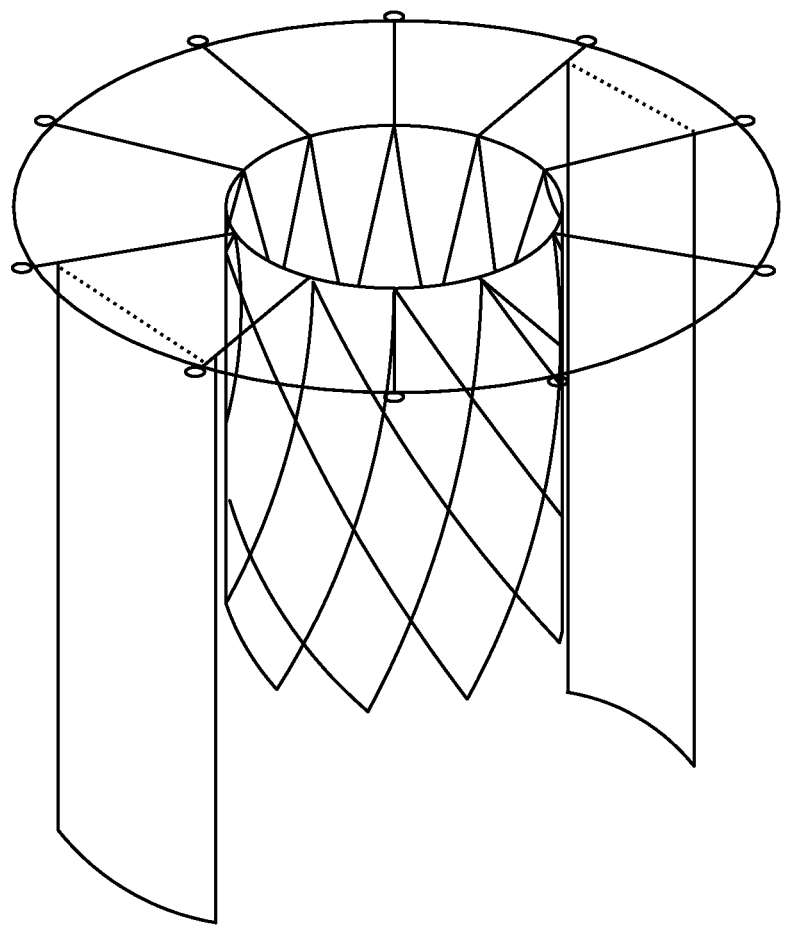

FIG. 52 is a perspective view of a laser-cut stent embodiment in a minimal wire-frame view to highlight the elongated-tab embodiment of the trap-door commissural wire-frame tab supports for the commissural sealing skirt.

DETAILED DESCRIPTION

The Functions of the Retrievable Stented Prosthetic Mitral Valve

The present invention provides in one embodiment a retrieval system for a previously deployed prosthetic heart valve wherein a plurality of valve tethers are attached to the valve or to a collapsable stent containing the valve, and such tethers are also attached to a guide component. On its opposite side, the guide component is attached to a single retrieval tether, which is used to anchor the valve into the native heart tissue.

The invention allows for the capture of the single retrieval tether by a catheter-based extraction device, and for the pulling of the entire valve apparatus into the catheter via the single retrieval tether. In a preferred embodiment, the guide component will be of a bullet, cone or hooded shape, and of a diameter allowing it to be held snugly within the catheter, so as to provide a steady and equal line of extraction force against each valve tether. As the valve tethers are retracted into the catheter, the retractive force will collapse the valve/stent assembly as it retracts into the catheter.

In another embodiment, the invention comprises a method of retrieving a tethered expandable transcatheter prosthetic heart valve that is deployed within the heart, comprising the steps of: retracting the tethered expandable transcatheter prosthetic heart valve into a retrieval catheter located within the heart, wherein the tethered expandable transcatheter prosthetic heart valve comprises a retrieval guide located between the expandable prosthetic heart valve and a tether structure, the expandable prosthetic heart valve comprising a stent structure with internal valve leaflets, the stent structure having an anti-regurgitation mechanism at its upper end, said anti-regurgitation mechanism selected from an upper cuff component or wherein the stent structure is wedge shaped, the distal cuff and wedge-shape providing anchoring tension within the deployment location, the stent structure having a tether-attachment structure at its lower end, said tether structure comprising one or more tethers attached to the tether-attachment structure, and wherein said retrieval guide is bullet-shaped, cone-shaped, hooded or otherwise shaped to guide or receive the lower end of the expandable transcatheter prosthetic heart valve and facilitate the compression of the expandable transcatheter prosthetic heart valve to approximately the same diameter as the retrieval catheter and facilitate the retraction of the compressed expandable transcatheter prosthetic heart valve into the retrieval catheter.

The prosthetic heart valve comprises a self-expanding tubular stent having a cuff at one end and tether loops for attaching tethers at the other end, and disposed within the tubular stent is a leaflet assembly that contains the valve leaflets, the valve leaflets being formed from stabilized tissue or other suitable biological or synthetic material. In one embodiment, the leaflet assembly comprises a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

Functions of the Cuff

The cuff functions in a variety of ways. The first function of the cuff is to inhibit perivalvular leak/regurgitation of blood around the prosthesis. By flexing and sealing across the irregular contours of the annulus and atrium, leaking is minimized and/or prevented.

The second function of the cuff is to provide an adjustable and/or compliant bioprosthetic valve. The heart and its structures undergo complex conformational changes during the cardiac cycle. For example, the mitral valve annulus has a complex geometric shape known as a hyperbolic parabloid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the cuff-based compliance.

The third function of the cuff valve is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The forth function of the cuff is to counter the forces that act to displace the prosthesis toward/into the ventricle (i.e. atrial pressure and flow-generated shear stress) during ventricular filling.

Additional features of the cuff include that it functions to strengthen the leaflet assembly/stent combination by providing additional structure. Further, during deployment, the cuff functions to guide the entire structure, the prosthetic valve, into place at the mitral annulus during deployment and to keep the valve in place once it is deployed.

Functions of the Passively Oscillating Dome-Shaped Sealing Canopy

The passively oscillating dome-shaped sealing canopy functions by utilizing a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a periannular seal by retrograde hemodynamic forces. The umbrella or parachute shaped design uses the hemodynamic back-pressure generated during ventricular contraction to fill the sub-umbrellar spaces between the deformable inner surface of the canopy material and the external surface of the stent. That the canopy extends to the wire halo, extending beyond the proximal end of the stent body, leaves a skirt of material that is longer than the stent body. The wire halo also creates a space between itself and the proximal end of the stent. During ventricular contraction or systole, the blood is ejected towards the prosthetic mitral valve. Retrograde blood hitting the prosthetic valve leaflets cause the leaflets to close, preventing regurgitation into the left atrium. Retrograde blood will then fill the subannular space around the chordae tendinae, which is frequently the cause and location of leakage around prosthetic valves which have been deployed into and through the native valve and annulus. However, the canopy is constructed with a size and/or type of material so as to cause the retrograde blood to be caught under its dome-shape and to deform into and around the periannular space, in effect, to fill and sag against the seam located at the underside of the native mitral valve annulus and the axially-deployed prosthetic stent-valve, or at least to create enough of a ballooning gasket, such as will result in a sealing of the periannular leaks.

Functions of the Stent-in-a-Stent Design

The stent-in-a-stent design functions by utilizing an outer stent which is fitted to reduce leakage of the particular cardiovascular valve and an inner stent which acts as the valve prosthesis.

Further, during ventricular contraction or systole, the blood is ejected towards the prosthetic mitral valve on its way towards the aortic valve. Retrograde blood hitting the prosthetic valve leaflets cause the leaflets to close, preventing regurgitation into the left atrium. Retrograde blood will then fill the subannular space around the chordae tendinae, which is frequently the cause and location of leakage around prosthetic valves which have been deployed into and through the native valve and annulus. However, the outer stent is constructed with a size and/or type of material so as to cause the retrograde blood to be caught under its shape and to deform into and around the periannular space, in effect, to fill and sag against the seam located at the underside of the native mitral valve annulus and the axially-deployed prosthetic stent-valve, or at least to create enough of a ballooning gasket, such as will result in a sealing of the periannular leaks.

Functions of the Trap-Door Commissural Wire-Frame Tab Supports for the Commissural Sealing Skirt The trap-door commissural wire-frame tab supports for the commissural sealing skirt functions by utilizing an oval skirt of stabilized tissue or synthetic material attached to the underside of the collar or cuff structure and stretched between two or more subannular, sub-collar wire-frame tabs, wherein during systole the leaflet assembly closes and the sealing canopy is filled to form a commissural seal by retrograde hemodynamic forces. During ventricular contraction or systole, the blood is ejected towards the prosthetic mitral valve. Retrograde blood hitting the prosthetic valve leaflets cause the leaflets to close, preventing regurgitation into the left atrium. Retrograde blood will then fill the subannular space around the chordae tendinae, which is frequently the cause and location of commissural leakage around prosthetic valves which have been deployed into and through the native valve and annulus. However, the canopy is constructed with a size and/or type of material so as to cause the retrograde blood to be caught and to deform into the commissural space, in effect, to fill and sag against the seam located at the underside of the native mitral valve annulus and the axially-deployed prosthetic stent-valve, or at least to create enough of a ballooning gasket, such as will result in a sealing of any commissural leaks.

Functions of the Flared End of the Stent to Effect Atrial Sealing

The flared end or cuff functions in a variety of ways. The first function of the flared end or cuff is to inhibit perivalvular leak/regurgitation of blood around the prosthesis. By flexing and sealing across the irregular contours of the annulus and atrium, leaking is minimized and/or prevented.

The second function of the flared end or cuff is to provide an adjustable and/or compliant bioprosthetic valve. The heart and its structures undergo complex conformational changes during the cardiac cycle. For example, the mitral valve annulus has a complex geometric shape known as a hyperbolic paraboloid much like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to maintain structural position and integrity during the cardiac cycle. Compliance with the motion of the heart is a particularly important feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the flared end or cuff-based compliance.

The third function of the flared end or cuff and valve is to provide a valve that, during surgery, is able to be seated and be able to contour to the irregular surfaces of the atrium. The use of independent tethers allows for side to side fitting of the valve within the annulus. For example, where three tethers are used, they are located circumferentially about 120 degrees relative to each other which allows the surgeon to observe whether or where perivalvular leaking might be occurring and to pull on one side or the other to create localized pressure and reduce or eliminate the leaking.

The fourth function of the flared end or cuff is to counter the forces that act to displace the prosthesis toward/into the ventricle (i.e. atrial pressure and flow-generated shear stress) during ventricular filling.

Additional features of the flared end or cuff include that it functions to strengthen the leaflet assembly/stent combination by providing additional structure. Further, during deployment, the flared end or cuff functions to guide the entire structure, the prosthetic valve, into place at the mitral annulus during deployment and to keep the valve in place once it is deployed. Another important function is to reduce pulmonary edema by improving atrial drainage.

Functions of the Stent-in-a-Stent Design

The stent-in-a-stent design functions by utilizing an outer stent which is fitted to reduce leakage of the particular cardiovascular valve and an inner stent which acts as the valve prosthesis.

Further, during ventricular contraction or systole, the blood is ejected towards the prosthetic mitral valve on its way towards the aortic valve. Retrograde blood hitting the prosthetic valve leaflets cause the leaflets to close, preventing regurgitation into the left atrium. Retrograde blood will then fill the subannular space around the chordae tendinae, which is frequently the cause and location of leakage around prosthetic valves which have been deployed into and through the native valve and annulus. However, the outer stent is constructed with a size and/or type of material so as to cause the retrograde blood to be caught under its shape and to deform into and around the periannular space, in effect, to fill and sag against the seam located at the underside of the native mitral valve annulus and the axially-deployed prosthetic stent-valve, or at least to create enough of a ballooning gasket, such as will result in a sealing of the periannular leaks.

Flared End or Cuff Structure

The flared end or cuff is a substantially flat plate that projects beyond the diameter of the tubular stent to form a rim or border. As used herein, the term flared end, cuff, flange, collar, bonnet, apron, or skirting are considered to be functionally equivalent. When the tubular stent is pulled through the mitral valve aperture, the mitral annulus, by the tether loops in the direction of the left ventricle, the flared end or cuff acts as a collar to stop the tubular stent from traveling any further through the mitral valve aperture. The entire prosthetic valve is held by longitudinal forces between the flared end or cuff which is seated in the left atrium and mitral annulus, and the ventricular tethers attached to the left ventricle.

The flared end or cuff is formed from a stiff, flexible shape-memory material such as the nickel-titanium alloy material Nitinol™ wire that is covered by stabilized tissue or other suitable biocompatible or synthetic material. In one embodiment, the flared end or cuff wire form is constructed from independent articulating radial tines or posts of wire extending axially around the circumference of the bend or seam where the flared end or cuff transitions to the tubular stent (in an integral flared end or cuff) or where the flared end or cuff is attached to the stent (where they are separate, but joined components).

Once covered by stabilized tissue or material, the articulating radial tines or posts of wire provide the flared end or cuff the ability to travel up and down, to articulate, along the longitudinal axis that runs through the center of the tubular stent. In other words, the individual articulating radial tines or posts of wire can independently move up and down, and can spring back to their original position due to the relative stiffness of the wire. The tissue or material that covers the flared end or cuff wire has a certain modulus of elasticity such that, when attached to the wire of the flared end or cuff, is able to allow the wire spindles to move. This flexibility gives the flared end or cuff, upon being deployed within a patient's heart, the ability to conform to the anatomical shape necessary for a particular application. In the example of a prosthetic mitral valve, the flared end or cuff is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing the a mitral valve and prevents blood from leaking around the implanted prosthetic heart valve.

An additional important aspect of the flared end or cuff dimension and shape is that, when fully seated and secured, the edge of the flared end or cuff preferably should not be oriented laterally into the atrial wall such that it can produce a penetrating or cutting action on the atrial wall.

In one preferred embodiment, the wire spindles of the flared end or cuff are substantially uniform in shape and size. In another preferred embodiment of the present invention, each loop or spindle may be of varying shapes and sizes. In this example, it is contemplated that the articulating radial tines or posts of wire may form a pattern of alternating large and small articulating radial tines or posts of wire, depending on where the valve is being deployed. In the case of a prosthetic mitral valve, pre-operative imaging may allow for customizing the structure of the flared end or cuff depending on a particular patient's anatomical geometry in the vicinity of the mitral annulus.

The flared end or cuff wire form is constructed so as to provide sufficient structural integrity to withstand the intracardiac forces without collapsing. The flared end or cuff wire form is preferably constructed of a superelastic metal, such as Nitinol™® and is capable of maintaining its function as a sealing collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the flared end or cuff as an anchoring force holding the flared end or cuff against the atrial tissue that is adjacent the mitral valve. The flared end or cuff counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the flared end or cuff has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Cuff Structure

The cuff is a substantially flat plate that projects beyond the diameter of the tubular stent to form a rim or border. As used herein, the term cuff, flange, collar, bonnet, apron, or skirting are considered to be functionally equivalent. When the tubular stent is pulled through the mitral valve aperture, the mitral annulus, by the tether loops in the direction of the left ventricle, the cuff acts as a collar to stop the tubular stent from traveling any further through the mitral valve aperture. The entire prosthetic valve is held by longitudinal forces between the cuff which is seated in the left atrium and mitral annulus, and the ventricular tethers attached to the left ventricle.

The cuff is formed from a stiff, flexible shape-memory material such as the nickel-titanium alloy material Nitinol™ wire that is covered by stabilized tissue or other suitable biocompatible or synthetic material. In one embodiment, the cuff wire form is constructed from independent loops of wire that create lobes or segments extending axially around the circumference of the bend or seam where the cuff transitions to the tubular stent (in an integral cuff) or where the cuff is attached to the stent (where they are separate, but joined components).

Once covered by stabilized tissue or material, the loops provide the cuff the ability to travel up and down, to articulate, along the longitudinal axis that runs through the center of the tubular stent. In other words, the individual spindles or loops can independently move up and down, and can spring back to their original position due to the relative stiffness of the wire. The tissue or material that covers the cuff wire has a certain modulus of elasticity such that, when attached to the wire of the cuff, is able to allow the wire spindles to move. This flexibility gives the cuff, upon being deployed within a patient's heart, the ability to conform to the anatomical shape necessary for a particular application. In the example of a prosthetic mitral valve, the cuff is able to conform to the irregularities of the left atrium and shape of the mitral annulus, and to provide a tight seal against the atrial tissue adjacent the mitral annulus and the tissue within the mitral annulus. As stated previously, this feature importantly provides a degree of flexibility in sizing the a mitral valve and prevents blood from leaking around the implanted prosthetic heart valve.

An additional important aspect of the cuff dimension and shape is that, when fully seated and secured, the edge of the cuff preferably should not be oriented laterally into the atrial wall such that it can produce a penetrating or cutting action on the atrial wall.

In one preferred embodiment, the wire spindles of the cuff are substantially uniform in shape and size. In another preferred embodiment of the present invention, each loop or spindle may be of varying shapes and sizes. In this example, it is contemplated that the loops may form a pattern of alternating large and small loops, depending on where the valve is being deployed. In the case of a prosthetic mitral valve, pre-operative imaging may allow for customizing the structure of the cuff depending on a particular patient's anatomical geometry in the vicinity of the mitral annulus.

The cuff wire form is constructed so as to provide sufficient structural integrity to withstand the intracardiac forces without collapsing. The cuff wire form is preferably constructed of a superelastic metal, such as Nitinol™® and is capable of maintaining its function as a sealing collar for the tubular stent while under longitudinal forces that might cause a structural deformation or valve displacement. It is contemplated as within the scope of the invention to optionally use other shape memory alloys such as Cu—Zn—Al—Ni alloys, and Cu—Al—Ni alloys. The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the cuff as an anchoring force holding the cuff against the atrial tissue that is adjacent the mitral valve. The cuff counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, the cuff has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Stent Structure

Preferably, superelastic metal wire, such as Nitinol™ wire, is used for the stent, for the inner wire-based leaflet assembly that is disposed within the stent, and for the cuff wire form. As stated, it is contemplated as within the scope of the invention to optionally use other shape memory alloys such as Cu—Zn—Al—Ni alloys, and Cu—Al—Ni alloys. It is contemplated that the stent may be constructed as a braided stent or as a laser cut stent. Such stents are available from any number of commercial manufacturers, such as Pulse Systems. Laser cut stents are preferably made from Nickel-Titanium (Nitinol™), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

Laser Cut Stent

One possible construction of the stent envisions the laser cutting of a thin, isodiametric Nitinol tube. The laser cuts form regular cutouts in the thin Nitinol tube. Secondarily the tube is placed on a mold of the desired shape, heated to the Martensitic temperature and quenched. The treatment of the stent in this manner will form a stent or stent/cuff that has shape memory properties and will readily revert to the memory shape at the calibrated temperature.

Braided Wire Stent

A stent can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided stent is placed on a shaping fixture and placed in a muffle furnace at a specified temperature to set the stent to the desired shape and to develop the martensitic or super elastic properties desired.

The stent as envisioned in one preferred embodiment is designed such that the ventricular aspect of the stent comes to 2-5 points onto which anchoring sutures are affixed. The anchoring sutures (tethers) will traverse the ventricle and ultimately be anchored to the epicardial surface of the heart approximately at the level of the apex. The tethers when installed under slight tension will serve to hold the valve in place, i.e. inhibit paravalvular leakage during systole.

Leaflet and Assembly Structure

The valve leaflets are held by, or within, a leaflet assembly. In one preferred embodiment of the invention, the leaflet assembly comprises a leaflet wire support structure to which the leaflets are attached and the entire leaflet assembly is housed within the stent body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the stent body.

In this embodiment, the leaflet wire support structure is constructed to have a collapsible/expandable geometry. In a preferred embodiment, the structure is a single piece of wire. The wireform is, in one embodiment, constructed from a shape memory alloy such as Nitinol. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms that are able to collapse/compress which is followed by an expansion to its functional shape. In certain preferred embodiments, there may be 2, 3 or 4 arches. In another embodiment, closed circular or ellipsoid structure designs are contemplated. In another embodiment, the wire form may be an umbrella-type structure, or other similar unfold-and-lock-open designs. A preferred embodiment utilizes super elastic Nitinol wire approximately 0.015" in diameter. In this embodiment, the wire is wound around a shaping fixture in such a manner that 2-3 commissural posts are formed. The fixture containing the wrapped wire is placed in a muffle furnace at a pre-determined temperature to set the shape of the wire form and to impart it's super elastic properties. Secondarily, the loose ends of the wireform are joined with a stainless steel or Nitinol tube and crimped to form a continuous shape. In another preferred embodiment, the commissural posts of the wireform are adjoined at their tips by a circular connecting ring, or halo, whose purpose is to minimize inward deflection of the post(s).

In another preferred embodiment, the leaflet assembly is constructed solely of stabilized tissue or other suitable material without a separate wire support structure. The leaflet assembly in this embodiment is also disposed within the lumen of the stent and is attached to the stent to provide a sealed joint between the leaflet assembly and the inner wall of the stent. By definition, it is contemplated within the scope of the invention that any structure made from stabilized tissue and/or wire(s) related to supporting the leaflets within the stent constitute a leaflet assembly.

In this embodiment, stabilized tissue or suitable material may also optionally be used as a liner for the inner wall of the stent and is considered part of the leaflet assembly.

Liner tissue or biocompatible material may be processed to have the same or different mechanical qualities, e.g. thickness, durability, etc. from the leaflet tissue.

Deployment within the Valvular Annulus

The prosthetic heart valve is, in one embodiment, apically delivered through the apex of the left ventricle of the heart using a catheter system. In one aspect of the apical delivery, the catheter system accesses the heart and pericardial space by intercostal delivery. In another delivery approach, the catheter system delivers the prosthetic heart valve using either an antegrade or retrograde delivery approach using a flexible catheter system, and without requiring the rigid tube system commonly used. In another embodiment, the catheter system accesses the heart via a trans-septal approach.

In one non-limiting preferred embodiment, the stent body extends into the ventricle about to the edge of the open mitral valve leaflets (approximately 25% of the distance between the annulus and the ventricular apex). The open native leaflets lay against the outside stent wall and parallel to the long axis of the stent (i.e. the stent holds the native mitral valve open).

In one non-limiting preferred embodiment, the diameter should approximately match the diameter of the mitral annulus. Optionally, the valve may be positioned to sit in the mitral annulus at a slight angle directed away from the aortic valve such that it is not obstructing flow through the aortic valve. Optionally, the outflow portion (bottom) of the stent should not be too close to the lateral wall of the ventricle or papillary muscle as this position may interfere with flow through the prosthesis. As these options relate to the tricuspid, the position of the tricuspid valve may be very similar to that of the mitral valve.

In another embodiment, the prosthetic valve is sized and configured for use in areas other than the mitral annulus, including, without limitation, the tricuspid valve between the right atrium and right ventricle. Alternative embodiments may optionally include variations to the cuff structure to accommodate deployment to the pulmonary valve between the right ventricle and pulmonary artery, and the aortic valve between the left ventricle and the aorta. In one embodiment, the prosthetic valve is optionally used as a venous backflow valve for the venous system, including without limitation the vena cava, femoral, subclavian, pulmonary, hepatic, renal and cardiac. In this aspect, the cuff feature is utilized to provide additional protection against leaking.

Tethers

In one preferred embodiment, there are tethers attached to the prosthetic heart valve that extend, directly or indirectly, to one or more tissue anchor locations within the heart. In one preferred embodiment, the tethers extend downward through the left ventricle, exiting the left ventricle at the apex of the heart to be fastened on the epicardial surface outside of the heart. Similar anchoring is contemplated herein as it regards the tricuspid, or other valve structure requiring a prosthetic. There may be from 2 to 8 tethers which are preferably attached to the stent.

In another preferred embodiment, the tethers may optionally be attached to the cuff to provide additional control over position, adjustment, and compliance. In this preferred embodiment, one or more tethers are optionally attached to the cuff, in addition to, or optionally, in place of, the tethers attached to the stent. By attaching to the cuff and/or the stent, an even higher degree of control over positioning, adjustment, and compliance is provided to the operator during deployment.

During deployment, the operator is able to adjust or customize the tethers to the correct length for a particular patient's anatomy. The tethers also allow the operator to tighten the cuff onto the tissue around the valvular annulus by pulling the tethers, which creates a leak-free seal.

In another preferred embodiment, the tethers are optionally anchored to other tissue locations depending on the particular application of the prosthetic heart valve. In the case of a mitral valve, or the tricuspid valve, there are optionally one or more tethers anchored to one or both papillary muscles, septum, and/or ventricular wall.

The tethers, in conjunction with the cuff, provide for a compliant valve which has heretofore not been available. The tethers are made from surgical-grade materials such as biocompatible polymer suture material. Examples of such material include 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle. Upon being drawn to and through the apex of the heart, the tethers may be fastened by a suitable mechanism such as tying off to a pledget or similar adjustable button-type anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Further, it is contemplated that the prosthetic heart valve may optionally be deployed with a combination of installation tethers and permanent tethers, attached to either the stent or cuff, or both, the installation tethers being removed after the valve is successfully deployed. It is also contemplated that combinations of inelastic and elastic tethers may optionally be used for deployment and to provide structural and positional compliance of the valve during the cardiac cycle.

Pledget

In one embodiment, to control the potential tearing of tissue at the apical entry point of the delivery system, a circular, semi-circular, or multi-part pledget is employed. The pledget may be constructed from a semi-rigid material such as PFTE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex.

Tines/Barbs

In another embodiment the valve can be seated within the valvular annulus through the use of tines or barbs. These may be used in conjunction with, or in place of one or more tethers. The tines or barbs are located to provide attachment to adjacent tissue. In one preferred embodiment, the tines are optionally circumferentially located around the bend/transition area between the stent and the cuff. Such tines are forced into the annular tissue by mechanical means such as using a balloon catheter. In one non-limiting embodiment, the tines may optionally be semi-circular hooks that upon expansion of the stent body, pierce, rotate into, and hold annular tissue securely.

Retrieval System

In another embodiment, a retrieval system is contemplated for quickly removing the prosthetic valve during an aborted surgical deployment using minimally invasive cardiac catheter techniques. In this embodiment, the tether(s) would be captured by a catheter having a snare attachment. Once the tethers were captured, an intra-ventricular funnel attachment would guide the prosthetic valve into a collapsed, compressed conformation by pulling on the tethers, thus pulling the compressed prosthetic valve into the removal catheter for subsequent extraction.

To better assist understanding of the inventive subject matter, the following terms are given a more detailed definition.

Retrieval Guide Component

The retrieval guide component will be the point of attachment between the plurality of valve tethers, with points of attachment around the rim of the stent, and the single retrieval tether, which will be used both to anchor the valve to native heart tissue and to retrieve the valve when it is due for replacement. In a preferred embodiment, the guide will be of a diameter to fit snugly within the retrieval catheter, and will be bullet-shaped, cone-shaped, hooded or otherwise shaped, thus stabilizing the line of retraction evenly distributing the force of retraction among the tethers so that the valve is drawn towards the catheter directly. Direct, even force of retraction applied to each valve tether simultaneously will result in an even collapse of the expandable stent as it approaches the catheter, thus facilitating even retraction of the collapsed stent and valve.

Single Retrieval Tether

As stated, the single tether with either be integrated with or attached to the retrieval guide component, and will extend from such component to its anchored position in the native cardiac tissue, for example without limitation, the chordae tendineae, papillary muscle, heart wall or apex. Since the valve tethers will be able to distribute applied force among multiple components, it may be desirable for the single retrieval tether to be of a larger gauge than the valve tethers, and therefore able to withstand greater force for a longer period. A preferred embodiment utilizes super elastic Nitinol wire approximately 0.20" or greater in diameter. It is the single retrieval tether that will likely be engaged by the catheter during removal, and retraction of the single retrieval tether will, in turn, apply the retraction force necessary to both pull the full valve assembly into the catheter, and to collapse the valve assembly in so doing.

Stent

As stated, tubular stent may be an expandable laser cut stent or an expandable braided stent. Tubular stent may be constructed of Martensitic or super elastic metal alloys. Tubular stent may be compressed along its longitudinal axis and will fit into a catheter-based stent delivery system. When the tubular stent is delivered to the location where it is to be installed, it is expelled from the catheter by an obturator and deposited at the site where it is to be deployed. Referring to the stent body, it is contemplated as within the scope of the invention to include both laser cut stent technology and/or the braided stent technology. Where the cuff wire form is merely an extension of a braided stent and forms a unitary stent-cuff construction, the spindles are formed by heating a Nitinol™ stent on a mold to create the proper extension and angle necessary to establish the cuff or collar portion.

Where the stent is laser cut, the cuff wire form may be manufactured as a unitary laser-cut stent-cuff construction. In this embodiment, the cuff wire form and the stent are laser cut within the same overall manufacturing process. Where the cuff wire form is made separate from the stent and attached as a flat collar plate, the cuff wire form and stent may be manufactured/laser cut separately and attached using laser weld or other similar technique to create a non-fatiguing elastic stent-cuff joint capable of maintaining elastic compliance while it is deployed.

As noted, the rim may consist of an artificial transition point between the stent and the cuff where the stent has been heated to change the shape and angle of the topmost portion of the stent or the valve has been laser cut to create it's overall wire form, or the rim may consist of a constructed transition point such as a laser welded joint for attaching two component parts.

Once the cuff is covered by stabilized tissue, the loops provide the cuff the ability to travel or flex up and down, along the longitudinal axis; longitudinal defined by the lengthwise axis of the stent. As stated, this flexibility or compliance provides the prosthetic heart valve, specifically the cuff, upon being deployed within a patient's heart, the ability to conform to the anatomical shape of the left atrium, maintain the conforming shape during the cardiac cycle, and provide a tight seal against the atrial tissue adjacent the mitral valve aperture. This feature reduces or removes the guesswork that often accompanies the pre-surgical sizing of a mitral valve. By providing a better fit, this necessarily prevents blood from leaking around the implanted prosthetic heart valve.

The cuff tissue is thin, durable, and may be attached to the top, bottom, or both sides of the cuff.

The stent may include stent liner made from tissue and that may optionally function to support the leaflets of the valve. This liner is contemplated as being made of tissue or biocompatible material as disclosed herein. The stent may also optionally have a inner stent liner and/or an outer (surface) stent liner. One embodiment provides a two-piece structure that includes leaflets. In this embodiment, the leaflet structure may have a mitral valve shape, a "saddle shape" that constitutes a hyperbolic paraboloid to afford one specific form of structural integrity.

Cuff

Prosthetic heart valve also includes cuff. The cuff is formed from a cuff wire form that is covered by, in one embodiment, stabilized tissue. In one embodiment, the cuff wire form is an extension of the stent itself, where the stent has been heated and manipulated upon a form to create the extended spindles of the flat, collar plate of the cuff. In another embodiment, the cuff wire form is made separate from the stent and attached as a flat collar plate constructed to include an inner rim and an outer rim, with independent loops of wire that create lobes or segments extending axially around the circumference of the inner rim, the joint where the cuff meets the tubular stent. The combination of the stabilized tissue of the cuff covering and wire cuff spindles, make up a cuff structure and provide a semirigid form that assists in the sealing of the cuff against the atrial trabeculations and tissue within and adjacent to the mitral annulus.

In one example, the cuff is formed from the stent by heating and shaping. In another example, the cuff and stent are formed from two joined pieces. The cuff spindles may vary in design size and shape. In one example, every other spindle is longer that the adjacent showing an alternating pattern. This provides an advantage of additional coverage and compliance of various cuff designs, in combination with how tethers are pulled and shortened to adjust or move the prosthetic valve towards and within the valvular annulus where it will be seated, adjusted, and fastened in place to complete the deployment. In another variation of one preferred embodiment of the present invention where the spindles do not alternate, but rather two spindles on either side create an elongated cuff for a prosthetic valve where this provides an advantage.

The cuff and stent body may be formed in such a manner to create various positions, e.g. angles, for the cuff. The angular relationship between the cuff and the stent function to seal the prosthetic heart valve against the mitral valve aperture and prevent leaking. In one embodiment, the angle of the cuff may also include a more acute inverted-funnel shaped angle. Although not limiting, in one example, the angle is 60 degrees. In another, the angle is approximately a perpendicular angle. In another example, a more obtuse funnel-shaped angle is provided, e.g. 150 degrees, in relation to the longitudinal axis of the stent.

Tines or barbs can facilitate the attachment to the tissue, such as the mitral annulus or the tricuspid, annulus, where barbs may be attached at the neck of the prosthetic valve where the cuff meets or transitions to the stent body.

In one embodiment, a specific form of hooked barb where the hooked barb is adjusted to provide an opening between the barb and the stent body where an operator would direct the annular tissue to assist with seating the valve. Upon placing the prosthetic valve 110 there, a balloon catheter or other expansion means is inserted into the stent to expand the internal diameter, thus causing the hooked barbs to rotate back inwards toward the stent, thus capturing and locking the annular tissue to the stent body.

Pillow Cuff

In one embodiment, the space between the cuff tissue and cuff dacron liner (inside-outside) may be used to create a cuff that is swellable or may be inflated and which provides an enhanced level of sealing of the cuff against the atrial trabeculations and annular tissue. This allows for the delivery of a prosthetic valve such as a mitral valve, that has a small cuff, that fits within a steerable catheter, but where, upon delivery, the cuff enlarges to establish a much greater seal than heretofore available.

Leaflet

Leaflet assembly is a separate but integrated structure that is disposed within the stent. Leaflet assembly functions to provide the structure upon which the valve leaflets or cusps are located. Leaflet assembly may be made entirely of stabilized tissue or it may be a combination wire and tissue structure. Where leaflet assembly is composed entirely of tissue, it is contemplated that the leaflet assembly, leaflet support structure, and leaflets or cusps are made from tissue. It is contemplated as within the scope of the invention that different qualities of stabilized tissue, i.e. thin or thick, structurally rigid or flexible as it may be, may be used for the different components of the cuff covering, the stent covering, the leaflet assembly and the leaflets. Where leaflet assembly is composed of wire and tissue, it contemplated that assembly or support(s), or both, may be made from wire, and the cusps would necessarily be made from tissue.

The leaflet structure may have a leaflet structural wire support to provide spring-like tension to assist in the proper orientation of the leaflets once the prosthetic heart valve is expanded from a compressed stored shape to its final functional shape. Three junctions (commissural tips) and the three arched wires (of this embodiment) of the leaflet structural wire support are contemplated. Leaflet wire form is preferably constructed as a single wire that is molded, twisted, and/or manipulated into the final shape. In another embodiment, the leaflet wire form is series of wires that have been attached, e.g. laser welded. In one embodiment, the junctions move independently of the stent. Specifically, the junction end of the leaflet assembly may not be attached to the stent, but only the upper portion. Having unattached junctions with the ability to flex inward and, more importantly, expand outward, gives the leaflet wire form the structural ability to collapse when compressed and expand when deployed. The ability to compress and expand independently of one another, relieves mechanical stresses on the tissue.

Tethers

According to the present invention, the tether(s) may be used for anchoring, but also many other methods. One embodiment is that they be used for temporary positioning. Another embodiment is a tether used for delivery to the correct location within the valve annulus.

The tether may be attached to the stent body or may be attached to the cuff, or both.

The use of radio-opaque markers is contemplated to assist with adjustments under fluoroscopic visualization.

The tether(s) may be used for positioning during surgery, and then for re-adjustment after surgery, e.g. 30 days later.

The tether(s) may be used for positioning or delivery and then allowed to be ingrown.

Tubular stent includes a plurality of tether attachments upon which a tether may be connected. In a preferred embodiment, there is a single tether system for anchoring the prosthetic mitral valve within the left ventricle. In another embodiment there are multiple tether attachments which are integrated into the stent.

It has been found in in vivo surgical testing that proper tethering is an extraordinarily difficult proposition. By providing the surgeon the ability to control, adjust, tighten, the cuff geometry relative to the stent geometry, many options are provided that were not heretofore known to be available in the prior art.

Cycle testing of tether materials is critical to determine if they can withstand prolonged cardiac forces. For example, testing up to 800 million cycles is not uncommon, especially when the human heart at 60 beats per minute, beats 31,536,000 (31 million+cycles) per year.

Tether Problems

It is now known that tethers that are not affixed to either the heart or the prosthetic valve, in a correct manner, can suffer catastrophic failure and break, even though manufacturers specifications would appear to indicate that tether materials, such as dacron or nitinol, should be able to withstand such forces. Additionally, if the tether is not attached to the prosthetic valve at the correct spot(s), the tether may fail to anchor, or may instead put all the anchoring onto one tether while not utilizing any others, or may allow the prosthetic to come loose within the heart with attendant morbidity for the patient.

Epicardial Tethering

Tethers in this embodiment extend through the heart muscle and are attached to securing device, here shown as a pledget placed on the epicardial surface and having tethers fastened thereto.

In this embodiment, the pledget performs the function of an anchor to which the tethers are attached. Tethers are strung through the left ventricle apex and pulled downward to seat prosthetic valve 110 in the atrial valve area. The completely installed prosthetic valve is held in the left atrium by the cuff and secured to the apex of the heart by tethers. The tethers may be held in place by a securing device which in this aspect of the invention is a pledget that the tethers are threaded through and secured against, i.e. by tying a knot or using a cinching feature.

Attaching to the Stent Body

Stents may be fashioned having articulating loops that extend and allow for tethers to be attached. If multiple tethers a attached to the stent body, for example, three (3) tethers, it is possible for the interventionalist or surgeon to pull one or the other of the tethers in order to seat the valve properly and stop perivalvular leaking Once the tethers have been adjusted to the correct length and fastened to the ventricular apex, or cardiac muscle, the new valve should be fully operational.

In other embodiments contemplated herein, however, problems may occur with uneven loading of the tethers, and as a consequence, possible tether failure. Accordingly, it is contemplated that an structure resembling an inverted tripod, may be utilized, or inverted "umbrella frame" if multiple stent tethers are used, either with multiple tethers connected to the stent body and a single tether connecting the valve tethers to the cardiac anchoring fixation location via the retrieval guide, whether it is at the apex with a pledget, or attached to cardiac native structures. It is contemplated as within the scope of the invention that a single tether could be fashion to anchor three or more points on the stent body, create a fixed or traveling knot at an intersection below the stent body, and continue down through the ventricle or other space to an anchoring spot.

In another embodiment, a ring structure is used to gather the stent tethers to a single point, and an anchoring tether is attached to the tether-ring, which is then anchored within the heart, e.g. apical pledgett, etc. Nitinol is contemplated in a preferred embodiment, but other materials may be used, especially biocompatible metals, alloys, polymers, and structures fabricated from natural sources, such as pericardial tissue.

Tether Clips or Keys

In another embodiment, it is contemplated as within the scope of the present invention, that the stent body and the tether(s) may be connected using various interlocking or interconnecting components. In one embodiment, either the tether or the stent loop may be fitted with a male or female component with the counterpart being attached to the other part, thus allowing a secure fit during deployment without necessitating additional strain/damaging forces on the tether or tether structures.

In one example, a small part may be sutured to the stent body where the part has a fitted region for accepting an interlocking piece of a complimentary piece that is attached to a tether. Nonlimiting examples include a ball and socket system, a T and socket system, and so forth.

The use of capturing loops and other endoscopic techniques for bringing these components together and connecting them is within the standard skill level of physicians performing these catheter-based techniques.

Delivery

When a prosthetic heart valve according to be retrieved according the present invention is deployed within a valve aperture of the heart, it is anchored, between where it is seated or lodged by the atrial cuff and the valve tethers connected to the retrieval guide, which is then tethered via the single retrieval tether to cardiac tissue, for example, to the apex of the heart, either with or without a pledget.

When anchored at the apex, the single retrieval tether is tied off at the apex of the heart after deployment of the prosthetic valve using closure/tissue-buttressing material. The anchoring system of the prosthetic valve may have the retrieval tether threaded through the left ventricle apex and through a partially installed pledget. Tissue buttressing material may optionally be in one embodiment a pledget felt. Other systems for anchoring the retrieval tether to the native heart tissue may include pins, hooks, clips, or similar devices either integrated with or attached to the retrieval tether.

It is contemplated that the prosthetic valve delivery catheter will access the left atrium via the left ventricle by way of a lateral trans-ventricular wall approach through the lateral wall of the left ventricle of the heart.

In another embodiment, the delivery catheter is advanced through to the tricuspid valve and into the right atrium for deployment of the prosthetic heart valve.

DESCRIPTION OF THE FIGURES

Bulletnose Retrieval Device

Figure 1:
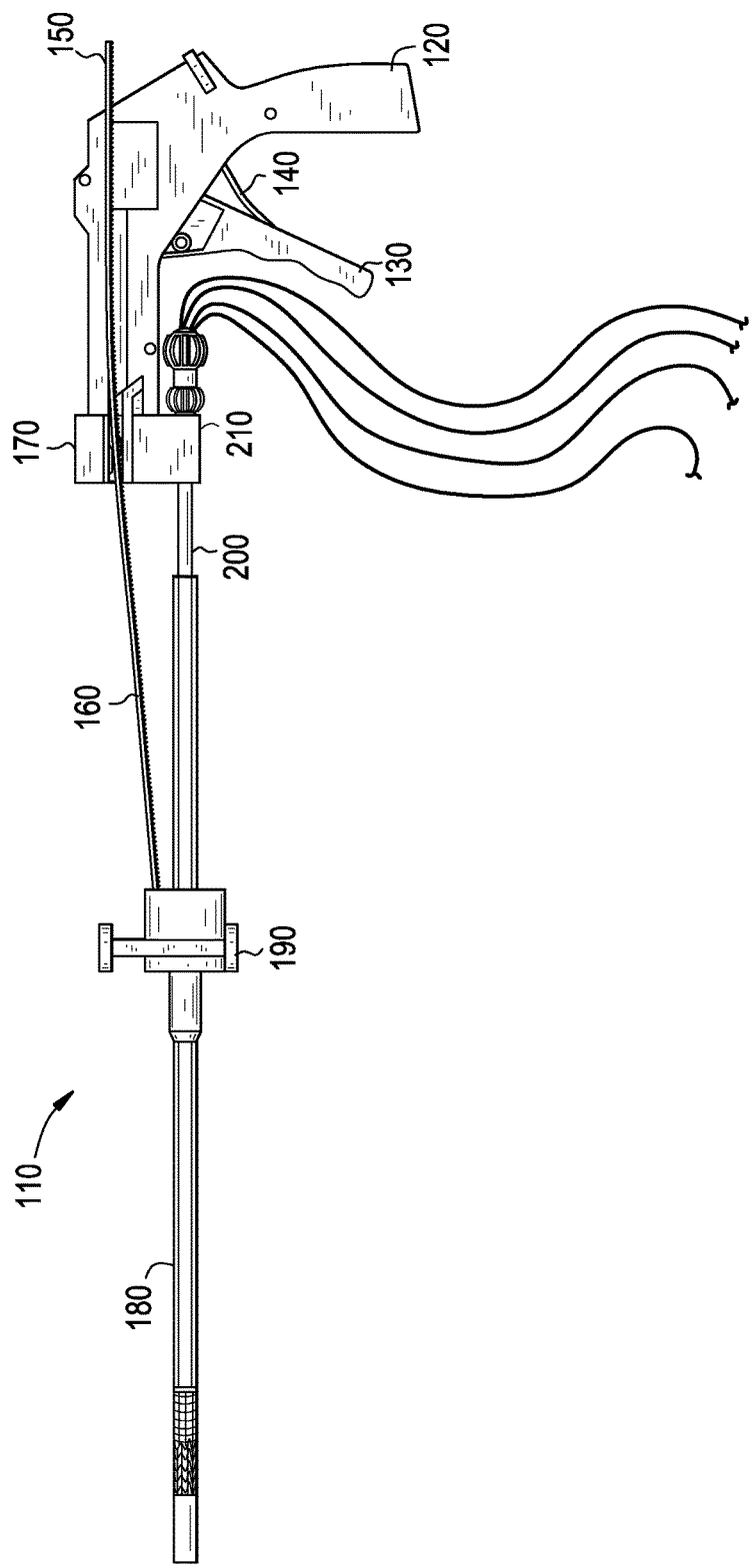
Referring now to FIG. 1, in a components view, evidences the delivery apparatus for a transcatheter cardiac valve replacement.

Referring now to the FIGURES, FIG. 1 shows in a components view, the delivery apparatus 110 for a transcatheter mitral valve replacement, comprising a handle 120 having an actuator 130 and an actuator spring 140. A tensioning unit 150 is mounted for reciprocal motion responsive to the operation of the actuator 130. A traveller strap 160 is removably mounted within a strap mount 170 of the tensioning unit 150. A catheter 180 is removably held by a catheter mount 190 which is connected to a distal end of the traveller strap 160. A pusher unit 200 has a distal end that is partially disposed within said catheter 180, and a proximal end that engages a pusher mount 210 on the handle 120.

Figure 2:
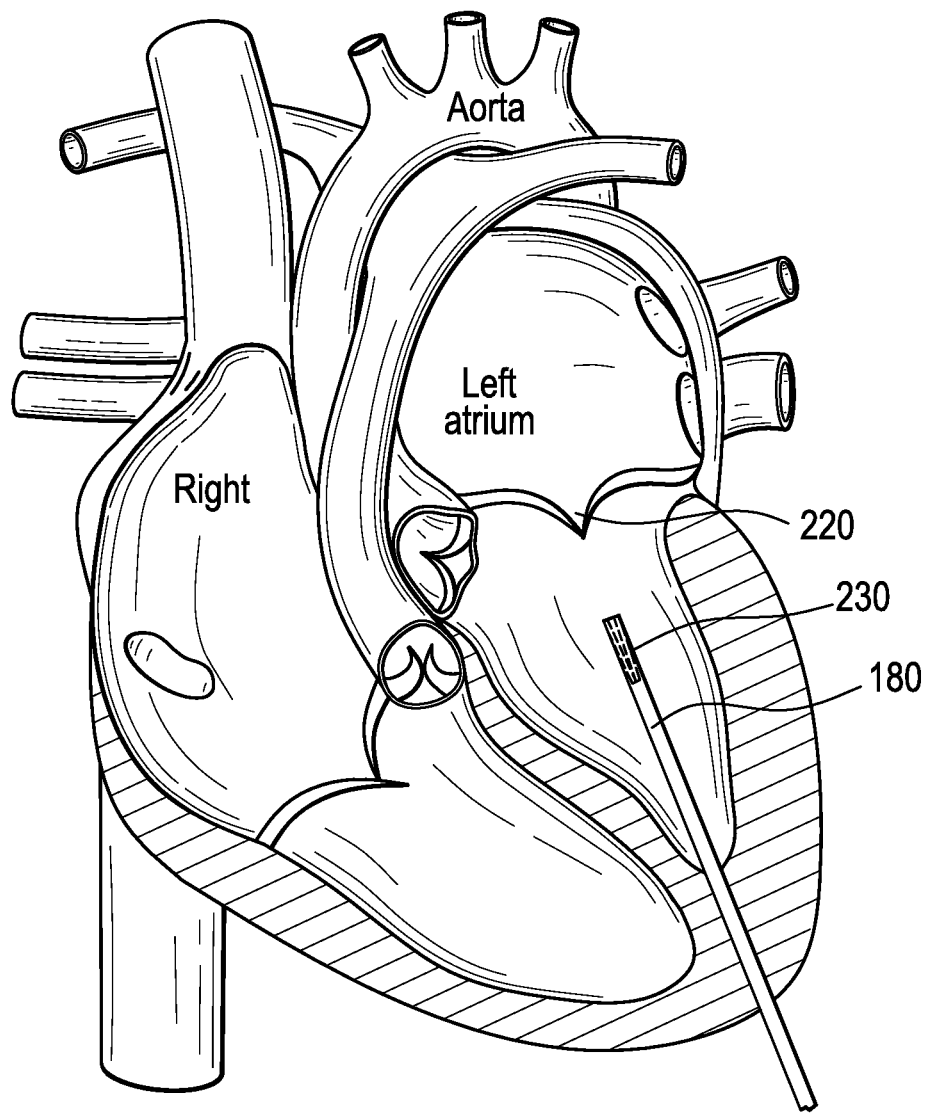
Referring now to FIG. 2, a line drawing evidencing an apical delivery of a prosthetic mitral valve via catheter.

Referring now to the FIGURES, FIG. 2 shows catheter 180 entering the left ventricle through the apex of the heart and moving towards delivering stent 230 into the native mitral valve 220.

Figure 3:
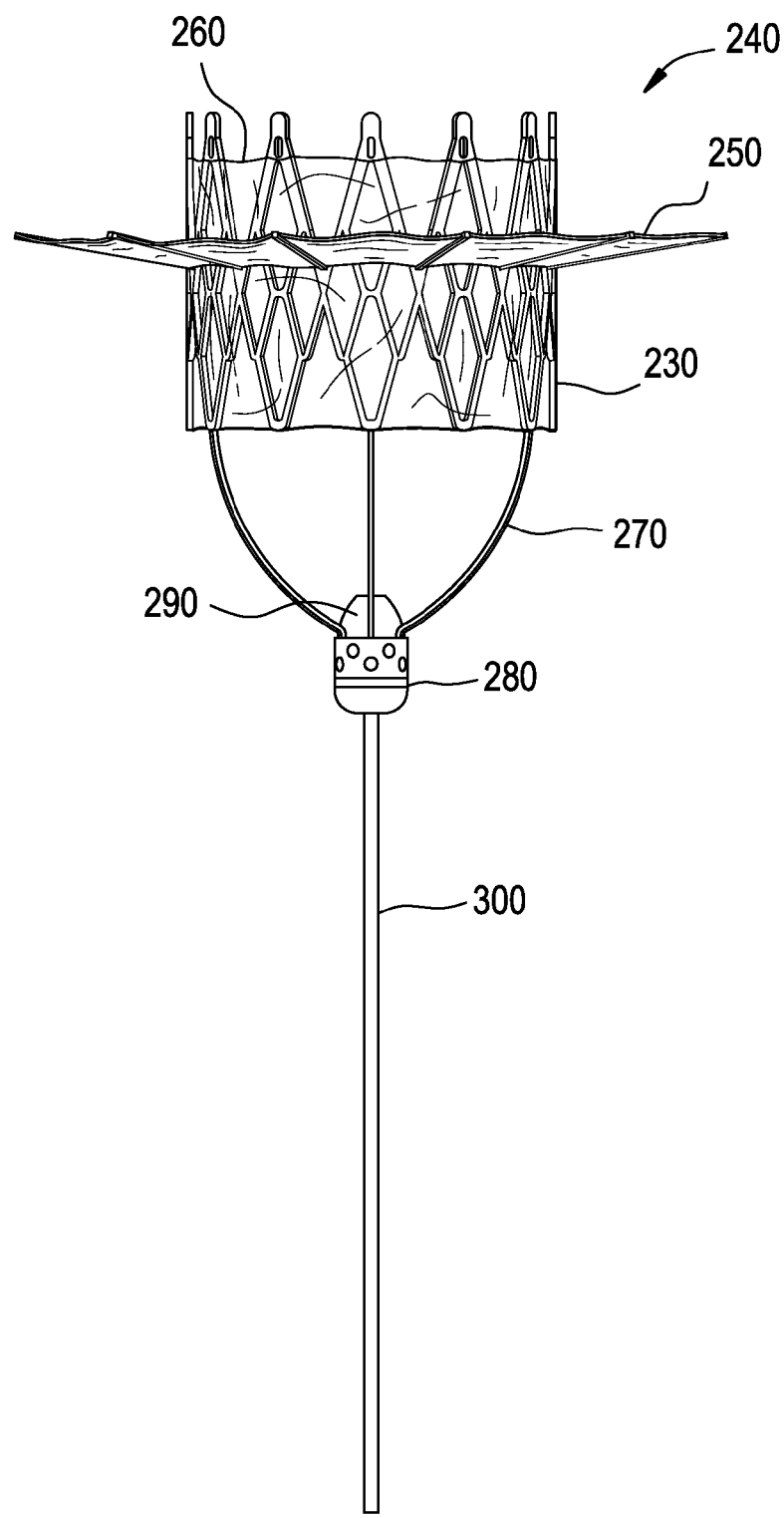
Referring now to FIG. 3, a line drawing evidencing a side view a tissue or fabric-covered metal stent, comprising a cuff component, with a plurality of valve tethers attached at regular intervals to the bottom thereof, such tethers connected at regular intervals to the proximal end of a retrieval guide component, with a single, wider-gauge retrieval tether emanating from the distal end of the bullet shaped component.

Referring now to the FIGURES, FIG. 3 shows in a component view, a side view of tethered stent assembly 240 for transcatheter mitral valve replacement, comprising stent body 230 covered by fabric or tissue 260, integrated with and surrounded by cuff component 250, which is also covered by covering 260, further integrated with the proximal end of each of a plurality of valve tethers 270, wherein the distal end of each tether 270 is integrated at equal intervals around the rim of perforated ring 280, which ring is integrated with and surrounds bullet-shaped component 290, wherein the conical, proximal end of such component 290 faces towards stent body 230, while the flat, distal end of component 290 faces away from stent body 230 and is attached to the single, large-gauge tether 300. In this figure, the totality of assembly 240, other than the covering 260, is shown as a single, integral, laser-cut metallic body, with cuff component 250 located around the midway point of stent body 230, with ring 280 and bullet-shaped component 290 combining to form a retrieval guide, and with all tethers pulled tight.

Figure 4:
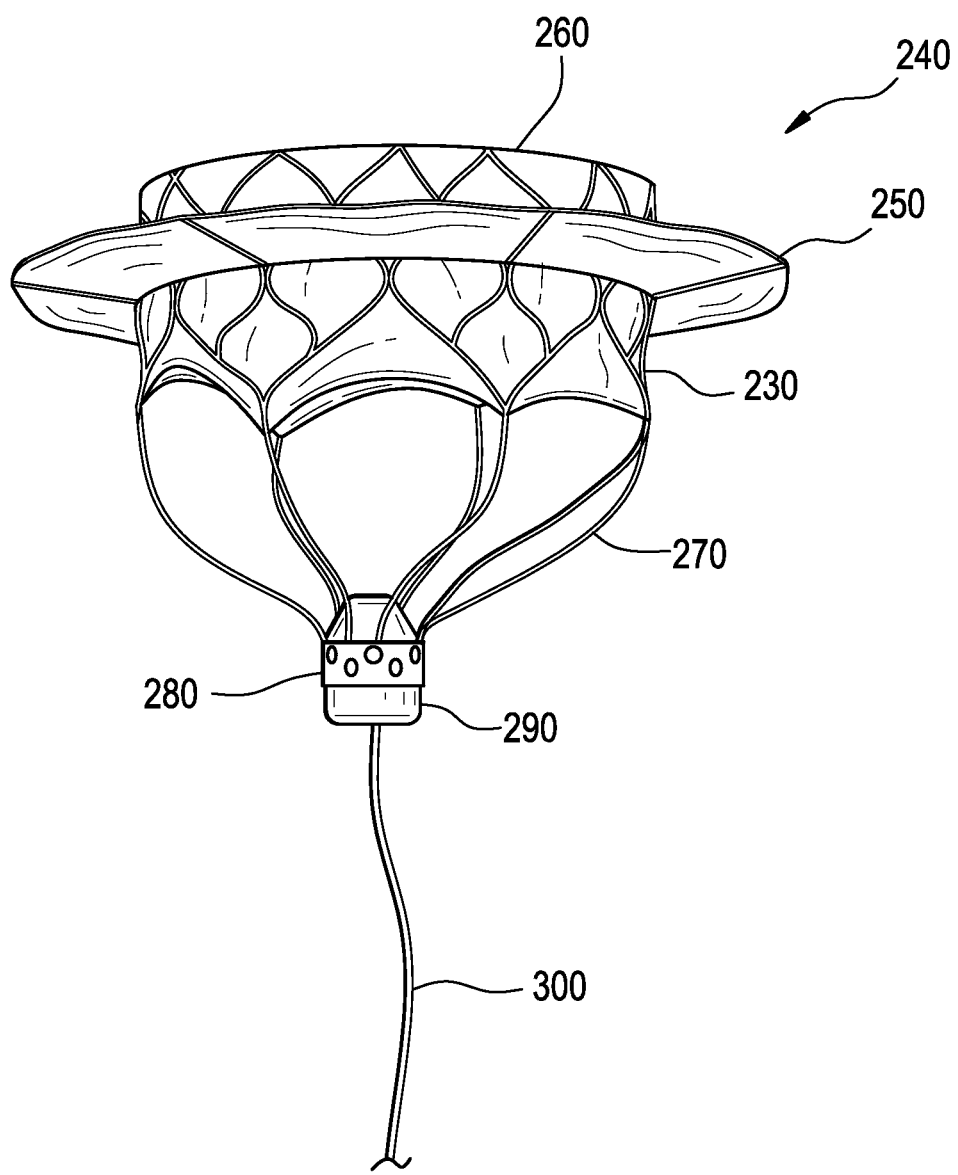
Referring now to FIG. 4, a line drawing evidencing a lower side perspective view of the assembly as shown in FIG. 3.

Referring now to the FIGURES, FIG. 4 shows in a component view, a perspective view of the tethered stent assembly 240 for transcatheter mitral valve replacement, comprising stent body 320 covered by fabric or tissue 260, integrated with and surrounded by cuff component 250, which is also covered by covering 260, further integrated with the proximal end of each of a plurality of tethers 270, wherein the distal end of each tether 270 is integrated at equal intervals around the rim of perforated ring 280, which ring is integrated with and surrounds bullet-shaped component 290, wherein the conical, proximal end of such component 290 faces towards stent body 230, while the flat, distal end of component 290 faces away from stent body 230 and is attached to the single, large-gauge tether 300. In this figure, the tethers appear loose.

Figure 5:
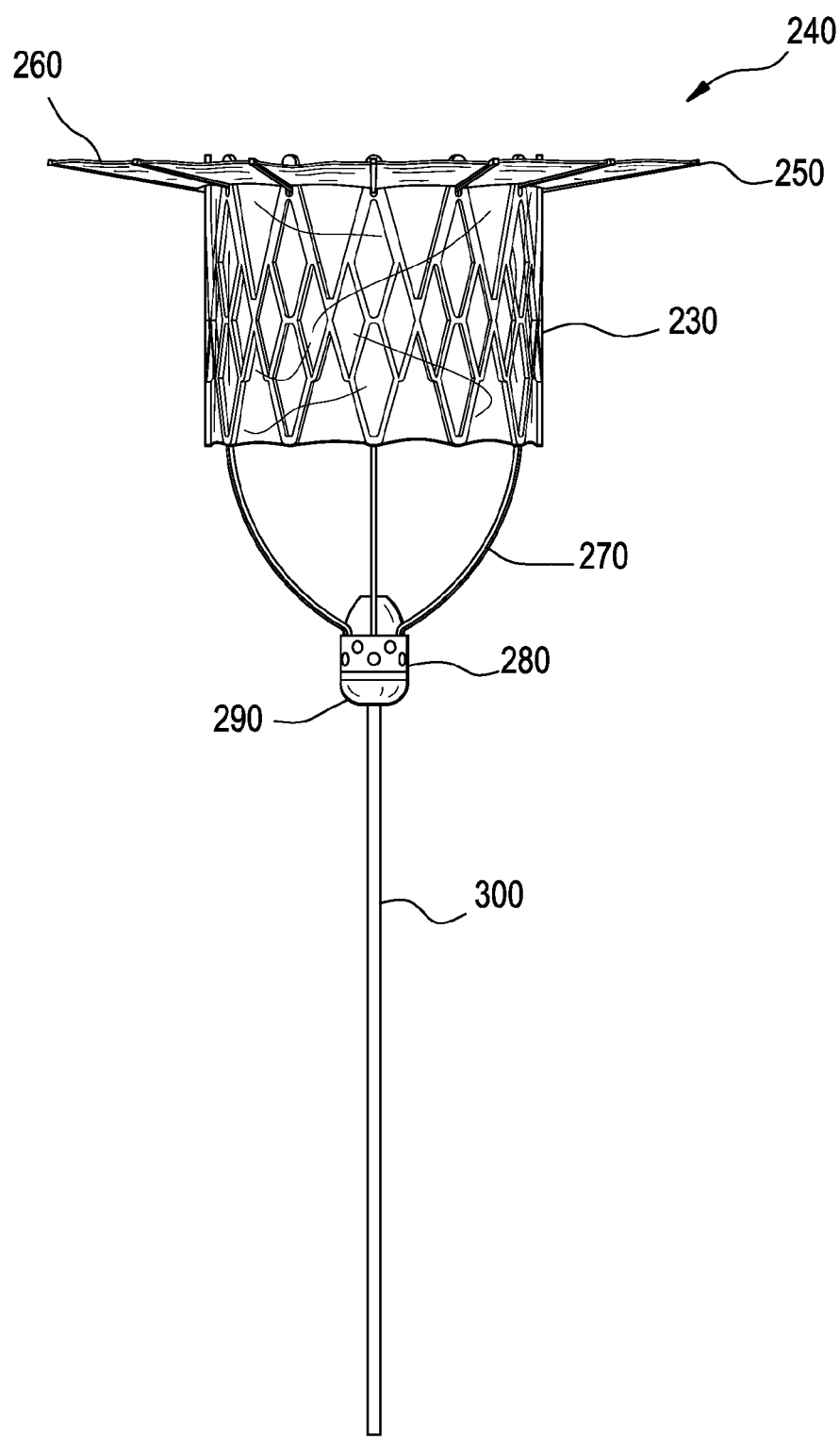
Referring now to FIG. 5, a line drawing evidencing a side view of the assembly as shown in FIG. 3, with the cuff component adjusted to the upper edge of the stent.

Referring now to the FIGURES, FIG. 5 shows in a component view, a side view of tethered stent assembly 240 for transcatheter mitral valve replacement, comprising stent body 230 covered by fabric or tissue 260, integrated with and surrounded by cuff component 250, which is also covered by covering 260, further integrated with the proximal end of each of a plurality of tethers 270, wherein the distal end of each tether 270 is integrated at equal intervals around the rim of perforated ring 280, which ring is integrated with and surrounds bullet-shaped component 290, wherein the conical, proximal end of such component 290 faces towards stent body 230, while the flat, distal end of component 290 faces away from stent body 230 and is attached to the single, large-gauge tether 300. In this figure, ring 280 and bullet-shaped component 290 combine to form a retrieval guide, all tethers are pulled tight and cuff component 250 has been located just beneath the upper rim of the stent body 230.

Figure 6:
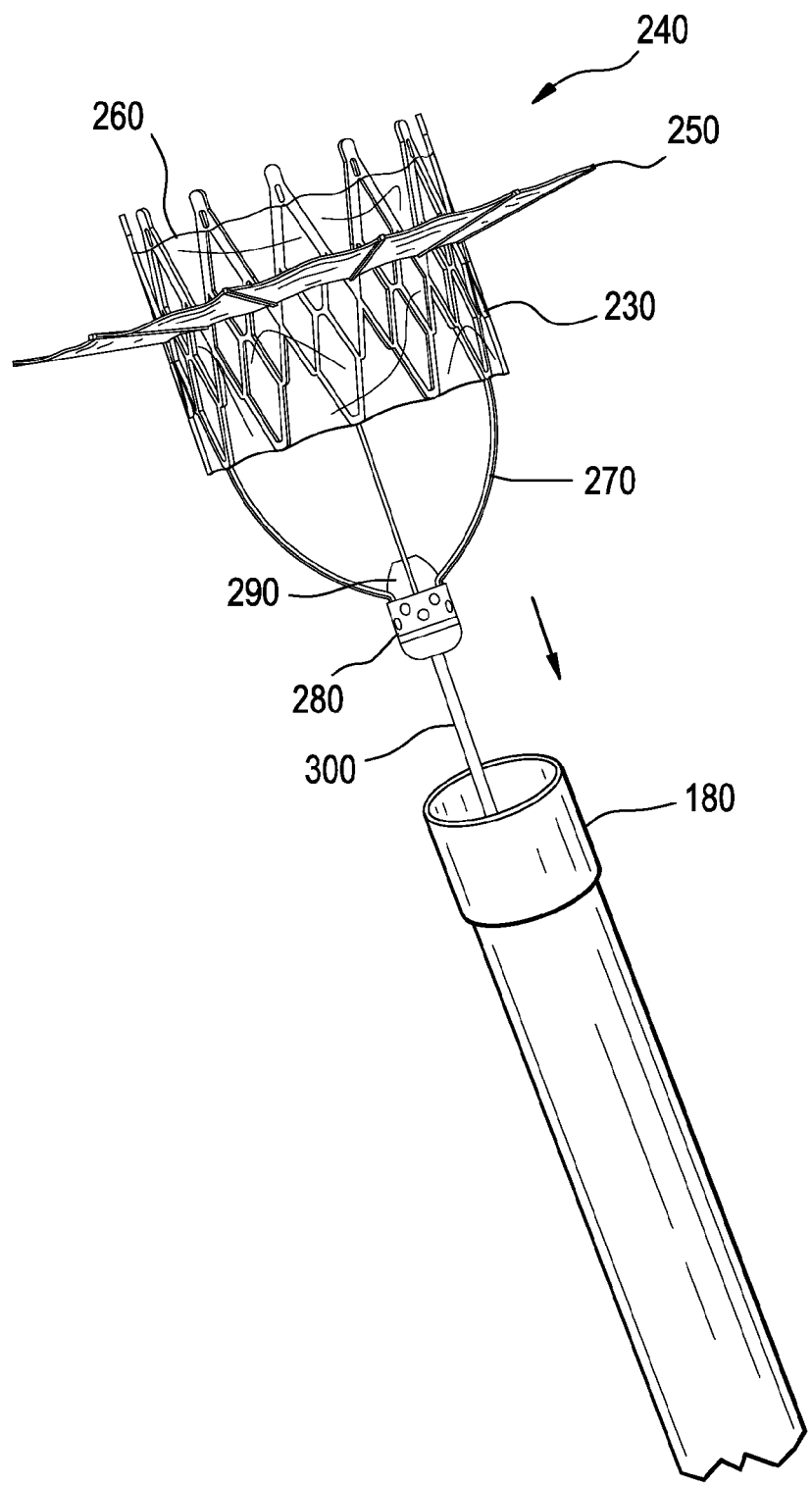
Referring now to FIG. 6, a line drawing evidencing a perspective view of the assembly of FIG. 3, wherein the single retrieval tether is being used to draw the assembly downward into a catheter.

Referring now to the FIGURES, FIG. 6 shows in a component view, a side view of tethered stent assembly 240 for transcatheter mitral valve replacement, comprising stent body 230 covered by fabric or tissue 260, integrated with and surrounded by cuff component 250, which is also covered by covering 260, further integrated with the proximal end of each of a plurality of tethers 270, wherein the distal end of each tether 270 is integrated at equal intervals around the rim of perforated ring 280, which ring is integrated with and surrounds bullet-shaped component 290, wherein the conical, proximal end of such component 290 faces towards stent body 230, while the flat, distal end of component 290 faces away from stent body 230 and is attached to the single, large-gauge tether 300. In this figure, ring 280 and bullet-shaped component 290 combine to form a retrieval guide, large-gauge tether 300 extends into delivery catheter 180 and is being pulled to retract stent assembly 240 into catheter 180.

Figure 7:
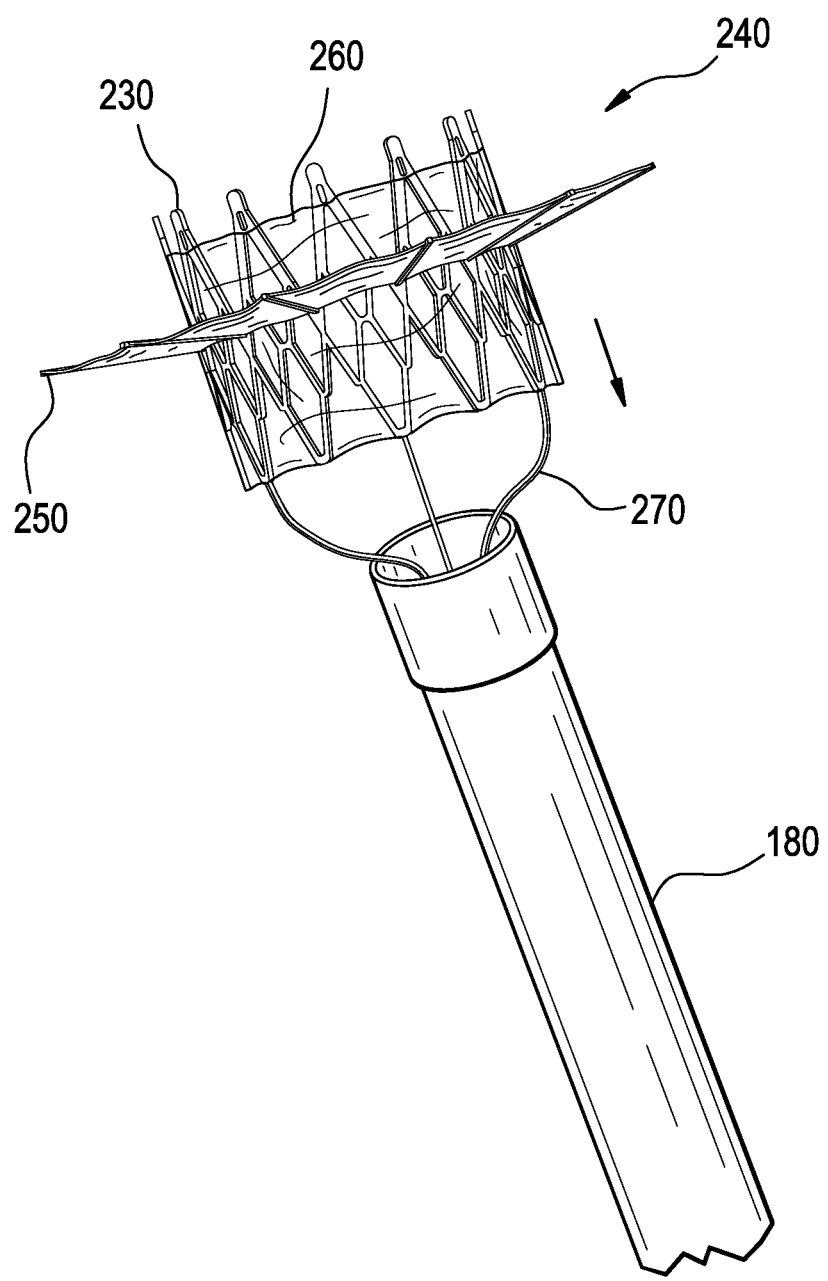
Referring now to FIG. 7, a line drawing evidencing a perspective view of the assembly of FIG. 3, wherein the single tether (not visible) has been drawn within a catheter and the connecting wires are subsequently being drawn within the catheter.

Referring now to the FIGURES, FIG. 7 shows in a component view, a side view of tethered stent assembly 240 for transcatheter mitral valve replacement, comprising stent body 230 covered by fabric or tissue 260, integrated with and surrounded by cuff component 250, which is also covered by covering 260, further integrated with the proximal end of each of a plurality of tethers 270. In this figure, each tether 260 extends into catheter 180 and is being pulled, via perforated ring 280 and bullet-shaped component 290 combining to form the retrieval guide (not shown) and large-gauge tether 300 (not shown) to retract stent assembly 240 into catheter 180.

Figure 8:
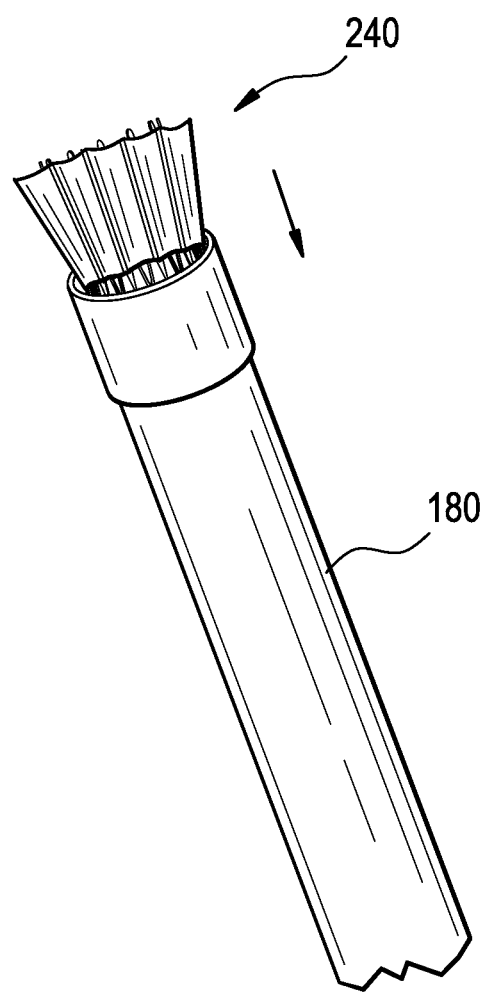
Referring now to FIG. 8, a line drawing evidencing a perspective view of the assembly of FIG. 3, wherein the stent and cuff have collapsed upward and are being drawn within a catheter.

Referring now to the FIGURES, FIG. 8 shows in a component view an almost fully-collapsed tethered stent assembly 240 in the final stage of retraction into catheter 180.

Figure 9:
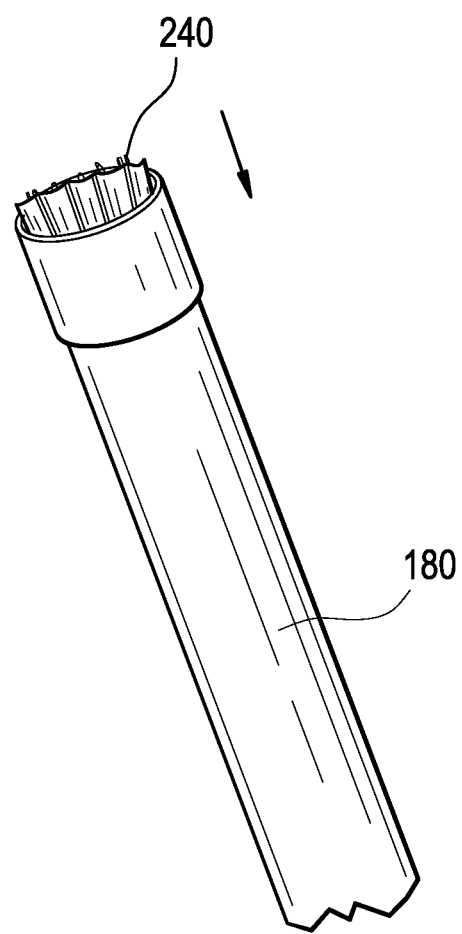
Referring now to FIG. 9, a line drawing evidencing a perspective view of the assembly of FIG. 3, wherein the stent and cuff have collapsed upward and have been fully drawn within a catheter.

Referring now to the FIGURES, FIG. 9 shows in a component view a collapsed tethered stent assembly 240 fully retracted within catheter 180.

Figure 10:
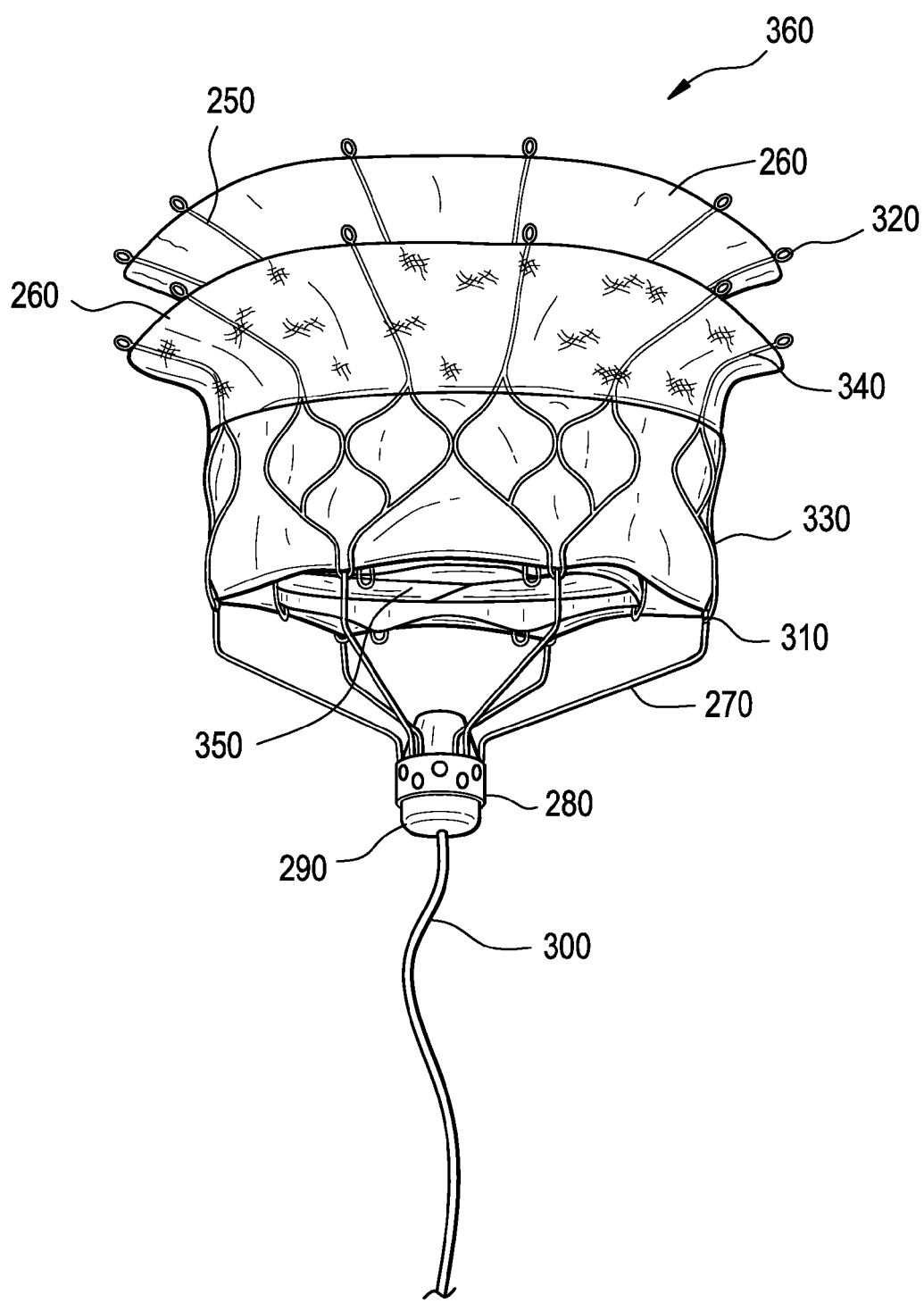
Referring now to FIG. 10, a line drawing evidencing a perspective view of the assembly of FIG. 5, further comprising a second covered metal stent and cuff attached to the outside of the first covered metal stent, and a fabric or tissue valve centered within the inner stent.

Referring now to the FIGURES, FIG. 10 shows in a component view, a perspective view of the tethered double stent assembly 360 for transcatheter mitral valve replacement, comprising stent body 230 (not shown) covered by fabric or tissue 260, integrated with and surrounded by cuff component 250, also covered by covering 260, surrounded by and integrated with outer stent body 330, also covered by covering 260, integrated with and surrounded by outer cuff component 340, wherein each of cuff 250 and outer cuff 340 further comprise a plurality of eyelets 320 at regular intervals around their upper rims, such outer stent body 330 further comprising tether connection loops 310 at regular intervals around its lower rim, wherein each connection loop 310 is attached to the proximal end of a tether 270, wherein the distal end of each tether 270 is integrated at equal intervals around the rim of perforated ring 280, which ring is integrated with and surrounds bullet-shaped component 290 to form a retrieval guide, wherein the conical, proximal end of such component 290 faces towards stent body 230, while the flat, distal end of component 290 faces away from stent body 230 and is attached to the single, large-gauge tether 300. In this figure, (i) each eyelet 320 provide a potential point for suturing or other attachment to the native tissue; and (ii) tethers 270 may be integrated with outer cuff 330, or may be tied, twisted or otherwise attached thereto via connection loops 310.

Figure 11:
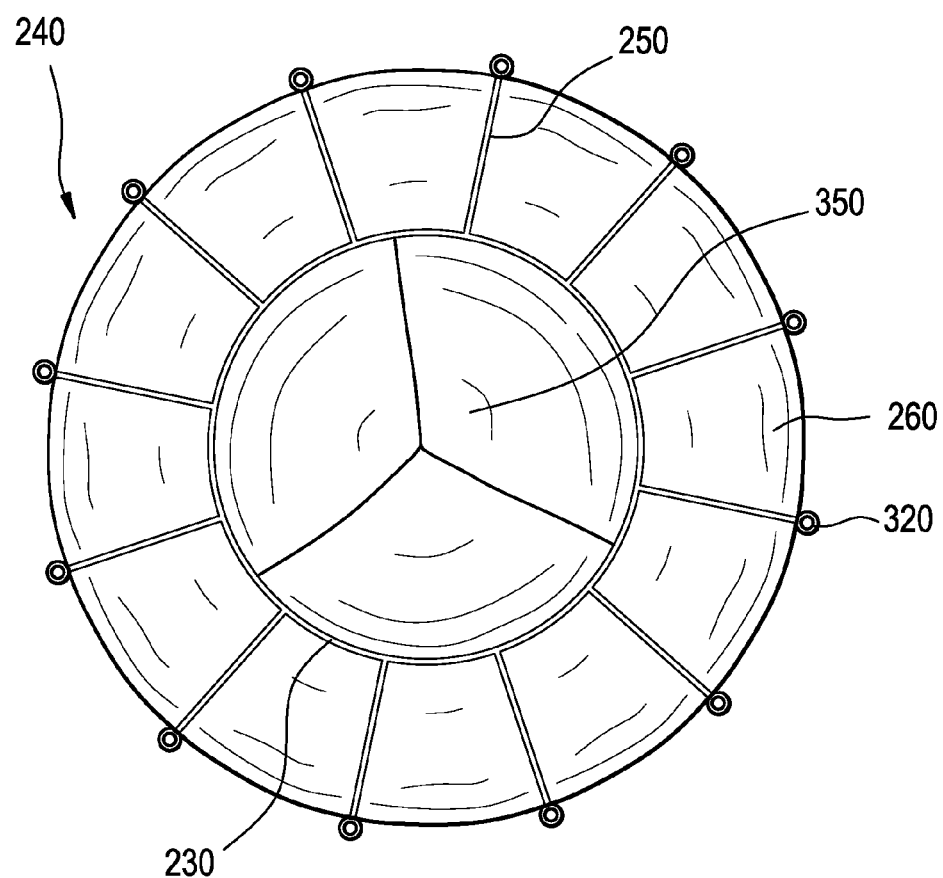
Referring now to FIG. 11, a line drawing evidencing a top view of the assembly as shown in FIG. 3.

Referring now to the FIGURES, FIG. 11 shows in a component view, a top view of the tethered stent assembly 240 for transcatheter mitral valve replacement, comprising cuff component 250, covered by fabric or tissue covering 260 and surrounding stent body 230, which contains integrated prosthetic valve 350. Cuff eyelets 320 are integrated at regular intervals around the rim of cuff component 250.

Figure 12:
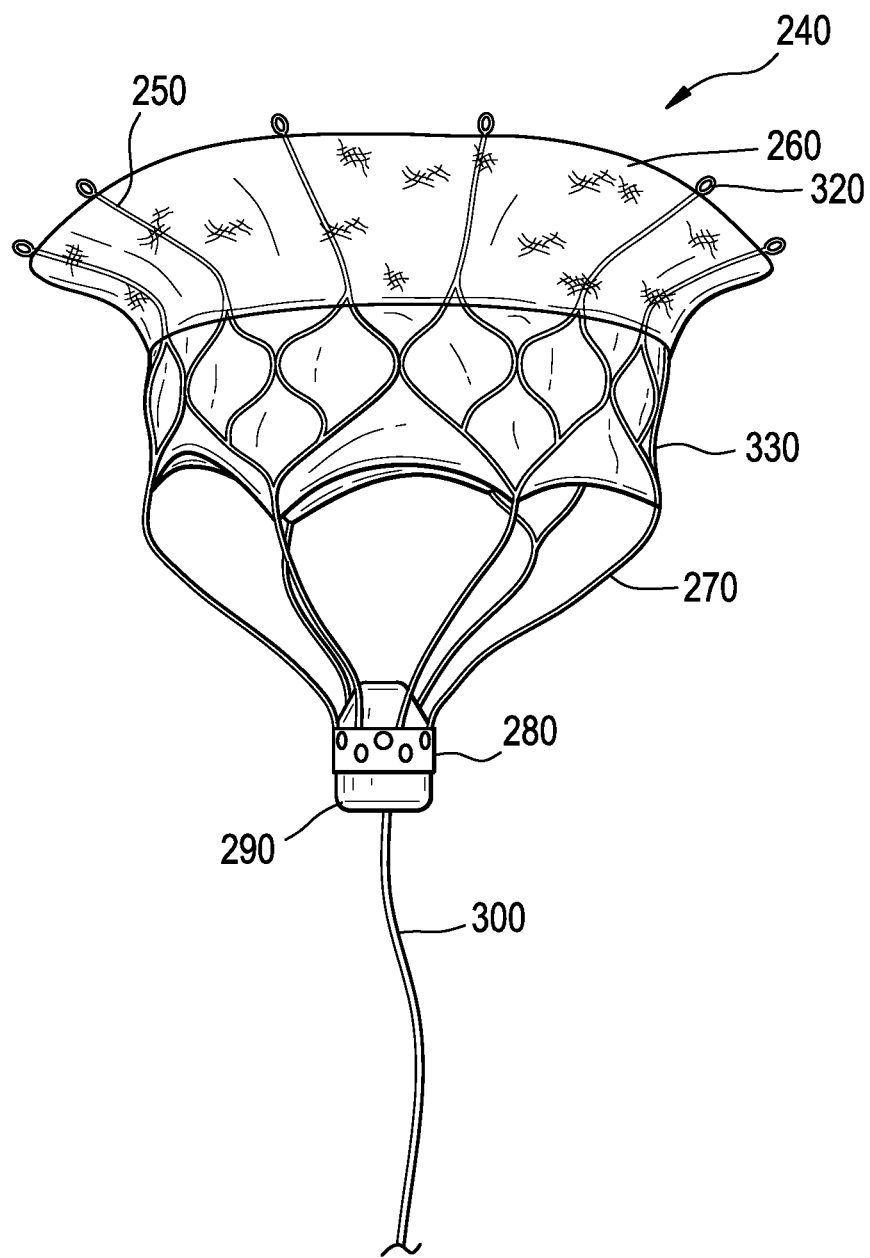
Referring now to FIG. 12, a line drawing evidencing a side view of the assembly as shown in FIG. 5, wherein the cuff is extended upward and the tethers are slack.

Referring now to the FIGURES, FIG. 12 shows in a component view, a perspective view of tethered stent assembly 240 for transcatheter mitral valve replacement, comprising stent body 230 covered by fabric or tissue 260, integrated with and surrounded by cuff component 250, which is also covered by covering 260 and further comprises eyelets 320 at regular intervals around the cuff rim, wherein cuff 250 is further integrated with the proximal end of each of a plurality of tethers 270, wherein the distal end of each tether 270 is integrated at equal intervals around the rim of perforated ring 280, which ring is integrated with and surrounds bullet-shaped component 290 to form a retrieval guide, wherein the conical, proximal end of such component 290 faces towards stent body 230, while the flat, distal end of component 290 faces away from stent body 230 and is attached to the single, large-gauge tether 300. In this figure, the totality of assembly 240, other than the covering 260, is shown as a single, integral, metallic body with all tethers appearing loose.

Figure 13:
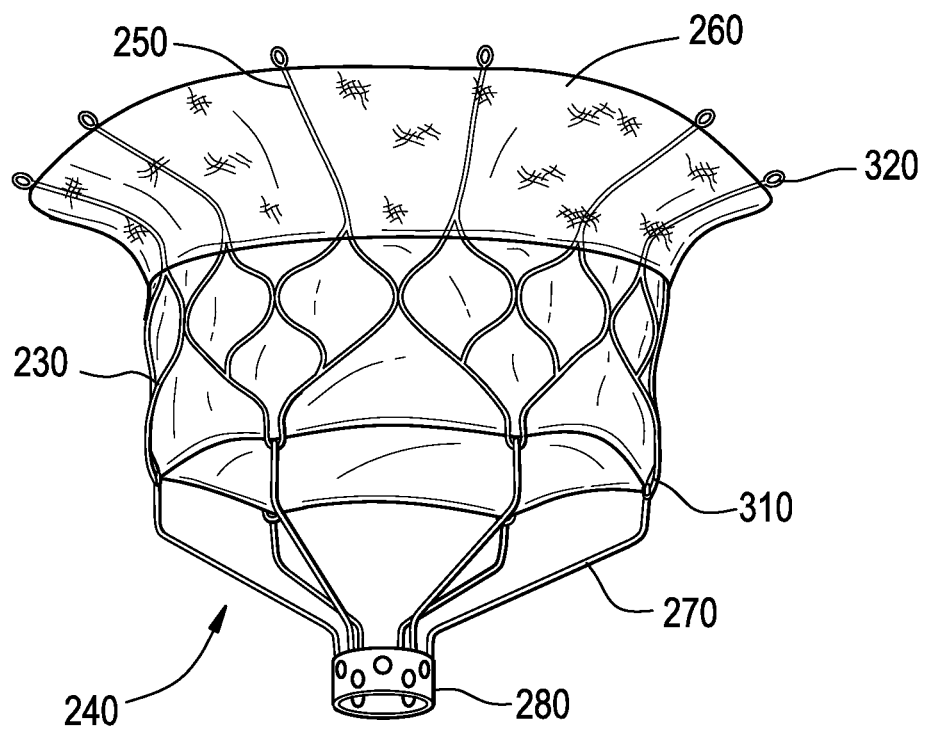
Referring now to FIG. 13, a line drawing evidencing the assembly as shown in FIG. 12, wherein the bullet-shaped guide component and single large-gauge tether components have been removed.

Referring now to the FIGURES, FIG. 13 shows in a component view, a perspective view of tethered stent assembly 240 for transcatheter mitral valve replacement, comprising stent body 230 covered by fabric or tissue 260, integrated with and surrounded by cuff component 250, which is also covered by covering 260 and further comprises eyelets 320 at regular intervals around the cuff rim, wherein cuff 250 is further integrated with the proximal end of each of a plurality of tethers 270, and wherein the distal end of each tether 270 is integrated at equal intervals around the rim of perforated ring 280.

Sealing Canopy

Referring now to the FIGURES, FIG. 14 is a perspective view of one laser cut stent embodiment showing the articulating collar support structures of the flared end of the tubular stent and passively oscillating dome-shaped sealing canopy attached to the wire halo and the stent body, in cut-away view, with arrows indicating hemodynamic flow into the space between the wire halo and the proximal end of the stent, thus filling the canopy. Note this figure does not illustrate the final valve product as it has neither the surface coatings, e.g. synthetic material and/or stabilized tissue, nor internal leaflet structures have been added.

FIG. 15 is a top view of one embodiment showing the articulating collar support structures of the flared end of the tubular stent and valve leaflets disposed therein. Note this figure does not illustrate the final valve product as it has neither the surface coatings, e.g. synthetic material and/or stabilized tissue, etc. have been added.

FIG. 16 is a top view of one embodiment showing the braided wire collar support structures of the flared end of the tubular stent and valve leaflets disposed therein. Note this figure does not illustrate the final valve product as it has neither the surface coatings, e.g. synthetic material and/or stabilized tissue, etc. have been added.

FIG. 17 is a side view of one braided embodiment showing the braided wire collar support structures of the flared end of the tubular stent and passively oscillating dome-shaped sealing canopy attached to the wire halo and the stent body, in cut-away view to show tether attachments. Note this figure does not illustrate the final valve product as it has neither the surface coatings, e.g. synthetic material and/or stabilized tissue, nor internal leaflet structures have been added.

FIG. 18 is an illustration of a side view with false-transparent detail of the native mitral leaflet structure having the prosthetic valve of the present invention deployed therein (shown without apical tether attached). FIG. 18 shows how a prosthetic valve may inadvertently leave space for regurgitative leaking FIG. 18 also shows passively oscillating dome-shaped sealing canopy in a hemodynamically filled state, and consequently creating a periannular sealing structure outside of the stent body to stop regurgitative leaking FIG. 18 also shows arrows indicating hemodynamic flow into the space between the wire halo and the proximal end of the stent, thus filling the canopy.

FIG. 19 is an illustration of a side view with false-transparent detail of the native left atrium, left ventricle, and mitral leaflet structure having the prosthetic valve of the present invention deployed therein (shown with apical tether attached). FIG. 19 shows how the passively oscillating dome-shaped sealing canopy of the present invention, in a hemodynamically filled state, creates a periannular sealing structure outside of the stent body to stop regurgitative leaking FIG. 18 also shows arrows indicating ventricular contraction, arrows indicating hemodynamic flow into the space between the wire halo and the proximal end of the stent, thus filling the canopy. FIG. 18 also shows arrows indicating that periannular leaking is stopped.

FIG. 20 is an illustration of a prosthetic heart valve of the present inventive subject matter, wherein the valve does not use an anchoring tether or a positioning tether at all, and instead is held in the mitral annulus by the wrapping forces of the native leaflets, and optionally one or more standard anchoring elements, including but not limited to barbs, pins, and/or hooks, or combinations thereof.

FIG. 21 is an illustration of a prosthetic heart valve of the present inventive subject matter wherein the peri-annular sealing component comprises two or more passively oscillating dome-shaped sealing canopies, each comprised of a skirt of stabilized tissue or synthetic material attached on a distal edge of said material at or near the distal end of the stent and attached at a proximal edge to the wire halo apparatus, wherein during systole the leaflet assembly closes and each of the sealing canopies is filled to form multiple redundant periannular seal partitions by retrograde hemodynamic forces.

FIG. 22 is an illustration of a prosthetic heart valve of the present inventive subject matter wherein the peri-annular sealing component comprises an enlarged passively oscillating dome-shaped sealing canopy that has a sub-annular diameter about the same diameter as the atrial collar.

FIG. 23 is an illustration of a prosthetic heart valve of the present inventive subject matter wherein the peri-annular sealing component comprises an enlarged gel-filled sealing chamber that has a sub-annular diameter about the same diameter as the atrial collar and which is attached to the wire halo on the ventricular side and to the stent body on the peri-annular side.

FIG. 24 is an illustration of a prosthetic heart valve of the present inventive subject matter wherein the peri-annular sealing component comprises an enlarged gel-filled sealing chamber that has a sub-annular diameter about the same diameter as the atrial collar and which is attached to the proximal end of the stent body on the ventricular side and to a midline section of the stent body on the peri-annular side.

FIG. 25 is an illustration of a prosthetic heart valve of the present inventive subject matter wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a supra-annular seal partition by retrograde hemodynamic forces.

FIG. 26 is an illustration of a prosthetic heart valve of the present inventive subject matter wherein the peri-annular sealing component comprises a passively filling form-fitting sealing canopy, comprised of a skirt of stabilized tissue or synthetic material attached on a distal edge of said material at or near the distal end of the stent and attached at a proximal edge to the wire halo apparatus, wherein during systole the leaflet assembly closes and the sealing canopy is filled to form a combined sub-annular and supra-annular seal partition by retrograde hemodynamic forces.

Stent-in-a-Stent

Referring now to the FIGURES, FIG. 27 is a perspective view of one laser cut stent embodiment showing the articulating collar having a valve leaflet thru-hole and attached to both the inner and outer stents creating a sub-valvular chamber. FIG. 27 also shows intermediate tethers attached to the base or proximal end of the outer stent and joining at a junction nut with a single anchoring (or positioning) tether extending away toward the epicardial anchor (not shown).

FIG. 28 is a lower perspective view of one embodiment showing the underside of the atrial sealing collar, the low height profile outer stent (and inner stent), the intermediate wire tethers attached at the junction and the single tether extending away. FIG. 28 also shows a leaflet assembly located in the lower section of the inner stent and the outer stent and its covering creating a chamber to assist sealing.

FIG. 29 is a top view of mitral valve anatomy showing anterior and posterior segments (scallops) of the mitral valve.

FIG. 30 is a top view of mitral valve anatomy having a traditional prosthetic valve deployed therein and causing spreading of the A1-P1 and A3-P3 segments, which will result in hemodynamic leakage at the commissural edges of the mitral valve.

FIG. 31 is a top view of mitral valve anatomy having a stent-in-a-stent valve according to the present invention, and showing anterior and posterior segments of the mitral valve fully occupied and distended, addressing the commissural leaking issue.

FIG. 32 is an exploded side view of one embodiment of the present invention, showing from top to bottom, the tissue collar for atrial sealing, the leaflet apparatus, the low-profile laser-cut nitinol inner stent, the inner stent tissue covering, the low-profile laser-cut nitinol outer stent with articulating arms to support the tissue collar, the intermediate wire tethers, the junction nut or collar, the outer stent tissue covering, and the single epicardial tether.

FIG. 33 is an exploded side view of one embodiment of the present invention, showing from top to bottom, the tissue collar for atrial sealing, the leaflet apparatus, the low-profile laser-cut diamond-fold design nitinol inner stent, the inner stent tissue covering, the low-profile laser-cut diamond-fold design nitinol outer stent with articulating arms to support the tissue collar, the intermediate wire tethers, the junction nut or collar, the outer stent tissue covering, and the single epicardial tether.

FIG. 34 is a side view of the outer stent wire form showing the attached atrial collar.

FIG. 35 is a top view of the atrial collar with thru-hole for the inner stent and leaflets (not shown).

FIG. 36 is a lower side view of one embodiment showing the underside of the atrial sealing collar, the low height profile outer stent, the intermediate wire tethers attached at the junction and the single epicardial tether extending away.

FIG. 37 is a lower side view of one embodiment showing the underside of the atrial sealing collar, the low height profile outer stent, the intermediate wire tethers attached at the junction.

FIG. 38 is a side lower perspective view of one embodiment showing the wire-form skeleton of the low height profile outer stent.

FIG. 39 is a side view of one embodiment showing the wire-form skeleton of the low height profile outer stent.

FIG. 40 is a top view of one embodiment showing the wire-form skeleton of the low height profile outer stent.

Trapdoor Sealing Device

Referring now to the FIGURES, FIG. 41 is a perspective view of one laser cut stent embodiment showing the tissue-covered articulating collar structure attached to the expandable tubular nitinol stent with valve leaflets mounted therein, and the trap-door commissural wire-frame tab supports for the commissural sealing skirt.

FIG. 42 is a bottom view of one embodiment showing the trap-door commissural wire-frame tab supports for the commissural sealing skirt. Note this figure may not illustrate the final valve product, as it may have surface coatings, e.g. synthetic material and/or stabilized tissue, etc., added.

FIG. 43 is a perspective lower view of one embodiment showing laser cut stent embodiment showing the tissue-covered articulating collar structure attached to the expandable tubular nitinol stent with valve leaflets mounted therein, and the trap-door commissural wire-frame tab supports for the commissural sealing skirt.

FIG. 44 is a perspective view of one laser-cut embodiment in a minimal wireframe view to highlight the trap-door commissural wire-frame tab supports for the commissural sealing skirt.

FIG. 45 is a perspective view of one laser-cut embodiment in a minimal wireframe view, without lines showing location of the collar, to highlight the trap-door commissural wire-frame tab supports for the commissural sealing skirt.

FIG. 46 is a perspective view of one braided stent embodiment in a minimal wire-frame view to highlight the addition of the trap-door commissural wire-frame tab supports for the commissural sealing skirt.

FIG. 47 is a perspective view of another braided stent embodiment in a minimal wire-frame view to highlight the addition of the trap-door commissural wire-frame tab supports for the commissural sealing skirt.

FIG. 48 is a perspective view of one braided stent embodiment in a minimal wire-frame view to highlight the outside-to-inward folding embodiment of the trap-door commissural wire-frame tab supports for the commissural sealing skirt.

FIG. 49 is a perspective view of a laser-cut stent embodiment in a covered wireframe view to highlight the outside-to-inward folding embodiment of the trap-door commissural wire-frame tab supports for the commissural sealing skirt.

FIG. 50 is a perspective view of one braided stent embodiment in a minimal wire-frame view to highlight the inside-to-outward folding embodiment of the trap-door commissural wire-frame tab supports for the commissural sealing skirt.

FIG. 51 is a perspective view of a laser-cut stent embodiment in a covered wireframe view to highlight the inside-to-outward folding embodiment of the trap-door commissural wire-frame tab supports for the commissural sealing skirt.

FIG. 52 is a perspective view of a laser-cut stent embodiment in a minimal wire-frame view to highlight the elongated-tab embodiment of the trap-door commissural wire-frame tab supports for the commissural sealing skirt.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A prosthetic mitral valve comprising:
   an outer stent having an atrium end;
   a circumferentially continuous tissue collar for atrial sealing, supported by a first end of said outer stent;
   an inner stent having a diameter smaller than a diameter of said outer stent and being disposed in said outer stent such that a gap is defined between said outer stent and said inner stent, said tissue collar being coupled to a first end of said inner stent such that said tissue collar extends across the gap from said outer stent to said inner stent to limit flow through the gap;
   a leaflet apparatus disposed in said inner stent;
   a plurality of wire tethers each having a first end coupled to a ventricle end of said outer stent and extending therefrom, each of said plurality of wire tethers having a second end;
   a junction nut coupled to said second ends of said plurality of wire tethers; and
   an anchoring tether coupled to and extending from said junction nut.

2. The valve of claim 1, wherein said leaflet apparatus is disposed in a ventricle section of said inner stent proximate to said ventricle end of said outer stent.

3. The valve of claim 1, wherein said atrium end of said outer stent includes a plurality of articulating arms extending radially therefrom, said tissue collar being supported on said plurality of articulating arms.

4. The valve of claim 1, wherein said tissue collar is integrally formed with said outer stent.

5. The valve of claim 1, wherein said tissue collar is formed separately from and coupled to said outer stent.

6. The valve of claim 1, further comprising:
   a tissue covering disposed about an interior portion of said outer stent.

7. The valve of claim 1, wherein said outer stent extends longitudinally from said atrium end of said outer stent to a ventricle end of said outer stent opposite to said atrium end of said outer stent, said tissue collar extending radially from said atrium end of said outer stent.

8. The valve of claim 1, wherein said tissue collar is further coupled to a first end of said inner stent, creating a subvalvular chamber between said inner stent, said outer stent, and said tissue collar.

9. The valve of claim 1, wherein said outer stent is configured to extend from an atrium of a heart to a ventricle of said heart and said tissue collar is configured to extend radially in said atrium of said heart, when said valve is seated in a native atrioventricular annulus of said heart.

10. The valve of claim 1, wherein said tissue collar is configured to conform to an anatomical shape of an annulus of a heart and maintain said conformity during a cardiac cycle of said heart.

11. The valve of claim 1, wherein multiple interior portions of said outer stent are spaced apart radially from said inner stent.

12. The valve of claim 1, wherein the first end of the outer stent is the same end as the atrium end of the outer stent.

13. The valve of claim 1, wherein the tissue collar is supported by a first end of said outer stent.

14. The valve of claim 13, wherein the first end of the outer stent is the same end as the atrium end of the outer stent.

15. A prosthetic mitral valve comprising:
   an outer tubular stent having a distal end and a proximal end;
   a circumferentially continuous tissue collar for atrial sealing, supported by an end of said outer tubular stent;
   an inner tubular stent having a diameter smaller than a diameter of said outer tubular stent and being disposed in said outer tubular stent such that a gap is defined between said outer tubular stent and said inner stent, said tissue collar being coupled to a first end of said inner stent such that said tissue collar extends across the gap from said outer tubular stent to said inner stent to limit flow through the gap;
   a plurality of wire tethers each having a first end coupled to the proximal end of said outer tubular stent and extending therefrom, each of said plurality of wire tethers having a second end;
   a junction nut coupled to said second ends of said plurality of wire tethers;
   an anchoring tether coupled to and extending from said junction nut; and
   a leaflet apparatus disposed in said inner tubular stent.

16. The valve of claim 15, wherein said tissue collar is further coupled to the distal end of said inner tubular stent, creating a subvalvular chamber between said inner stent, said outer stent, and said tissue collar.

17. The valve of claim 15, wherein said leaflet apparatus is disposed in a lower section of said inner tubular stent proximate to said distal end of said outer tubular stent.

18. The valve of claim 15, wherein said distal end of said outer tubular stent includes a plurality of articulating arms extending radially therefrom, said tissue collar being supported on said plurality of articulating arms.

19. The valve of claim 15, wherein the end of the outer tubular stent that supports the tissue collar is the distal end of the outer tubular stent.

* * * * *